(12) United States Patent
Chen et al.

(10) Patent No.: US 11,773,385 B2
(45) Date of Patent: Oct. 3, 2023

(54) HIGH-AFFINITY HUMAN ACE2 CONSTRUCT FOR USE IN DIAGNOSING AND TREATING CORONAVIRUSES

(71) Applicant: Children's Medical Center Corporation, Boston, MA (US)

(72) Inventors: Bing Chen, Westwood, MA (US); Tianshu Xiao, Boston, MA (US); Yongfei Cai, Boston, MA (US); Jun Zhang, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 301 days.

(21) Appl. No.: 17/324,585

(22) Filed: May 19, 2021

(65) Prior Publication Data

US 2022/0002701 A1   Jan. 6, 2022

Related U.S. Application Data

(60) Provisional application No. 63/080,573, filed on Sep. 18, 2020, provisional application No. 63/027,304, filed on May 19, 2020.

(51) Int. Cl.
*C12N 9/48* (2006.01)
*C07K 14/36* (2006.01)
*G01N 33/569* (2006.01)
*A61K 38/00* (2006.01)

(52) U.S. Cl.
CPC .............. *C12N 9/485* (2013.01); *C07K 14/36* (2013.01); *C12Y 304/17023* (2013.01); *G01N 33/56983* (2013.01); *A61K 38/00* (2013.01); *C07K 2319/00* (2013.01); *G01N 2333/165* (2013.01)

(58) Field of Classification Search
None
See application file for complete search history.

(56) References Cited

U.S. PATENT DOCUMENTS 11,078,471 B2 * 8/2021 Batlle .................. C07K 14/765

* cited by examiner

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

Provided herein, in some aspects, are polypeptide monomers comprising an angiotensin-converting enzyme 2 (ACE2) ectodomain and an oligomerization domain. Also provided herein are oligomeric complexes comprising ACE2 monomers. Methods of using such to monomers and oligomeric complexes for the diagnosis, prevention, and treatment of viral infections such as the coronavirus are also provided.

18 Claims, 32 Drawing Sheets

Specification includes a Sequence Listing.

S trimer immobilized/trimeric ACE2 passing over (with avidity)

$k_a = 2.44e5\ (M^{-1}s^{-1})$
$k_d = 3.39e\text{-}4\ (s^{-1})$
$K_D = 1.4\ nM$

| Construct | ACE2615 | ACE2615-Fc | ACE2740-Fc | ACE2615-foldon | ACE2615-LL-foldon | ACE2615-foldon -T27Y | ACE2615-foldon -T27W | ACE2615-foldon -H34W | ACE2615-foldon -K353Y |
|---|---|---|---|---|---|---|---|---|---|
| KD (nM) | 76.8±0.8 | 22.3±2.2 | 12.4±0.6 | 1.15±0.05 | 0.62±0.03 | 0.09±0.01 | 0.06±0.01 | 0.37±0.01 | 32.3±1.8 |

FIG. 8C

SEQUENCE LISTING

```
<160> NUMBER OF SEQ ID NOS: 33

<210> SEQ ID NO 1
<211> LENGTH: 625
<212> TYPE: PRT
<213> ORGANISM: Artificial Sequence
<220> FEATURE:
<223> OTHER INFORMATION: Synthetic Polypeptide

<400> SEQUENCE: 1

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255
```

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
    275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
            595                 600                 605

Asp Trp Ser Pro Tyr Ala Asp Ser Gly Gly Ser His His His His His
            610                 615                 620

His
625

<210> SEQ ID NO 2
<211> LENGTH: 661
<212> TYPE: PRT
<213> ORGANISM: Artificial Sequence
<220> FEATURE:
<223> OTHER INFORMATION: Synthetic Polypeptide -continued

```
<400> SEQUENCE: 2

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
```

His Leu Lys Ser Ile Gly Leu Leu Ser Pro Asp Phe Gln Glu Asp Asn
            405                 410                 415

Glu Thr Glu Ile Asn Phe Leu Leu Lys Gln Ala Leu Thr Ile Val Gly
        420                 425                 430

Thr Leu Pro Phe Thr Tyr Met Leu Glu Lys Trp Arg Trp Met Val Phe
    435                 440                 445

Lys Gly Glu Ile Pro Lys Asp Gln Trp Met Lys Lys Trp Trp Glu Met
450                 455                 460

Lys Arg Glu Ile Val Gly Val Val Glu Pro Val Pro His Asp Glu Thr
465                 470                 475                 480

Tyr Cys Asp Pro Ala Ser Leu Phe His Val Ser Asn Asp Tyr Ser Phe
            485                 490                 495

Ile Arg Tyr Tyr Thr Arg Thr Leu Tyr Gln Phe Gln Phe Gln Glu Ala
        500                 505                 510

Leu Cys Gln Ala Ala Lys His Glu Gly Pro Leu His Lys Cys Asp Ile
    515                 520                 525

Ser Asn Ser Thr Glu Ala Gly Gln Lys Leu Phe Asn Met Leu Arg Leu
530                 535                 540

Gly Lys Ser Glu Pro Trp Thr Leu Ala Leu Glu Asn Val Val Gly Ala
545                 550                 555                 560

Lys Asn Met Asn Val Arg Pro Leu Leu Asn Tyr Phe Glu Pro Leu Phe
            565                 570                 575

Thr Trp Leu Lys Asp Gln Asn Lys Asn Ser Phe Val Gly Trp Ser Thr
        580                 585                 590

Asp Trp Ser Pro Tyr Ala Asp Ser Gly Gly Ser Leu Glu Gly Gly Ser
    595                 600                 605

Gly Gly Tyr Ile Pro Glu Ala Pro Arg Asp Gly Gln Ala Tyr Val Arg
610                 615                 620

Lys Asp Gly Glu Trp Val Leu Leu Ser Thr Phe Leu Gly Gly Ser His
625                 630                 635                 640

His His His His His
            645                 650                 655

<210> SEQ ID NO 3
<211> LENGTH: 658
<212> TYPE: PRT
<213> ORGANISM: Artificial Sequence
<220> FEATURE:
<223> OTHER INFORMATION: Synthetic Polypeptide

<400> SEQUENCE: 3

Met Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
            85                  90                  95

Leu Gln Ala Leu Gln Gln Asn Gly Ser Ser Val Leu Ser Glu Asp Lys

-continued

```
                100                 105                 110
Ser Lys Arg Leu Asn Thr Ile Leu Asn Thr Met Ser Thr Ile Tyr Ser
            115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Cys Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Cys
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525
```

Leu Cys Gln Ala Ala Lys His Glu Gly Pro Leu His Lys Cys Asp Ile
            530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
            595                 600                 605

Asp Trp Ser Pro Tyr Ala Asp Ser Gly Gly Gly Ser Gly Gly Tyr
            610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His His
                645                 650                 655

His His

<210> SEQ ID NO 4
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (275)..(448)

<400> SEQUENCE: 4

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
        50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

-continued

```
Val Asn Gly Val Asp Gly Tyr Asp Tyr Ser Arg Gly Gln Leu Ile Glu
    210                 215                 220
Asp Val Glu His Thr Phe Glu Ile Lys Pro Leu Tyr Glu His Leu
225                 230                 235                 240
His Ala Tyr Val Arg Ala Lys Leu Met Asn Ala Tyr Pro Ser Tyr Ile
                245                 250                 255
Ser Pro Ile Gly Cys Leu Pro Ala His Leu Leu Gly Asp Met Trp Gly
                260                 265                 270
Arg Phe Cys Thr Asn Leu Tyr Ser Leu Thr Val Pro Phe Gly Gln Lys
            275                 280                 285
Pro Asn Ile Asp Val Thr Asp Ala Met Val Asp Gln Ala Trp Asp Ala
290                 295                 300
Gln Arg Ile Phe Lys Glu Ala Glu Lys Phe Phe Val Ser Val Gly Leu
305                 310                 315                 320
Pro Asn Met Thr Gln Gly Phe Trp Glu Asn Ser Met Leu Thr Asp Pro
                325                 330                 335
Gly Asn Val Gln Lys Ala Val Cys His Pro Thr Ala Trp Asp Leu Gly
                340                 345                 350
Lys Gly Asp Phe Arg Ile Leu Met Cys Thr Lys Val Thr Met Asp Asp
            355                 360                 365
Phe Leu Thr Ala His His Glu Met Gly His Ile Gln Tyr Asp Met Ala
370                 375                 380
Tyr Ala Ala Gln Pro Phe Leu Leu Arg Asn Gly Ala Asn Glu Gly Phe
385                 390                 395                 400
His Glu Ala Val Gly Glu Ile Met Ser Leu Ser Ala Ala Thr Pro Lys
                405                 410                 415
His Leu Lys Ser Ile Gly Leu Leu Ser Pro Asp Phe Gln Glu Asp Asn
            420                 425                 430
Glu Thr Glu Ile Asn Phe Leu Leu Lys Gln Ala Leu Thr Ile Val Cys
        435                 440                 445
Thr Leu Pro Phe Thr Tyr Met Leu Glu Lys Trp Arg Trp Met Val Phe
450                 455                 460
Lys Gly Glu Ile Pro Lys Asp Gln Trp Met Lys Lys Trp Trp Glu Met
465                 470                 475                 480
Lys Arg Glu Ile Val Gly Val Val Glu Pro Val Pro His Asp Glu Thr
                485                 490                 495
Tyr Cys Asp Pro Ala Ser Leu Phe His Val Ser Asn Asp Tyr Ser Phe
                500                 505                 510
Ile Arg Tyr Tyr Thr Arg Thr Leu Tyr Gln Phe Gln Phe Gln Glu Ala
            515                 520                 525
Leu Cys Gln Ala Ala Lys His Glu Gly Pro Leu His Lys Cys Asp Ile
530                 535                 540
Ser Asn Ser Thr Glu Ala Gly Gln Lys Leu Phe Asn Met Leu Arg Leu
545                 550                 555                 560
Gly Lys Ser Glu Pro Trp Thr Leu Ala Leu Glu Asn Val Val Gly Ala
                565                 570                 575
Lys Asn Met Asn Val Arg Pro Leu Leu Asn Tyr Phe Glu Pro Leu Phe
            580                 585                 590
Thr Trp Leu Lys Asp Gln Asn Lys Asn Ser Phe Val Gly Trp Ser Thr
        595                 600                 605
Asp Trp Ser Pro Tyr Ala Asp Ser Gly Gly Gly Ser Gly Gly Tyr
610                 615                 620
Ile Pro Glu Ala Pro Arg Asp Gly Gln Ala Tyr Val Arg Lys Asp Gly
```

```
                625                 630                 635                 640
Glu Trp Val Leu Leu Ser Thr Phe Leu Gly Gly Ser His His His His
                    645                 650                 655
His His

<210> SEQ ID NO 5
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (377)..(408)

<400> SEQUENCE: 5

Met Ser Ser Ser Ser Trp Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320
```

```
Pro Asn Met Thr Gln Gly Phe Trp Glu Asn Ser Met Leu Thr Asp Pro
            325                 330                 335

Gly Asn Val Gln Lys Ala Val Cys His Pro Thr Ala Trp Asp Leu Gly
        340                 345                 350

Lys Gly Asp Phe Arg Ile Leu Met Cys Thr Lys Val Thr Met Asp Asp
    355                 360                 365

Phe Leu Thr Ala His His Glu Met Cys His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Cys Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Ser Gly Gly Gly Ser Gly Gly Tyr
    610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His His
                645                 650                 655

His His
```

<210> SEQ ID NO 6
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (523)..(583)

<400> SEQUENCE: 6

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
            115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
            275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
```

```
                420                 425                 430
Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
        450                 455                 460

Lys Gly Glu Ile Pro Lys Asp Gln Trp Met Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Cys Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Cys Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Ser Gly Gly Gly Ser Gly Gly Tyr
    610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His
                645                 650                 655

His His

<210> SEQ ID NO 7
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (523)..(584)

<400> SEQUENCE: 7

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110
```

```
Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
            165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
        210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
            245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
            275                 280                 285

Pro Asn Ile Asp Val Thr Asp Ala Met Val Asp Gln Ala Trp Asp Ala
            290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
            325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
            370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
            405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
            450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
            485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Cys Gln Phe Gln Glu Ala
            515                 520                 525
```

-continued

```
Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Cys Leu Asn Tyr Phe Glu Pro Leu Phe
                580                 585                 590

Thr Trp Leu Lys Asp Gln Asn Lys Asn Ser Phe Val Gly Trp Ser Thr
            595                 600                 605

Asp Trp Ser Pro Tyr Ala Asp Ser Gly Gly Gly Ser Gly Gly Tyr
610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His His
                645                 650                 655

His His
```

```
<210> SEQ ID NO 8
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (275)..(448)
<220> FEATURE:
<221> NAME/KEY: DISULFID
<222> LOCATION: (377)..(408)

<400> SEQUENCE: 8
```

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
```

```
            195                 200                 205
Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Cys Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Cys His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Cys Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Cys
        435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Ser Gly Gly Gly Ser Gly Gly Gly Tyr
610                 615                 620
```

-continued

```
Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His His
                645                 650                 655

His His
```

<210> SEQ ID NO 9
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (275)..(448)
<220> FEATURE:
<221> NAME/KEY: DISULFID
<222> LOCATION: (523)..(583)

<400> SEQUENCE: 9

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
        50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Cys Thr Asn Leu Tyr Ser Leu Thr Val Pro Phe Gly Gln Lys
        275                 280                 285
```

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
            325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Cys
            435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Cys Gln Phe Gln Glu Ala
            515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Cys Leu Leu Asn Tyr Phe Glu Pro Leu Phe
            580                 585                 590

Thr Trp Leu Lys Asp Gln Asn Lys Asn Ser Phe Val Gly Trp Ser Thr
            595                 600                 605

Asp Trp Ser Pro Tyr Ala Asp Ser Gly Gly Gly Ser Gly Gly Tyr
610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His
                645                 650                 655

His His

<210> SEQ ID NO 10
<211> LENGTH: 658
<212> TYPE: PRT
<213> ORGANISM: Artificial Sequence
<220> FEATURE:
<223> OTHER INFORMATION: Synthetic Polypeptide
<220> FEATURE:

```
<221> NAME/KEY: DISULFID
<222> LOCATION: (275)..(448)
<220> FEATURE:
<221> NAME/KEY: DISULFID
<222> LOCATION: (523)..(584)

<400> SEQUENCE: 10

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Cys Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380
```

```
Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
            405                 410                 415

His Leu Lys Ser Ile Gly Leu Leu Ser Pro Asp Phe Gln Glu Asp Asn
        420                 425                 430

Glu Thr Glu Ile Asn Phe Leu Leu Lys Gln Ala Leu Thr Ile Val Cys
    435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Cys Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Cys Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Ser Gly Gly Gly Ser Gly Gly Tyr
    610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His His
                645                 650                 655

His His

<210> SEQ ID NO 11
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (377)..(408)
<220> FEATURE:
<221> NAME/KEY: DISULFID
<222> LOCATION: (523)..(583)

<400> SEQUENCE: 11

Met Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45
```

-continued

```
Asn Tyr Asn Thr Asn Ile Thr Glu Glu Asn Val Gln Asn Met Asn Asn
     50                  55                  60
Ala Gly Asp Lys Trp Ser Ala Phe Leu Lys Glu Gln Ser Thr Leu Ala
 65                  70                  75                  80
Gln Met Tyr Pro Leu Gln Glu Ile Gln Asn Leu Thr Val Lys Leu Gln
                 85                  90                  95
Leu Gln Ala Leu Gln Gln Asn Gly Ser Ser Val Leu Ser Glu Asp Lys
            100                 105                 110
Ser Lys Arg Leu Asn Thr Ile Leu Asn Thr Met Ser Thr Ile Tyr Ser
        115                 120                 125
Thr Gly Lys Val Cys Asn Pro Asp Asn Pro Gln Glu Cys Leu Leu Leu
    130                 135                 140
Glu Pro Gly Leu Asn Glu Ile Met Ala Asn Ser Leu Asp Tyr Asn Glu
145                 150                 155                 160
Arg Leu Trp Ala Trp Glu Ser Trp Arg Ser Glu Val Gly Lys Gln Leu
                165                 170                 175
Arg Pro Leu Tyr Glu Glu Tyr Val Val Leu Lys Asn Glu Met Ala Arg
            180                 185                 190
Ala Asn His Tyr Glu Asp Tyr Gly Asp Tyr Trp Arg Gly Asp Tyr Glu
        195                 200                 205
Val Asn Gly Val Asp Gly Tyr Asp Tyr Ser Arg Gly Gln Leu Ile Glu
    210                 215                 220
Asp Val Glu His Thr Phe Glu Glu Ile Lys Pro Leu Tyr Glu His Leu
225                 230                 235                 240
His Ala Tyr Val Arg Ala Lys Leu Met Asn Ala Tyr Pro Ser Tyr Ile
                245                 250                 255
Ser Pro Ile Gly Cys Leu Pro Ala His Leu Leu Gly Asp Met Trp Gly
            260                 265                 270
Arg Phe Trp Thr Asn Leu Tyr Ser Leu Thr Val Pro Phe Gly Gln Lys
        275                 280                 285
Pro Asn Ile Asp Val Thr Asp Ala Met Val Asp Gln Ala Trp Asp Ala
    290                 295                 300
Gln Arg Ile Phe Lys Glu Ala Glu Lys Phe Phe Val Ser Val Gly Leu
305                 310                 315                 320
Pro Asn Met Thr Gln Gly Phe Trp Glu Asn Ser Met Leu Thr Asp Pro
                325                 330                 335
Gly Asn Val Gln Lys Ala Val Cys His Pro Thr Ala Trp Asp Leu Gly
            340                 345                 350
Lys Gly Asp Phe Arg Ile Leu Met Cys Thr Lys Val Thr Met Asp Asp
        355                 360                 365
Phe Leu Thr Ala His His Glu Met Cys His Ile Gln Tyr Asp Met Ala
    370                 375                 380
Tyr Ala Ala Gln Pro Phe Leu Leu Arg Asn Gly Ala Asn Glu Gly Phe
385                 390                 395                 400
His Glu Ala Val Gly Glu Ile Cys Ser Leu Ser Ala Ala Thr Pro Lys
                405                 410                 415
His Leu Lys Ser Ile Gly Leu Leu Ser Pro Asp Phe Gln Glu Asp Asn
            420                 425                 430
Glu Thr Glu Ile Asn Phe Leu Leu Lys Gln Ala Leu Thr Ile Val Gly
        435                 440                 445
Thr Leu Pro Phe Thr Tyr Met Leu Glu Lys Trp Arg Trp Met Val Phe
    450                 455                 460
Lys Gly Glu Ile Pro Lys Asp Gln Trp Met Lys Lys Trp Trp Glu Met
```

```
                465                 470                 475                 480
Lys Arg Glu Ile Val Gly Val Glu Pro Val Pro His Asp Glu Thr
                    485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Cys Gln Phe Gln Glu Ala
                515                 520                 525

Leu Cys Gln Ala Ala Lys His Glu Gly Pro Leu His Lys Cys Asp Ile
            530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Cys Leu Leu Asn Tyr Phe Glu Pro Leu Phe
                580                 585                 590

Thr Trp Leu Lys Asp Gln Asn Lys Asn Ser Phe Val Gly Trp Ser Thr
                595                 600                 605

Asp Trp Ser Pro Tyr Ala Asp Ser Gly Gly Gly Ser Gly Gly Tyr
            610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His His
                    645                 650                 655

His His

<210> SEQ ID NO 12
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (377)..(408)
<220> FEATURE:
<221> NAME/KEY: DISULFID
<222> LOCATION: (523)..(584)

<400> SEQUENCE: 12

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140
```

```
Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
            165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
            195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
            245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
            275                 280                 285

Pro Asn Ile Asp Val Thr Asp Ala Met Val Asp Gln Ala Trp Asp Ala
            290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
            325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
            355                 360                 365

Phe Leu Thr Ala His His Glu Met Cys His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Cys Ser Leu Ser Ala Ala Thr Pro Lys
            405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
            450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
            485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Cys Gln Phe Gln Glu Ala
            515                 520                 525

Leu Cys Gln Ala Ala Lys His Glu Gly Pro Leu His Lys Cys Asp Ile
            530                 535                 540

Ser Asn Ser Thr Glu Ala Gly Gln Lys Leu Phe Asn Met Leu Arg Leu
545                 550                 555                 560
```

-continued

```
Gly Lys Ser Glu Pro Trp Thr Leu Ala Leu Glu Asn Val Val Gly Ala
                565                 570                 575

Lys Asn Met Asn Val Arg Pro Cys Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Ser Gly Gly Gly Ser Gly Gly Tyr
    610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His His
                645                 650                 655

His His
```

<210> SEQ ID NO 13
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (275)..(448)
<220> FEATURE:
<221> NAME/KEY: DISULFID
<222> LOCATION: (377)..(408)
<220> FEATURE:
<221> NAME/KEY: DISULFID
<222> LOCATION: (523)..(583)

<400> SEQUENCE: 13

```
Met Ser Ser Ser Ser Trp Leu Leu Ser Leu Val Ala Val Thr Ala
1               5                   10                  15

Ala Gln Ser Thr Ile Glu Glu Gln Ala Lys Thr Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
        50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
```

```
                210                 215                 220
Asp Val Glu His Thr Phe Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Cys Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Cys His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Cys Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Cys
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Cys Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Cys Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Ser Gly Gly Gly Ser Gly Gly Tyr
    610                 615                 620

Ile Pro Glu Ala Pro Arg Asp Gly Gln Ala Tyr Val Arg Lys Asp Gly
625                 630                 635                 640
```

```
Glu Trp Val Leu Leu Ser Thr Phe Leu Gly Gly Ser His His His
                    645                 650                 655

His His

<210> SEQ ID NO 14
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: DISULFID
<222> LOCATION: (275)..(448)
<220> FEATURE:
<221> NAME/KEY: DISULFID
<222> LOCATION: (377)..(408)
<220> FEATURE:
<221> NAME/KEY: DISULFID
<222> LOCATION: (523)..(584)

<400> SEQUENCE: 14

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Cys Thr Asn Leu Tyr Ser Leu Thr Val Pro Phe Gly Gln Lys
        275                 280                 285
```

```
Pro Asn Ile Asp Val Thr Asp Ala Met Val Asp Gln Ala Trp Asp Ala
    290                 295                 300
Gln Arg Ile Phe Lys Glu Ala Glu Lys Phe Phe Val Ser Val Gly Leu
305                 310                 315                 320
Pro Asn Met Thr Gln Gly Phe Trp Glu Asn Ser Met Leu Thr Asp Pro
                325                 330                 335
Gly Asn Val Gln Lys Ala Val Cys His Pro Thr Ala Trp Asp Leu Gly
                340                 345                 350
Lys Gly Asp Phe Arg Ile Leu Met Cys Thr Lys Val Thr Met Asp Asp
                355                 360                 365
Phe Leu Thr Ala His His Glu Met Cys His Ile Gln Tyr Asp Met Ala
    370                 375                 380
Tyr Ala Ala Gln Pro Phe Leu Leu Arg Asn Gly Ala Asn Glu Gly Phe
385                 390                 395                 400
His Glu Ala Val Gly Glu Ile Cys Ser Leu Ser Ala Ala Thr Pro Lys
                405                 410                 415
His Leu Lys Ser Ile Gly Leu Leu Ser Pro Asp Phe Gln Glu Asp Asn
                420                 425                 430
Glu Thr Glu Ile Asn Phe Leu Leu Lys Gln Ala Leu Thr Ile Val Cys
            435                 440                 445
Thr Leu Pro Phe Thr Tyr Met Leu Glu Lys Trp Arg Trp Met Val Phe
450                 455                 460
Lys Gly Glu Ile Pro Lys Asp Gln Trp Met Lys Lys Trp Trp Glu Met
465                 470                 475                 480
Lys Arg Glu Ile Val Gly Val Val Glu Pro Val Pro His Asp Glu Thr
                485                 490                 495
Tyr Cys Asp Pro Ala Ser Leu Phe His Val Ser Asn Asp Tyr Ser Phe
            500                 505                 510
Ile Arg Tyr Tyr Thr Arg Thr Leu Tyr Gln Cys Gln Phe Gln Glu Ala
            515                 520                 525
Leu Cys Gln Ala Ala Lys His Glu Gly Pro Leu His Lys Cys Asp Ile
    530                 535                 540
Ser Asn Ser Thr Glu Ala Gly Gln Lys Leu Phe Asn Met Leu Arg Leu
545                 550                 555                 560
Gly Lys Ser Glu Pro Trp Thr Leu Ala Leu Glu Asn Val Val Gly Ala
                565                 570                 575
Lys Asn Met Asn Val Arg Pro Cys Leu Asn Tyr Phe Glu Pro Leu Phe
                580                 585                 590
Thr Trp Leu Lys Asp Gln Asn Lys Asn Ser Phe Val Gly Trp Ser Thr
            595                 600                 605
Asp Trp Ser Pro Tyr Ala Asp Ser Gly Gly Gly Ser Gly Gly Tyr
    610                 615                 620
Ile Pro Glu Ala Pro Arg Asp Gly Gln Ala Tyr Val Arg Lys Asp Gly
625                 630                 635                 640
Glu Trp Val Leu Leu Ser Thr Phe Leu Gly Gly Ser His His His
                645                 650                 655
His His

<210> SEQ ID NO 15
<211> LENGTH: 4
<212> TYPE: PRT
<213> ORGANISM: Artificial Sequence
<220> FEATURE:
<223> OTHER INFORMATION: Synthetic Polypeptide
```

<400> SEQUENCE: 15

Gly Gly Ser Gly
1

<210> SEQ ID NO 16
<211> LENGTH: 658
<212> TYPE: PRT
<213> ORGANISM: Artificial Sequence
<220> FEATURE:
<223> OTHER INFORMATION: Synthetic Polypeptide

<400> SEQUENCE: 16

```
Met Ser Ser Ser Trp Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn Trp Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
```

```
            340                 345                 350
Lys Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
        370                 375                 380

Tyr Ala Ala Gln Pro Phe Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Ser Gly Gly Gly Ser Gly Gly Tyr
    610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His His
                645                 650                 655

His His

<210> SEQ ID NO 17
<211> LENGTH: 658
<212> TYPE: PRT
<213> ORGANISM: Artificial Sequence
<220> FEATURE:
<223> OTHER INFORMATION: Synthetic Polypeptide

<400> SEQUENCE: 17

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn Phe Glu Ala Glu Asp Leu Phe Tyr Gln Ser Ser Leu Ala Ser Trp
        35                  40                  45
```

-continued

```
Asn Tyr Asn Thr Asn Ile Thr Glu Glu Asn Val Gln Asn Met Asn Asn
         50                  55                  60

Ala Gly Asp Lys Trp Ser Ala Phe Leu Lys Glu Gln Ser Thr Leu Ala
 65                  70                  75                  80

Gln Met Tyr Pro Leu Gln Glu Ile Gln Asn Leu Thr Val Lys Leu Gln
                 85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460
```

```
Lys Gly Glu Ile Pro Lys Asp Gln Trp Met Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Phe Gln Phe Gln Glu Ala
                515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
                595                 600                 605

Asp Trp Ser Pro Tyr Ala Asp Ser Gly Gly Gly Ser Gly Gly Tyr
610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His
                645                 650                 655

His His

<210> SEQ ID NO 18
<211> LENGTH: 658
<212> TYPE: PRT
<213> ORGANISM: Artificial Sequence
<220> FEATURE:
<223> OTHER INFORMATION: Synthetic Polypeptide

<400> SEQUENCE: 18

Met Ser Ser Ser Trp Leu Leu Leu Ser Leu Val Ala Val Thr Ala
1               5                   10                  15

Ala Gln Ser Thr Ile Glu Glu Gln Ala Lys Trp Phe Leu Asp Lys Phe
                20                  25                  30

Asn His Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
```

```
            165                 170                 175
Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
            195                 200                 205

Val Asn Gly Val Asp Gly Tyr Asp Tyr Ser Arg Gly Gln Leu Ile Glu
            210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
            245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
            275                 280                 285

Pro Asn Ile Asp Val Thr Asp Ala Met Val Asp Gln Ala Trp Asp Ala
            290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
            325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
            405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
            450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
            485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
            530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
            565                 570                 575

Lys Asn Met Asn Val Arg Pro Leu Leu Asn Tyr Phe Glu Pro Leu Phe
            580                 585                 590
```

```
Thr Trp Leu Lys Asp Gln Asn Lys Asn Ser Phe Val Gly Trp Ser Thr
            595                 600                 605

Asp Trp Ser Pro Tyr Ala Asp Ser Gly Gly Gly Ser Gly Gly Tyr
    610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His
            645                 650                 655

His His
```

<210> SEQ ID NO 19
<211> LENGTH: 658
<212> TYPE: PRT
<213> ORGANISM: Artificial Sequence
<220> FEATURE:
<223> OTHER INFORMATION: Synthetic Polypeptide

<400> SEQUENCE: 19

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Tyr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285
```

```
Pro Asn Ile Asp Val Thr Asp Ala Met Val Asp Gln Ala Trp Asp Ala
    290                 295                 300
Gln Arg Ile Phe Lys Glu Ala Glu Lys Phe Phe Val Ser Val Gly Leu
305                 310                 315                 320
Pro Asn Met Thr Gln Gly Phe Trp Glu Asn Ser Met Leu Thr Asp Pro
                325                 330                 335
Gly Asn Val Gln Lys Ala Val Cys His Pro Thr Ala Trp Asp Leu Gly
            340                 345                 350
Lys Gly Asp Phe Arg Ile Leu Met Cys Thr Lys Val Thr Met Asp Asp
        355                 360                 365
Phe Leu Thr Ala His His Glu Met Gly His Ile Gln Tyr Asp Met Ala
    370                 375                 380
Tyr Ala Ala Gln Pro Phe Leu Leu Arg Asn Gly Ala Asn Glu Gly Phe
385                 390                 395                 400
His Glu Ala Val Gly Glu Ile Met Ser Leu Ser Ala Ala Thr Pro Lys
                405                 410                 415
His Leu Lys Ser Ile Gly Leu Leu Ser Pro Asp Phe Gln Glu Asp Asn
            420                 425                 430
Glu Thr Glu Ile Asn Phe Leu Leu Lys Gln Ala Leu Thr Ile Val Gly
        435                 440                 445
Thr Leu Pro Phe Thr Tyr Met Leu Glu Lys Trp Arg Trp Met Val Phe
    450                 455                 460
Lys Gly Glu Ile Pro Lys Asp Gln Trp Met Lys Lys Trp Trp Glu Met
465                 470                 475                 480
Lys Arg Glu Ile Val Gly Val Val Glu Pro Val Pro His Asp Glu Thr
                485                 490                 495
Tyr Cys Asp Pro Ala Ser Leu Phe His Val Ser Asn Asp Tyr Ser Phe
            500                 505                 510
Ile Arg Tyr Tyr Thr Arg Thr Leu Tyr Gln Phe Gln Phe Gln Glu Ala
        515                 520                 525
Leu Cys Gln Ala Ala Lys His Glu Gly Pro Leu His Lys Cys Asp Ile
    530                 535                 540
Ser Asn Ser Thr Glu Ala Gly Gln Lys Leu Phe Asn Met Leu Arg Leu
545                 550                 555                 560
Gly Lys Ser Glu Pro Trp Thr Leu Ala Leu Glu Asn Val Val Gly Ala
                565                 570                 575
Lys Asn Met Asn Val Arg Pro Leu Leu Asn Tyr Phe Glu Pro Leu Phe
            580                 585                 590
Thr Trp Leu Lys Asp Gln Asn Lys Asn Ser Phe Val Gly Trp Ser Thr
        595                 600                 605
Asp Trp Ser Pro Tyr Ala Asp Ser Gly Gly Gly Ser Gly Gly Tyr
    610                 615                 620
Ile Pro Glu Ala Pro Arg Asp Gly Gln Ala Tyr Val Arg Lys Asp Gly
625                 630                 635                 640
Glu Trp Val Leu Leu Ser Thr Phe Leu Gly Gly Ser His His His His
                645                 650                 655
His His

<210> SEQ ID NO 20
<211> LENGTH: 658
<212> TYPE: PRT
<213> ORGANISM: Artificial Sequence
<220> FEATURE:
<223> OTHER INFORMATION: Synthetic Polypeptide
```

<400> SEQUENCE: 20

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Trp Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415
```

His Leu Lys Ser Ile Gly Leu Ser Pro Asp Phe Gln Glu Asp Asn
              420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Ser Gly Gly Gly Ser Gly Gly Tyr
    610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His
                645                 650                 655

His His

<210> SEQ ID NO 21
<211> LENGTH: 658
<212> TYPE: PRT
<213> ORGANISM: Artificial Sequence
<220> FEATURE:
<223> OTHER INFORMATION: Synthetic Polypeptide

<400> SEQUENCE: 21

Met Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

```
Ser Lys Arg Leu Asn Thr Ile Leu Asn Thr Met Ser Thr Ile Tyr Ser
            115                 120                 125

Thr Gly Lys Val Cys Asn Pro Asp Asn Pro Gln Glu Cys Leu Leu Leu
        130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Tyr Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
```

```
                    530                 535                 540
Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
            595                 600                 605

Asp Trp Ser Pro Tyr Ala Asp Ser Gly Gly Gly Ser Gly Gly Tyr
            610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His His
                    645                 650                 655

His His

<210> SEQ ID NO 22
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (27)..(27)
<223> OTHER INFORMATION: Xaa is Thr, Trp or Tyr
<220> FEATURE:
<221> NAME/KEY: misc_feature
<222> LOCATION: (34)..(34)
<223> OTHER INFORMATION: Xaa is His, Phe, or Trp
<220> FEATURE:
<221> NAME/KEY: misc_feature
<222> LOCATION: (353)..(353)
<223> OTHER INFORMATION: Xaa is Lys, Trp, or Tyr

<400> SEQUENCE: 22

Met Ser Ser Ser Ser Trp Leu Leu Leu Ser Leu Val Ala Val Thr Ala
1               5                   10                  15

Ala Gln Ser Thr Ile Glu Glu Gln Ala Lys Xaa Phe Leu Asp Lys Phe
                20                  25                  30

Asn Xaa Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
        50                  55                  60

Ala Gly Asp Lys Trp Ser Ala Phe Leu Lys Glu Gln Ser Thr Leu Ala
65              70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175
```

```
Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
            195                 200                 205

Val Asn Gly Val Asp Gly Tyr Asp Tyr Ser Arg Gly Gln Leu Ile Glu
            210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
            275                 280                 285

Pro Asn Ile Asp Val Thr Asp Ala Met Val Asp Gln Ala Trp Asp Ala
            290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Xaa Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
            450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
            530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590
```

```
Thr Trp Leu Lys Asp Gln Asn Lys Asn Ser Phe Val Gly Trp Ser Thr
            595                 600                 605

Asp Trp Ser Pro Tyr Ala Asp Ser Gly Gly Gly Ser Gly Gly Tyr
    610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His
                645                 650                 655

His His

<210> SEQ ID NO 23
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (27)..(27)
<223> OTHER INFORMATION: Xaa is Thr, Trp or Tyr
<220> FEATURE:
<221> NAME/KEY: misc_feature
<222> LOCATION: (34)..(34)
<223> OTHER INFORMATION: Xaa is His, Phe, or Trp
<220> FEATURE:
<221> NAME/KEY: DISULFID
<222> LOCATION: (275)..(448)
<220> FEATURE:
<221> NAME/KEY: misc_feature
<222> LOCATION: (353)..(353)
<223> OTHER INFORMATION: Xaa is Lys, Trp, or Tyr

<400> SEQUENCE: 23

Met Ser Ser Ser Trp Leu Leu Leu Ser Leu Val Ala Val Thr Ala
1               5                   10                  15

Ala Gln Ser Thr Ile Glu Glu Gln Ala Lys Xaa Phe Leu Asp Lys Phe
                20                  25                  30

Asn Xaa Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
```

```
                210                 215                 220
Asp Val Glu His Thr Phe Glu Ile Lys Pro Leu Tyr Glu His Leu
225                 230                 235                 240

His Ala Tyr Val Arg Ala Lys Leu Met Asn Ala Tyr Pro Ser Tyr Ile
                    245                 250                 255

Ser Pro Ile Gly Cys Leu Pro Ala His Leu Leu Gly Asp Met Trp Gly
                260                 265                 270

Arg Phe Cys Thr Asn Leu Tyr Ser Leu Thr Val Pro Phe Gly Gln Lys
            275                 280                 285

Pro Asn Ile Asp Val Thr Asp Ala Met Val Asp Gln Ala Trp Asp Ala
        290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                    325                 330                 335

Gly Asn Val Gln Lys Ala Val Cys His Pro Thr Ala Trp Asp Leu Gly
                340                 345                 350

Xaa Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
        370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                    405                 410                 415

His Leu Lys Ser Ile Gly Leu Leu Ser Pro Asp Phe Gln Glu Asp Asn
                420                 425                 430

Glu Thr Glu Ile Asn Phe Leu Leu Lys Gln Ala Leu Thr Ile Val Cys
            435                 440                 445

Thr Leu Pro Phe Thr Tyr Met Leu Glu Lys Trp Arg Trp Met Val Phe
        450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                    485                 490                 495

Tyr Cys Asp Pro Ala Ser Leu Phe His Val Ser Asn Tyr Ser Phe
                500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
        530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                    565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
            595                 600                 605

Asp Trp Ser Pro Tyr Ala Asp Ser Gly Gly Gly Ser Gly Gly Tyr
        610                 615                 620

Ile Pro Glu Ala Pro Arg Asp Gly Gln Ala Tyr Val Arg Lys Asp Gly
625                 630                 635                 640
```

Glu Trp Val Leu Leu Ser Thr Phe Leu Gly Gly Ser His His His His
                645                 650                 655

His His

<210> SEQ ID NO 24
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (27)..(27)
<223> OTHER INFORMATION: Xaa is Thr, Trp or Tyr
<220> FEATURE:
<221> NAME/KEY: misc_feature
<222> LOCATION: (34)..(34)
<223> OTHER INFORMATION: Xaa is His, Phe, or Trp
<220> FEATURE:
<221> NAME/KEY: misc_feature
<222> LOCATION: (353)..(353)
<223> OTHER INFORMATION: Xaa is Lys, Trp, or Tyr
<220> FEATURE:
<221> NAME/KEY: DISULFID
<222> LOCATION: (377)..(408)

<400> SEQUENCE: 24

Met Ser Ser Ser Ser Trp Leu Leu Leu Ser Leu Val Ala Val Thr Ala
1               5                   10                  15

Ala Gln Ser Thr Ile Glu Glu Gln Ala Lys Xaa Phe Leu Asp Lys Phe
            20                  25                  30

Asn Xaa Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

```
Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Xaa Gly Asp Phe Arg Ile Leu Met Cys Thr Lys Val Thr Met Asp Asp
        355                 360                 365

Phe Leu Thr Ala His His Glu Met Cys His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Cys Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Ser Gly Gly Gly Ser Gly Gly Tyr
610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His
                645                 650                 655

His His

<210> SEQ ID NO 25
```

```
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (27)..(27)
<223> OTHER INFORMATION: Xaa is Thr, Trp or Tyr
<220> FEATURE:
<221> NAME/KEY: misc_feature
<222> LOCATION: (34)..(34)
<223> OTHER INFORMATION: Xaa is His, Phe, or Trp
<220> FEATURE:
<221> NAME/KEY: misc_feature
<222> LOCATION: (353)..(353)
<223> OTHER INFORMATION: Xaa is Lys, Trp, or Tyr
<220> FEATURE:
<221> NAME/KEY: DISULFID
<222> LOCATION: (523)..(583)

<400> SEQUENCE: 25

Met Ser Ser Ser Ser Trp Leu Leu Leu Ser Leu Val Ala Val Thr Ala
1               5                   10                  15

Ala Gln Ser Thr Ile Glu Glu Gln Ala Lys Xaa Phe Leu Asp Lys Phe
            20                  25                  30

Asn Xaa Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
 50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300
```

Gln Arg Ile Phe Lys Glu Ala Glu Lys Phe Val Ser Val Gly Leu
305                 310                 315                 320

Pro Asn Met Thr Gln Gly Phe Trp Glu Asn Ser Met Leu Thr Asp Pro
            325                 330                 335

Gly Asn Val Gln Lys Ala Val Cys His Pro Thr Ala Trp Asp Leu Gly
            340                 345                 350

Xaa Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
        370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
            405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
            485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Cys Gln Phe Gln Glu Ala
        515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
            565                 570                 575

Lys Asn Met Asn Val Arg Cys Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Ser Gly Gly Gly Ser Gly Gly Tyr
610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His
            645                 650                 655

His His

<210> SEQ ID NO 26
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (27)..(27)

```
<223> OTHER INFORMATION: Xaa is Thr, Trp or Tyr
<220> FEATURE:
<221> NAME/KEY: misc_feature
<222> LOCATION: (34)..(34)
<223> OTHER INFORMATION: Xaa is His, Phe, or Trp
<220> FEATURE:
<221> NAME/KEY: misc_feature
<222> LOCATION: (353)..(353)
<223> OTHER INFORMATION: Xaa is Lys, Trp, or Tyr
<220> FEATURE:
<221> NAME/KEY: DISULFID
<222> LOCATION: (523)..(584)

<400> SEQUENCE: 26
```

| | | | | | | | | | | | | | | |
|---|---|---|---|---|---|---|---|---|---|---|---|---|---|---|
| Met | Ser | Ser | Ser | Ser | Trp | Leu | Leu | Ser | Leu | Val | Ala | Val | Thr | Ala |
| 1 | | | | 5 | | | | | 10 | | | | | 15 |
| Ala | Gln | Ser | Thr | Ile | Glu | Glu | Gln | Ala | Lys | Xaa | Phe | Leu | Asp | Lys | Phe |
| | | | 20 | | | | | 25 | | | | | 30 | | |
| Asn | Xaa | Glu | Ala | Glu | Asp | Leu | Phe | Tyr | Gln | Ser | Ser | Leu | Ala | Ser | Trp |
| | | 35 | | | | | 40 | | | | | 45 | | | |
| Asn | Tyr | Asn | Thr | Asn | Ile | Thr | Glu | Glu | Asn | Val | Gln | Asn | Met | Asn | Asn |
| 50 | | | | | 55 | | | | | 60 | | | | | |
| Ala | Gly | Asp | Lys | Trp | Ser | Ala | Phe | Leu | Lys | Glu | Gln | Ser | Thr | Leu | Ala |
| 65 | | | | | 70 | | | | | 75 | | | | | 80 |
| Gln | Met | Tyr | Pro | Leu | Gln | Glu | Ile | Gln | Asn | Leu | Thr | Val | Lys | Leu | Gln |
| | | | | 85 | | | | | 90 | | | | | 95 | |
| Leu | Gln | Ala | Leu | Gln | Gln | Asn | Gly | Ser | Ser | Val | Leu | Ser | Glu | Asp | Lys |
| | | | 100 | | | | | 105 | | | | | 110 | | |
| Ser | Lys | Arg | Leu | Asn | Thr | Ile | Leu | Asn | Thr | Met | Ser | Thr | Ile | Tyr | Ser |
| | | 115 | | | | | 120 | | | | | 125 | | | |
| Thr | Gly | Lys | Val | Cys | Asn | Pro | Asp | Asn | Pro | Gln | Glu | Cys | Leu | Leu | Leu |
| 130 | | | | | 135 | | | | | 140 | | | | | |
| Glu | Pro | Gly | Leu | Asn | Glu | Ile | Met | Ala | Asn | Ser | Leu | Asp | Tyr | Asn | Glu |
| 145 | | | | | 150 | | | | | 155 | | | | | 160 |
| Arg | Leu | Trp | Ala | Trp | Glu | Ser | Trp | Arg | Ser | Glu | Val | Gly | Lys | Gln | Leu |
| | | | | 165 | | | | | 170 | | | | | 175 | |
| Arg | Pro | Leu | Tyr | Glu | Glu | Tyr | Val | Val | Leu | Lys | Asn | Glu | Met | Ala | Arg |
| | | | 180 | | | | | 185 | | | | | 190 | | |
| Ala | Asn | His | Tyr | Glu | Asp | Tyr | Gly | Asp | Tyr | Trp | Arg | Gly | Asp | Tyr | Glu |
| | | 195 | | | | | 200 | | | | | 205 | | | |
| Val | Asn | Gly | Val | Asp | Gly | Tyr | Asp | Tyr | Ser | Arg | Gly | Gln | Leu | Ile | Glu |
| | 210 | | | | | 215 | | | | | 220 | | | | |
| Asp | Val | Glu | His | Thr | Phe | Glu | Glu | Ile | Lys | Pro | Leu | Tyr | Glu | His | Leu |
| 225 | | | | | 230 | | | | | 235 | | | | | 240 |
| His | Ala | Tyr | Val | Arg | Ala | Lys | Leu | Met | Asn | Ala | Tyr | Pro | Ser | Tyr | Ile |
| | | | | 245 | | | | | 250 | | | | | 255 | |
| Ser | Pro | Ile | Gly | Cys | Leu | Pro | Ala | His | Leu | Leu | Gly | Asp | Met | Trp | Gly |
| | | | 260 | | | | | 265 | | | | | 270 | | |
| Arg | Phe | Trp | Thr | Asn | Leu | Tyr | Ser | Leu | Thr | Val | Pro | Phe | Gly | Gln | Lys |
| | | 275 | | | | | 280 | | | | | 285 | | | |
| Pro | Asn | Ile | Asp | Val | Thr | Asp | Ala | Met | Val | Asp | Gln | Ala | Trp | Asp | Ala |
| | 290 | | | | | 295 | | | | | 300 | | | | |
| Gln | Arg | Ile | Phe | Lys | Glu | Ala | Glu | Lys | Phe | Phe | Val | Ser | Val | Gly | Leu |
| 305 | | | | | 310 | | | | | 315 | | | | | 320 |
| Pro | Asn | Met | Thr | Gln | Gly | Phe | Trp | Glu | Asn | Ser | Met | Leu | Thr | Asp | Pro |
| | | | | 325 | | | | | 330 | | | | | 335 | |
| Gly | Asn | Val | Gln | Lys | Ala | Val | Cys | His | Pro | Thr | Ala | Trp | Asp | Leu | Gly |

```
                    340                 345                 350
Xaa Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
    370                 375                 380

Tyr Ala Ala Gln Pro Phe Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Cys Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Cys Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Ser Gly Gly Gly Ser Gly Gly Tyr
    610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His
                645                 650                 655
His His

<210> SEQ ID NO 27
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (27)..(27)
<223> OTHER INFORMATION: Xaa is Thr, Trp or Tyr
<220> FEATURE:
<221> NAME/KEY: misc_feature
<222> LOCATION: (34)..(34)
<223> OTHER INFORMATION: Xaa is His, Phe, or Trp
<220> FEATURE:
<221> NAME/KEY: DISULFID
<222> LOCATION: (275)..(448)
```

```
<220> FEATURE:
<221> NAME/KEY: misc_feature
<222> LOCATION: (353)..(353)
<223> OTHER INFORMATION: Xaa is Lys, Trp, or Tyr
<220> FEATURE:
<221> NAME/KEY: DISULFID
<222> LOCATION: (377)..(408)

<400> SEQUENCE: 27
```

Met Ser Ser Ser Ser Trp Leu Leu Ser Leu Val Ala Val Thr Ala
1               5                   10                  15

Ala Gln Ser Thr Ile Glu Glu Gln Ala Lys Xaa Phe Leu Asp Lys Phe
            20                  25                  30

Asn Xaa Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Cys Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Xaa Gly Asp Phe Arg Ile Leu Met Cys Thr Lys Val Thr Met Asp Asp
        355                 360                 365

```
Phe Leu Thr Ala His His Glu Met Cys His Ile Gln Tyr Asp Met Ala
    370                 375                 380

Tyr Ala Ala Gln Pro Phe Leu Arg Asn Gly Ala Asn Glu Gly Phe
385                 390                 395                 400

His Glu Ala Val Gly Glu Ile Cys Ser Leu Ser Ala Ala Thr Pro Lys
                405                 410                 415

His Leu Lys Ser Ile Gly Leu Leu Ser Pro Asp Phe Gln Glu Asp Asn
                420                 425                 430

Glu Thr Glu Ile Asn Phe Leu Leu Lys Gln Ala Leu Thr Ile Val Cys
            435                 440                 445

Thr Leu Pro Phe Thr Tyr Met Leu Glu Lys Trp Arg Trp Met Val Phe
450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Phe Gln Phe Gln Glu Ala
            515                 520                 525

Leu Cys Gln Ala Ala Lys His Glu Gly Pro Leu His Lys Cys Asp Ile
530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
                580                 585                 590

Thr Trp Leu Lys Asp Gln Asn Lys Asn Ser Phe Val Gly Trp Ser Thr
            595                 600                 605

Asp Trp Ser Pro Tyr Ala Asp Ser Gly Gly Gly Ser Gly Gly Tyr
610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His His
                645                 650                 655

His His
```

<210> SEQ ID NO 28
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (27)..(27)
<223> OTHER INFORMATION: Xaa is Thr, Trp or Tyr
<220> FEATURE:
<221> NAME/KEY: misc_feature
<222> LOCATION: (34)..(34)
<223> OTHER INFORMATION: Xaa is His, Phe, or Trp
<220> FEATURE:
<221> NAME/KEY: DISULFID
<222> LOCATION: (275)..(448)
<220> FEATURE:
<221> NAME/KEY: misc_feature
<222> LOCATION: (353)..(353)
<223> OTHER INFORMATION: Xaa is Lys, Trp, or Tyr
<220> FEATURE:

<221> NAME/KEY: DISULFID
<222> LOCATION: (523)..(583)

<400> SEQUENCE: 28

```
Met Ser Ser Ser Trp Leu Leu Leu Ser Leu Val Ala Val Thr Ala
1               5                   10                  15

Ala Gln Ser Thr Ile Glu Glu Gln Ala Lys Xaa Phe Leu Asp Lys Phe
            20                  25                  30

Asn Xaa Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Cys Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Xaa Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400
```

```
His Glu Ala Val Gly Glu Ile Met Ser Leu Ser Ala Ala Thr Pro Lys
            405                 410                 415
His Leu Lys Ser Ile Gly Leu Leu Ser Pro Asp Phe Gln Glu Asp Asn
        420                 425                 430
Glu Thr Glu Ile Asn Phe Leu Leu Lys Gln Ala Leu Thr Ile Val Cys
    435                 440                 445
Thr Leu Pro Phe Thr Tyr Met Leu Glu Lys Trp Arg Trp Met Val Phe
450                 455                 460
Lys Gly Glu Ile Pro Lys Asp Gln Trp Met Lys Lys Trp Trp Glu Met
465                 470                 475                 480
Lys Arg Glu Ile Val Gly Val Val Glu Pro Val Pro His Asp Glu Thr
                485                 490                 495
Tyr Cys Asp Pro Ala Ser Leu Phe His Val Ser Asn Asp Tyr Ser Phe
            500                 505                 510
Ile Arg Tyr Tyr Thr Arg Thr Leu Tyr Gln Cys Gln Phe Gln Glu Ala
        515                 520                 525
Leu Cys Gln Ala Ala Lys His Glu Gly Pro Leu His Lys Cys Asp Ile
    530                 535                 540
Ser Asn Ser Thr Glu Ala Gly Gln Lys Leu Phe Asn Met Leu Arg Leu
545                 550                 555                 560
Gly Lys Ser Glu Pro Trp Thr Leu Ala Leu Glu Asn Val Val Gly Ala
                565                 570                 575
Lys Asn Met Asn Val Arg Cys Leu Leu Asn Tyr Phe Glu Pro Leu Phe
            580                 585                 590
Thr Trp Leu Lys Asp Gln Asn Lys Asn Ser Phe Val Gly Trp Ser Thr
        595                 600                 605
Asp Trp Ser Pro Tyr Ala Asp Ser Gly Gly Gly Ser Gly Gly Tyr
    610                 615                 620
Ile Pro Glu Ala Pro Arg Asp Gly Gln Ala Tyr Val Arg Lys Asp Gly
625                 630                 635                 640
Glu Trp Val Leu Leu Ser Thr Phe Leu Gly Gly Ser His His His His
                645                 650                 655
His His

<210> SEQ ID NO 29
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (27)..(27)
<223> OTHER INFORMATION: Xaa is Thr, Trp or Tyr
<220> FEATURE:
<221> NAME/KEY: misc_feature
<222> LOCATION: (34)..(34)
<223> OTHER INFORMATION: Xaa is His, Phe, or Trp
<220> FEATURE:
<221> NAME/KEY: DISULFID
<222> LOCATION: (275)..(448)
<220> FEATURE:
<221> NAME/KEY: misc_feature
<222> LOCATION: (353)..(353)
<223> OTHER INFORMATION: Xaa is Lys, Trp, or Tyr
<220> FEATURE:
<221> NAME/KEY: DISULFID
<222> LOCATION: (523)..(584)

<400> SEQUENCE: 29
```

```
Met Ser Ser Ser Ser Trp Leu Leu Leu Ser Leu Val Ala Val Thr Ala
1               5                   10                  15

Ala Gln Ser Thr Ile Glu Glu Gln Ala Lys Xaa Phe Leu Asp Lys Phe
            20                  25                  30

Asn Xaa Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
            115                 120                 125

Thr Gly Lys Val Cys Asn Pro Asp Asn Pro Gln Glu Cys Leu Leu Leu
            130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
            195                 200                 205

Val Asn Gly Val Asp Gly Tyr Asp Tyr Ser Arg Gly Gln Leu Ile Glu
            210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Cys Thr Asn Leu Tyr Ser Leu Thr Val Pro Phe Gly Gln Lys
            275                 280                 285

Pro Asn Ile Asp Val Thr Asp Ala Met Val Asp Gln Ala Trp Asp Ala
            290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Xaa Gly Asp Phe Arg Ile Leu Met Cys Thr Lys Val Thr Met Asp Asp
            355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
```

```
                420                 425                 430
Glu Thr Glu Ile Asn Phe Leu Leu Lys Gln Ala Leu Thr Ile Val Cys
            435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Cys Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Cys Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Ser Gly Gly Gly Ser Gly Gly Tyr
    610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His
                645                 650                 655

His His

<210> SEQ ID NO 30
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (27)..(27)
<223> OTHER INFORMATION: Xaa is Thr, Trp or Tyr
<220> FEATURE:
<221> NAME/KEY: misc_feature
<222> LOCATION: (34)..(34)
<223> OTHER INFORMATION: Xaa is His, Phe, or Trp
<220> FEATURE:
<221> NAME/KEY: misc_feature
<222> LOCATION: (353)..(353)
<223> OTHER INFORMATION: Xaa is Lys, Trp, or Tyr
<220> FEATURE:
<221> NAME/KEY: DISULFID
<222> LOCATION: (377)..(408)
<220> FEATURE:
<221> NAME/KEY: DISULFID
<222> LOCATION: (523)..(583)

<400> SEQUENCE: 30

Met Ser Ser Ser Ser Trp Leu Leu Leu Ser Leu Val Ala Val Thr Ala
1               5                   10                  15

Ala Gln Ser Thr Ile Glu Glu Gln Ala Lys Xaa Phe Leu Asp Lys Phe
                20                  25                  30
```

-continued

```
Asn Xaa Glu Ala Glu Asp Leu Phe Tyr Gln Ser Ser Leu Ala Ser Trp
    35                  40                  45

Asn Tyr Asn Thr Asn Ile Thr Glu Glu Asn Val Gln Asn Met Asn Asn
 50                  55                  60

Ala Gly Asp Lys Trp Ser Ala Phe Leu Lys Glu Gln Ser Thr Leu Ala
 65                  70                  75                  80

Gln Met Tyr Pro Leu Gln Glu Ile Gln Asn Leu Thr Val Lys Leu Gln
                 85                  90                  95

Leu Gln Ala Leu Gln Gln Asn Gly Ser Ser Val Leu Ser Glu Asp Lys
                100                 105                 110

Ser Lys Arg Leu Asn Thr Ile Leu Asn Thr Met Ser Thr Ile Tyr Ser
            115                 120                 125

Thr Gly Lys Val Cys Asn Pro Asp Asn Pro Gln Glu Cys Leu Leu Leu
130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Xaa Gly Asp Phe Arg Ile Leu Met Cys Thr Lys Val Thr Met Asp Asp
        355                 360                 365

Phe Leu Thr Ala His His Glu Met Cys His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Cys Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445
```

```
Thr Leu Pro Phe Thr Tyr Met Leu Glu Lys Trp Arg Trp Met Val Phe
        450                 455                 460
Lys Gly Glu Ile Pro Lys Asp Gln Trp Met Lys Lys Trp Trp Glu Met
465                 470                 475                 480
Lys Arg Glu Ile Val Gly Val Val Glu Pro Val Pro His Asp Glu Thr
                485                 490                 495
Tyr Cys Asp Pro Ala Ser Leu Phe His Val Ser Asn Asp Tyr Ser Phe
            500                 505                 510
Ile Arg Tyr Tyr Thr Arg Thr Leu Tyr Gln Cys Gln Phe Gln Glu Ala
        515                 520                 525
Leu Cys Gln Ala Ala Lys His Glu Gly Pro Leu His Lys Cys Asp Ile
530                 535                 540
Ser Asn Ser Thr Glu Ala Gly Gln Lys Leu Phe Asn Met Leu Arg Leu
545                 550                 555                 560
Gly Lys Ser Glu Pro Trp Thr Leu Ala Leu Glu Asn Val Val Gly Ala
                565                 570                 575
Lys Asn Met Asn Val Arg Cys Leu Leu Asn Tyr Phe Glu Pro Leu Phe
            580                 585                 590
Thr Trp Leu Lys Asp Gln Asn Lys Asn Ser Phe Val Gly Trp Ser Thr
        595                 600                 605
Asp Trp Ser Pro Tyr Ala Asp Ser Gly Gly Gly Ser Gly Gly Tyr
610                 615                 620
Ile Pro Glu Ala Pro Arg Asp Gly Gln Ala Tyr Val Arg Lys Asp Gly
625                 630                 635                 640
Glu Trp Val Leu Leu Ser Thr Phe Leu Gly Gly Ser His His His His
                645                 650                 655
His His

<210> SEQ ID NO 31
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (27)..(27)
<223> OTHER INFORMATION: Xaa is Thr, Trp or Tyr
<220> FEATURE:
<221> NAME/KEY: misc_feature
<222> LOCATION: (34)..(34)
<223> OTHER INFORMATION: Xaa is His, Phe, or Trp
<220> FEATURE:
<221> NAME/KEY: misc_feature
<222> LOCATION: (353)..(353)
<223> OTHER INFORMATION: Xaa is Lys, Trp, or Tyr
<220> FEATURE:
<221> NAME/KEY: DISULFID
<222> LOCATION: (377)..(408)
<220> FEATURE:
<221> NAME/KEY: DISULFID
<222> LOCATION: (523)..(584)

<400> SEQUENCE: 31

Met Ser Ser Ser Trp Leu Leu Ser Leu Val Ala Val Thr Ala
1               5                   10                  15
Ala Gln Ser Thr Ile Glu Glu Gln Ala Lys Xaa Phe Leu Asp Lys Phe
                20                  25                  30
Asn Xaa Glu Ala Glu Asp Leu Phe Tyr Gln Ser Ser Leu Ala Ser Trp
            35                  40                  45
Asn Tyr Asn Thr Asn Ile Thr Glu Glu Asn Val Gln Asn Met Asn Asn
```

```
            50                  55                  60
Ala Gly Asp Lys Trp Ser Ala Phe Leu Lys Glu Gln Ser Thr Leu Ala
 65                  70                  75                  80

Gln Met Tyr Pro Leu Gln Glu Ile Gln Asn Leu Thr Val Lys Leu Gln
                     85                  90                  95

Leu Gln Ala Leu Gln Gln Asn Gly Ser Ser Val Leu Ser Glu Asp Lys
                100                 105                 110

Ser Lys Arg Leu Asn Thr Ile Leu Asn Thr Met Ser Thr Ile Tyr Ser
            115                 120                 125

Thr Gly Lys Val Cys Asn Pro Asp Asn Pro Gln Glu Cys Leu Leu Leu
        130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
                180                 185                 190

Ala Asn His Tyr Glu Asp Tyr Gly Asp Tyr Trp Arg Gly Asp Tyr Glu
            195                 200                 205

Val Asn Gly Val Asp Gly Tyr Asp Tyr Ser Arg Gly Gln Leu Ile Glu
        210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
                260                 265                 270

Arg Phe Trp Thr Asn Leu Tyr Ser Leu Thr Val Pro Phe Gly Gln Lys
            275                 280                 285

Pro Asn Ile Asp Val Thr Asp Ala Met Val Asp Gln Ala Trp Asp Ala
        290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Xaa Gly Asp Phe Arg Ile Leu Met Cys Thr Lys Val Thr Met Asp Asp
        355                 360                 365

Phe Leu Thr Ala His His Glu Met Cys His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Cys Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
        450                 455                 460

Lys Gly Glu Ile Pro Lys Asp Gln Trp Met Lys Lys Trp Trp Glu Met
465                 470                 475                 480
```

-continued

```
Lys Arg Glu Ile Val Gly Val Glu Pro Val His Asp Glu Thr
                485             490             495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Cys Gln Phe Gln Glu Ala
                515                 520                 525

Leu Cys Gln Ala Ala Lys His Glu Gly Pro Leu His Lys Cys Asp Ile
            530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Cys Leu Asn Tyr Phe Glu Pro Leu Phe
                580                 585                 590

Thr Trp Leu Lys Asp Gln Asn Lys Asn Ser Phe Val Gly Trp Ser Thr
                595                 600                 605

Asp Trp Ser Pro Tyr Ala Asp Ser Gly Gly Gly Ser Gly Gly Tyr
                610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His His
                645                 650                 655

His His

<210> SEQ ID NO 32
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (27)..(27)
<223> OTHER INFORMATION: Xaa is Thr, Trp or Tyr
<220> FEATURE:
<221> NAME/KEY: misc_feature
<222> LOCATION: (34)..(34)
<223> OTHER INFORMATION: Xaa is His, Phe, or Trp
<220> FEATURE:
<221> NAME/KEY: DISULFID
<222> LOCATION: (275)..(448)
<220> FEATURE:
<221> NAME/KEY: misc_feature
<222> LOCATION: (353)..(353)
<223> OTHER INFORMATION: Xaa is Lys, Trp, or Tyr
<220> FEATURE:
<221> NAME/KEY: DISULFID
<222> LOCATION: (377)..(408)
<220> FEATURE:
<221> NAME/KEY: DISULFID
<222> LOCATION: (523)..(583)

<400> SEQUENCE: 32

Met Ser Ser Ser Ser Trp Leu Leu Leu Ser Leu Val Ala Val Thr Ala
1               5                   10                  15

Ala Gln Ser Thr Ile Glu Glu Gln Ala Lys Xaa Phe Leu Asp Lys Phe
                20                  25                  30

Asn Xaa Glu Ala Glu Asp Leu Phe Tyr Gln Ser Ser Leu Ala Ser Trp
            35                  40                  45

Asn Tyr Asn Thr Asn Ile Thr Glu Glu Asn Val Gln Asn Met Asn Asn
    50                  55                  60
```

```
Ala Gly Asp Lys Trp Ser Ala Phe Leu Lys Glu Gln Ser Thr Leu Ala
 65                  70                  75                  80

Gln Met Tyr Pro Leu Gln Glu Ile Gln Asn Leu Thr Val Lys Leu Gln
                 85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Cys Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Xaa Gly Asp Phe Arg Ile Leu Met Cys Thr Lys Val Thr Met Asp Asp
        355                 360                 365

Phe Leu Thr Ala His His Glu Met Cys His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Cys Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Cys
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
```

```
                485                 490                 495
Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Cys Gln Phe Gln Glu Ala
            515                 520                 525

Leu Cys Gln Ala Ala Lys His Glu Gly Pro Leu His Lys Cys Asp Ile
            530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Cys Leu Leu Asn Tyr Phe Glu Pro Leu Phe
            580                 585                 590

Thr Trp Leu Lys Asp Gln Asn Lys Asn Ser Phe Val Gly Trp Ser Thr
            595                 600                 605

Asp Trp Ser Pro Tyr Ala Asp Ser Gly Gly Gly Ser Gly Gly Tyr
            610                 615                 620

Ile Pro Glu Ala Pro Arg Asp Gly Gln Ala Tyr Val Arg Lys Asp Gly
625                 630                 635                 640

Glu Trp Val Leu Leu Ser Thr Phe Leu Gly Gly Ser His His His His
                645                 650                 655

His His

<210> SEQ ID NO 33
<211> LENGTH: 658
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (27)..(27)
<223> OTHER INFORMATION: Xaa is Thr, Trp or Tyr
<220> FEATURE:
<221> NAME/KEY: misc_feature
<222> LOCATION: (34)..(34)
<223> OTHER INFORMATION: Xaa is His, Phe, or Trp
<220> FEATURE:
<221> NAME/KEY: DISULFID
<222> LOCATION: (275)..(448)
<220> FEATURE:
<221> NAME/KEY: misc_feature
<222> LOCATION: (353)..(353)
<223> OTHER INFORMATION: Xaa is Lys, Trp, or Tyr
<220> FEATURE:
<221> NAME/KEY: DISULFID
<222> LOCATION: (377)..(408)
<220> FEATURE:
<221> NAME/KEY: DISULFID
<222> LOCATION: (523)..(584)

<400> SEQUENCE: 33

Met Ser Ser Ser Trp Leu Leu Leu Ser Leu Val Ala Val Thr Ala
1               5                   10                  15

Ala Gln Ser Thr Ile Glu Glu Gln Ala Lys Xaa Phe Leu Asp Lys Phe
            20                  25                  30

Asn Xaa Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80
```

```
Gln Met Tyr Pro Leu Gln Glu Ile Gln Asn Leu Thr Val Lys Leu Gln
                 85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Cys Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Xaa Gly Asp Phe Arg Ile Leu Met Cys Thr Lys Val Thr Met Asp Asp
        355                 360                 365

Phe Leu Thr Ala His His Glu Met Cys His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Cys Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Cys
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495
```

-continued

```
Tyr Cys Asp Pro Ala Ser Leu Phe His Val Ser Asn Asp Tyr Ser Phe
        500                 505                 510
Ile Arg Tyr Tyr Thr Arg Thr Leu Tyr Gln Cys Gln Phe Gln Glu Ala
        515                 520                 525
Leu Cys Gln Ala Ala Lys His Glu Gly Pro Leu His Lys Cys Asp Ile
        530                 535                 540
Ser Asn Ser Thr Glu Ala Gly Gln Lys Leu Phe Asn Met Leu Arg Leu
545                 550                 555                 560
Gly Lys Ser Glu Pro Trp Thr Leu Ala Leu Glu Asn Val Val Gly Ala
                565                 570                 575
Lys Asn Met Asn Val Arg Pro Cys Leu Asn Tyr Phe Glu Pro Leu Phe
            580                 585                 590
Thr Trp Leu Lys Asp Gln Asn Lys Asn Ser Phe Val Gly Trp Ser Thr
        595                 600                 605
Asp Trp Ser Pro Tyr Ala Asp Ser Gly Gly Gly Gly Ser Gly Gly Tyr
        610                 615                 620
Ile Pro Glu Ala Pro Arg Asp Gly Gln Ala Tyr Val Arg Lys Asp Gly
625                 630                 635                 640
Glu Trp Val Leu Leu Ser Thr Phe Leu Gly Gly Ser His His His His
                645                 650                 655
His His
```

HIGH-AFFINITY HUMAN ACE2 CONSTRUCT FOR USE IN DIAGNOSING AND TREATING CORONAVIRUSES

RELATED APPLICATIONS

This application claims priority under 35 U.S.C. § 119(e) to U.S. Patent Application Ser. No. 63/027,304, filed May 19, 2020, and titled "A HIGH-AFFINITY HUMAN ACE2 CONSTRUCT FOR USE IN DIAGNOSING AND TREATING CORONAVIRUSES" and U.S. Patent Application Ser. No. 63/080,573, filed Sep. 18, 2020, and titled "A HIGH-AFFINITY HUMAN ACE2 CONSTRUCT FOR USE IN DIAGNOSING AND TREATING CORONAVIRUSES", the contents of both of which are incorporated herein in their entirety.

SEQUENCE LISTING

The instant application contains a Sequence Listing which has been submitted in ASCII format via EFS-Web and is hereby incorporated by reference in its entirety. Said ASCII copy, created on Aug. 18, 2021, is named C123370184US02-SEQ-AZW and is 188,070 bytes in size.

BACKGROUND

The SARS-CoV-2 pandemic has highlighted the need for diagnostics, therapeutics, and vaccines to effectively manage coronavirus outbreaks, as well as other viruses that take advantage of binding to the Angiotensin-converting enzyme 2 (ACE2) cellular receptor. Viral membrane fusion is the first key step for enveloped viruses, including SARS-CoV-2, to enter host cells and establish infection. The spike (S) protein of CoV catalyzes the membrane fusion reaction and it is also a major surface antigen that induces neutralizing antibodies. The S protein has been an important target for development of both vaccines and therapeutics. It is a heavily glycosylated type I membrane protein sitting in the viral membrane and undergoes large structural rearrangements required for promoting membrane fusion. However, production of high-quality, intact viral fusion proteins has been challenging. Therefore, there is a need to develop compositions, methods, and systems to effectively diagnose, prevent, and treat coronavirus infections, as well as other viral infections that take advantage of binding to the ACE2 cellular receptor.

SUMMARY

The present invention relates to compositions, methods, and systems of using constructs of the ACE2 cellular receptor to detect or treat virus infections, including coronavirus infections like SARS-CoV-2. ACE2 is a cellular receptor for coronaviruses like SARS-CoV and SARS-CoV-2. ACE2 binds the S proteins of SARS-CoV and SARS-CoV-2.

Accordingly, in some embodiments, the present disclosure provides an isolated polypeptide monomer comprising an ACE2 ectodomain and an oligomerization domain. In some embodiments, the oligomerization domain provides for the trimerization of the polypeptide monomers. In some embodiments, the oligomerization domain comprises a foldon trimerization tag. In some embodiments, the oligomerization domain provides for the tetramerization of the polypeptide monomers. In some embodiments, the oligomerization domain comprises a streptavidin domain.

Aspects of the present disclosure provide oligomeric complexes comprising two or more polypeptide monomers comprising an ACE2 ectodomain and an oligomerization domain, wherein at least two monomers are associated with each other. In some embodiments, the oligomeric complexes comprise three polypeptide monomers comprising an ACE2 ectodomain and an oligomerization domain, wherein at least two monomers are associated with each other. In some embodiments, the oligomeric complex comprises four polypeptide monomers comprising an ACE2 ectodomain and an oligomerization domain, wherein at least two monomers are associated with each other.

In some embodiments, the ACE2 ectodomains of the polypeptide monomers comprise a stabilizing mutation, wherein the mutation increases the stability of the polypeptide monomer when associated with at least one polypeptide monomer. In some embodiments, the oligomeric complexes comprise polypeptide monomers with ACE2 ectodomains that comprise a stabilizing mutation, wherein the mutation increases the stability of the polypeptide monomer when associated with at least one polypeptide monomer.

In some embodiments, the ACE2 ectodomains of the polypeptide monomers comprise a mutation that decreases the off-rate of the interaction with the S protein. In some embodiments, the oligomeric complexes comprise polypeptide monomers with ACE2 ectodomains that comprise a mutation that decreases the off-rate of the interaction with the S protein.

In some embodiments, the polypeptides have at least 75% sequence homology to any of the sequences of SEQ ID NOs:2-3.

Aspects of the present disclosure provide nucleic acid molecules encoding polypeptide monomers comprising an ACE2 ectodomain and an oligomerization domain. Other aspects of the present disclosure provide vectors expressing nucleic acid molecules encoding polypeptide monomers comprising an ACE2 ectodomain and an oligomerization domain. Other aspects of the present disclosure provide kits comprising polypeptide monomers comprising an ACE2 ectodomain and an oligomerization domain or oligomeric complexes comprising such polypeptide monomers.

Aspects of the present disclosure provide methods for the determination of the presence of SARS-CoV-2 in a sample, the method comprising the steps of allowing the sample to contact a diagnostically effective amount of a binding molecule comprising a polypeptide monomer comprising an ACE2 ectodomain and an oligomerization domain, or the oligomeric complex of said polypeptide monomers, under conditions that allow the binding molecule to bind at least one SARS-CoV-2 S protein; and detecting whether the binding molecule specifically binds to a molecule of the sample. In some embodiments, the binding is detected using gold particles. In other embodiments, the binding occurs in a lateral flow test kit.

Aspects of the present disclosure provide methods for the determination of a SARS-CoV-2 virus infection in a patient, said method comprising the steps of allowing the sample to contact a diagnostically effective amount of a binding molecule comprising an ACE2 ectodomain and an oligomerization domain, or the oligomeric complex of said polypeptide monomers, under conditions that allow the binding molecule to bind to at least one SARS-CoV-2 S protein; and detecting whether the binding molecule specifically binds to a molecule of the sample. In some embodiments, the binding is detected using gold particles. In other embodiments, the binding occurs in a lateral flow test kit.

Aspects of the present disclosure provide methods for treating a patient in need thereof, said method comprising the steps of administering a therapeutically effective amount of a polypeptide monomer of an ACE2 ectodomain and an oligomerization domain, a binding molecule comprising an ACE2 ectodomain and an oligomerization domain, or an oligomeric complex of said polypeptide monomers.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A is a schematic representation of the expression construct of the soluble SARS-CoV-2 S protein. Segments of S1 and S2 ectodomain (S2ecto) include: NTD, N-terminal domain; RBD, receptor-binding domain; S1/S2, S1/S2 cleavage site; S2', S2' cleavage site; FP (F), fusion peptide; HR1, heptad repeat 1; PP mutation, two proline residues introduced to stabilize the pre-fusion conformation; CH, central helix region; HR2, heptad repeat 2; foldon trimerization tag and a His tag; and tree-like symbols for glycans. The S1/S2 cleavage site (RRAR) was mutated to GGSG. The two proline residue mutations, K986P and V987P, were introduced and the trimerization tag—foldon was fused to the C-terminal end to stabilize the prefusion conformation. A C-terminal his tag was included for protein purification. FIG. 1B shows the purified S ectodomain trimer resolved by gel-filtration chromatography. Fractions of the peak were analyzed by Coomassie stained SDS-PAGE (inset). FIG. 1C shows negative stain EM of the S trimer showing representative 2D class averages, box size 220 Å. FIG. 1D shows a 3D reconstruction showing the defined shape of S trimer, superimposed with the atomic model of S trimer (PDB: 6VSB).

FIG. 2A shows His-tagged ACE2 resolved by gel-filtration chromatography. The peak fractions were analyzed by Coomassie stained SDS-PAGE (inset). FIG. 2B shows binding of ACE2 to the soluble S trimer (FIGS. 1A-1D) analyzed by SPR single-cycle kinetic analysis. FIG. 2C shows negative stain EM of the ACE2-S complex showing representative 2D class averages (left), and a 3D reconstruction superimposed with the atomic models of S trimer and ACE2 (right).

FIGS. 3A-3B show results of single cycle (FIG. 3A) and multi cycle (FIG. 3B) kinetic analysis for various concentrations of monomeric ACE2 passed over immobilized SARS-CoV-2 S trimer. The recorded sensorgram and fit are shown. FIG. 3C shows results of single cycle kinetic analysis for various concentrations of trimeric S protein passed over immobilized ACE2 monomer.

FIG. 5A-5B shows production of soluble trimeric ACE2. FIG. 5A shows His-tagged ACE2-foldon protein resolved by gel-filtration chromatography. The peak fractions were analyzed by Coomassie stained SDS-PAGE (inset). FIG. 5B shows binding of ACE2 trimer to S trimer analyzed by a surface plasmon resonance (SPR) assay.

FIG. 6 is an illustration of a lateral flow test.

FIG. 7A shows structure of the S trimer without ACE2 in a conformation with one RBD up was modeled based on a 3.6 Å density map. FIGS. 7B-7D show the structures of the S trimer in complex with one ACE2 (3.6 Å), two ACE2 (3.7 Å) and three ACE2 (3.4 Å), respectively.

FIGS. 8A-8C show design and characterization of ACE2 variants. FIG. 8A shows schematic representation of the full-length human ACE2. Various segments include: catalytic peptidase domain, neck domain; TM, transmembrane anchor; CT, cytoplasmic tail; and tree-like symbols for glycans. Expression constructs of various forms of ACE2 used in this study: ACE2615, an inactive peptidase domain with mutations at the active site (H374N and H378N) fused with a C-terminal histag via a flexible linker; ACE2m615-Fc, the peptidase domain fused to a Fc fragment of an immunoglobulin G at the C-terminus; ACE2740-Fc, the peptidase and neck domains fused to a Fc fragment at the C-terminus; ACE2615-foldon, the peptidase domain fused to a trimerization tag-foldon, followed by a C-terminal histag; ACE2615-foldon mutants, single mutations (T27Y, T27W, H34W, K353Y and K353W) were introduced in the context of ACE2615-foldon construct. FIG. 8B shows binding of ACE2 variants to the stabilized soluble S trimer by bio-layer interferometry (BLI). The S protein was immobilized to AR2G biosensors, which were dipped into the wells containing ACE2 at various concentrations (1.852-150 nM for ACE2615, 0.926-75 nM for ACE2740-Fc and 0.617-50 nM for all the ACE2615-foldon variants). Binding kinetics was evaluated using a 1:1 Langmuir binding model for the monomeric ACE2615 and a bivalent model for all other oligomeric ACE2. The sensorgrams are in black and the fits in grey. All experiments were repeated at least twice with essentially identical results. FIG. 8C shows summary of binding constants derived from the BLI experiments.

FIG. 9A shows peptidase activity of the ACE2 variants were measured by detecting free fluorophore released from a synthetic peptide substrate. A time-course experiment was performed and specific activity was calculated. The experiment has been repeated twice with similar results. FIG. 9B shows Ang II peptide was treated with various ACE2 variants before adding to the cells expressing Ang II receptor type 1 (AT1R) at different concentrations. AT1R activation was quantified by changes in the intracellular calcium concentration. Samples quenched at time 0 were used as controls. The y-axis is Ratio (Max–Min) (Peak fluorescent intensity–baseline fluorescent intensity). The EC50 values were also summarized.

FIG. 10A shows serial dilutions of each ACE2 variant were tested for inhibition against an MLV-based pseudotyped virus using a SARS-CoV-2 S construct containing D614 and a CT deletion in a single-round infection of HEK293-ACE2 cells. IC50 values were derived from curve fitting. The experiments were repeated three times with similar results. FIG. 10B shows ACE2 variants were tested for inhibition against an HIV-based pseudotyped virus using a full-length SARS-CoV-2 S construct containing G614 in a single-round infection of HEK293-ACE2 cells. IC50 values were derived from curve fitting. The experiments were repeated twice with similar results.

FIG. 10C show serial dilutions of each ACE2 variant were tested for inhibition against an authentic SARS-CoV-2 S virus (isolate USA-WA1/2020) infecting Vero E6 cells. IC50 values were derived from curve fitting. The experiments were repeated three times with similar results.

FIG. 12A shows 3D reconstructions of the S trimer and its ACE2 complexes are colored according to local resolution estimated by RELION. Angular distribution of the cryo-EM particles used in the reconstruction is shown in the side view of the EM map. FIG. 12B shows gold standard FSC curves of the refined 3D reconstructions. FIG. 12C shows representative density in gray surface from the EM maps. No ACE2), the free S trimer; 1 ACE2, S trimer with one ACE2 bound; 2 ACE2, S trimer with two ACE2 bound; 3 ACE2, S trimer with three ACE2 bound.

FIG. 13A shows the top view of the S trimer in complex with two monomeric ACE2 molecules (in magenta and cyan, respectively) with the distance between the C-terminal ends of the ACE2s indicated. FIG. 13B shows top view of the S trimer in complex with three monomeric ACE2 molecules with the distances between the C-terminal ends of the ACE2s indicated. FIG. 13C shows superposition of the structure of the full-length ACE2 (PDB ID:6M17) and the structure of S-3 ACE2 complex.

FIG. 17A shows the purified ACE2615-foldon protein either from cell supernatants (secreted) or cell lysates (cellular) was resolved by gel-filtration chromatography on a Superdex 200 column. Inset, peak fractions were analyzed by Coomassie stained SDS-PAGE. FIG. 17B shows binding of ACE2615-foldon to the stabilized soluble S trimer by bio-layer interferometry (BLI). The S protein was immobilized and subsequently dipped into the wells containing either secreted or cellular ACE2615-foldon at various concentrations (0.617-50 nM). The sensorgrams for the secreted ACE2615-foldon are in black and those for the cellular ACE2615-foldon in grey and marked with an asterisk.

DETAILED DESCRIPTION OF CERTAIN EMBODIMENTS

Figure 1A:
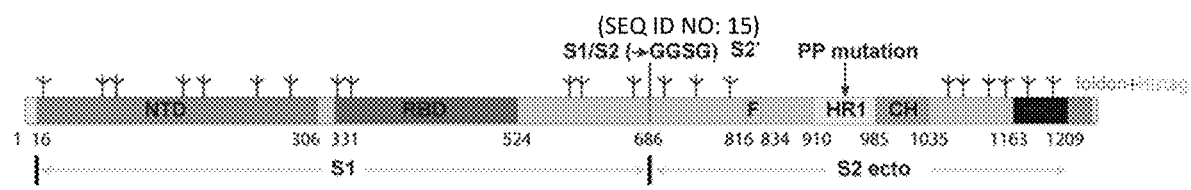
FIGS. 1A-1D show production of a stabilized soluble SARS-CoV-2 S ectodomain trimer in the pre-fusion conformation.

Provided herein, in some aspects, are polypeptides and oligomeric complexes for use in diagnostics, therapeutics, or prophylactics directed to viral infections such as coronaviruses, including the SARS-CoV-2 virion. The disclosure provides compositions based on monomers of the ACE2 ectodomain and an oligomerization domain, which allow either the trimerization, tetramerization, or other oligomerization states of ACE2. The present invention is based in part on the discovery that oligomerization of ACE2 allowed binding of the spike (S) protein from the virion with increased avidity. The increase in avidity allows for slower dissociation, which improves the binding properties, and thereby enhances the ability of the ACE2 oligomers to act as diagnostic, therapeutic, or prophylactic tools. Based on these results, compositions and methods for producing and using ACE2 oligomers are provided.

The terms "polypeptide" and "protein" are used interchangeably to refer to a polymer of amino acid residues linked by peptide bonds, and for the purposes of the instant disclosure, have a minimum length of at least 5 amino acids. Both full-length proteins and fragments thereof greater than 5 amino acids are encompassed by the definition. The terms also include polypeptides that have co-translational (e.g., signal peptide cleavage) and post-translational modifications of the polypeptide, such as, for example, disulfide-bond formation, glycosylation, acetylation, phosphorylation, proteolytic cleavage (e.g., cleavage by furins or metalloproteases), and the like. Furthermore, as used herein, a "polypeptide" or "protein" refers to a protein that includes modifications, such as deletions, additions, and substitutions (generally conservative in nature as would be known to a person in the art) to the native sequence, as long as the protein maintains the desired activity relevant to the purposes of the described methods. These modifications can be deliberate, as through site-directed mutagenesis, or can be accidental, such as through mutations of hosts that produce the proteins, or errors due to PCR amplification or other recombinant DNA methods.

As used herein, the term "oligomer," when used in the context of a protein and/or polypeptide is intended to include, but is not limited to, a protein or polypeptide having at least two subunits. Oligomers include, but are not limited to, dimers, trimers, tetramers, pentamers, hexamers, heptamers, octamers, nonamers, decamers and the like.

As used herein, the term "oligomerization domain" refers to, but is not limited to, a polypeptide sequence that can be used to increase the stability of an oligomeric protein such as, e.g., to increase the stability of an ACE2 trimer or tetramer. Oligomerization domains may increase the stability of dimers, trimers, tetramers, pentamers, hexamers, heptamers, octamers, nonamers, decamers and larger oligomers.

In certain aspects, oligomerization domains increase the stability of trimers. Oligomerization domains can be used to increase the stability of homooligomeric polypeptides as well as heterooligomeric polypeptides. Oligomerization domains are well known in the art. Examples of oligomerization domains include, but are not limited to, the T4-fibritin "foldon" trimer and streptavidin.

As used herein, the terms "bind," "binding," "interact," and "interacting" refer to covalent interactions, noncovalent interactions and steric interactions. A covalent interaction is a chemical linkage between two atoms or radicals formed by the sharing of a pair of electrons (a single bond), two pairs of electrons (a double bond) or three pairs of electrons (a triple bond). Covalent interactions are also known in the art as electron pair interactions or electron pair bonds. Noncovalent interactions include, but are not limited to, van der Waals interactions, hydrogen bonds, weak chemical bonds (via short-range noncovalent forces), hydrophobic interactions, ionic bonds and the like. A review of noncovalent interactions can be found in Alberts et al., in Molecular Biology of the Cell, 3d edition, Garland Publishing, 1994. Steric interactions are generally understood to include those where the structure of the compound is such that it is capable of occupying a site by virtue of its three dimensional structure, as opposed to any attractive forces between the compound and the site.

The terms "subject," and "patient," are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, camels, etc. In some embodiments, the mammal is human.

In some embodiments, a sample is obtained from the subject or patient. Such samples include biological fluids or biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). Biological tissues may be processed to obtain cell suspension samples. The sample may also be a mixture of cells prepared in vitro. The sample may also be a cultured cell suspension. In case of the biological samples, the sample may be crude samples or processed samples that are obtained after various processing or preparation on the original samples. For example, various cell separation methods (e.g., magnetically activated cell sorting) may be applied to separate or enrich target cells from a body fluid sample such as blood.

Biological fluids or biological tissue can be collected using any of the standard methods known in the art. Obtaining a plasma sample from a subject means taking possession of a plasma sample of the subject. In some embodiments, the plasma sample may be removed from the subject by a medical practitioner (e.g., a doctor, nurse, or a clinical laboratory practitioner), and then provided to the person performing the measuring steps of the assay described herein. The plasma sample may be provided to the person performing the measuring steps by the subject or by a medical practitioner (e.g., a doctor, nurse, or a clinical laboratory practitioner). In some embodiments, the person performing the measuring steps obtains a plasma sample from the subject by removing a blood sample from the subject and isolating plasma from the blood sample.

A "diagnostically effective amount" of the compositions of the disclosure generally refers to an amount sufficient to detect the desired biological composition, e.g., detect the virion or a viral infection. Similarly, a "therapeutically effective amount" of the compositions of the disclosure generally refers to an amount sufficient to elicit the desired biological response, e.g., treat the condition. As will be appreciated by those of ordinary skill in this art, the effective amount as described herein may vary depending on such factors as the virus being detected, the method of detection, the condition being treated, the mode of administration, and the age, body composition, and health of the subject.

The terms "treat", "treating", "treatment", and "therapy" encompass an action that occurs while a subject is suffering from a condition which reduces the severity of the condition (or a symptom associated with the condition) or retards or slows the progression of the condition (or a symptom associated with the condition).

In certain exemplary embodiments, vectors such as, for example, expression vectors, containing a nucleic acid encoding one or more ACE2 monomers described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably.

Techniques for determining nucleic acid and amino acid "sequence identity" are known in the art. Typically, such techniques include determining the nucleotide sequence of genomic DNA, mRNA or cDNA made from an mRNA for a gene and/or determining the amino acid sequence that it encodes, and comparing one or both of these sequences to a second nucleotide or amino acid sequence, as appropriate. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention.

EXAMPLES

The invention now being generally described, it will be more readily understood by reference to the following examples, which are included merely for purposes of illustration of certain embodiments and embodiments of the present invention, and are not intended to limit the invention.

Example 1. Production of the Full-Length Soluble Coronavirus Spike (S) Protein and ACE2 Receptor ACE2 is a cellular receptor for SARS-CoV and SARS-CoV-2 with optimal binding properties to the spike (S) protein on the virion surface. Constructs of the SARS-CoV-2 S protein have been expressed and purified, including the full-length version, to support structural studies and vaccine development. Provided herein is a procedure to design and produce ACE2 proteins with improved binding properties to SARS-CoV-2 S protein trimer.

Production and Characterization of the Stabilized SARS-CoV-2 S Ectodomain

Figure 1B:
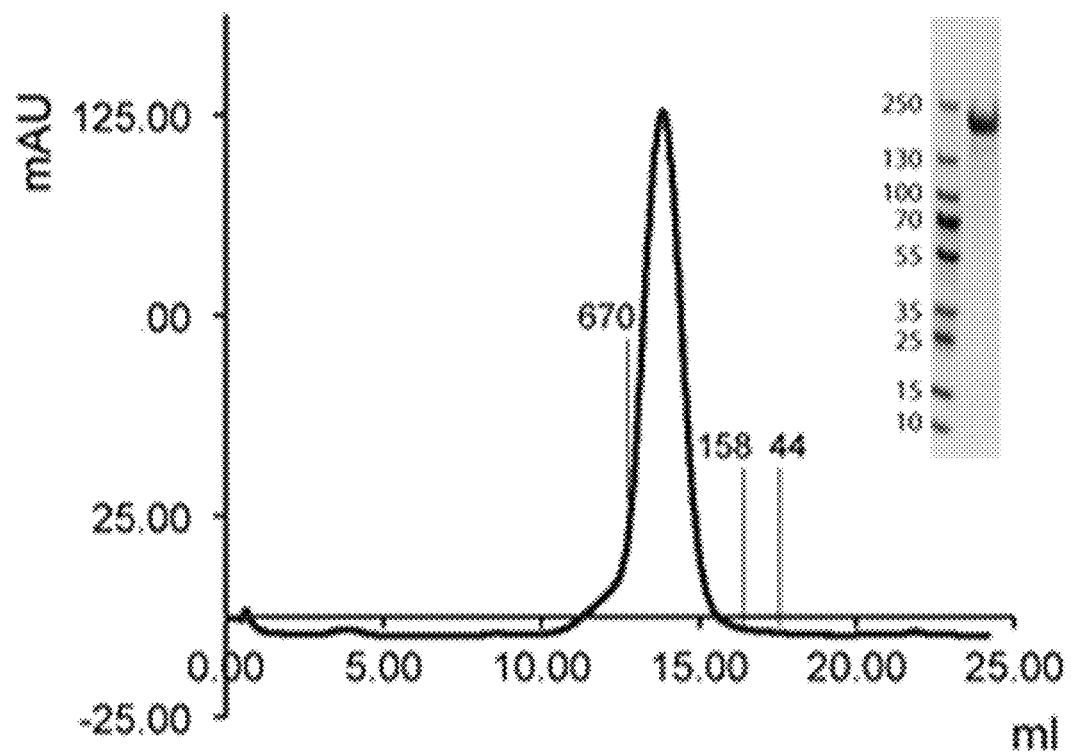
Figure 1C:
Figure 1D:
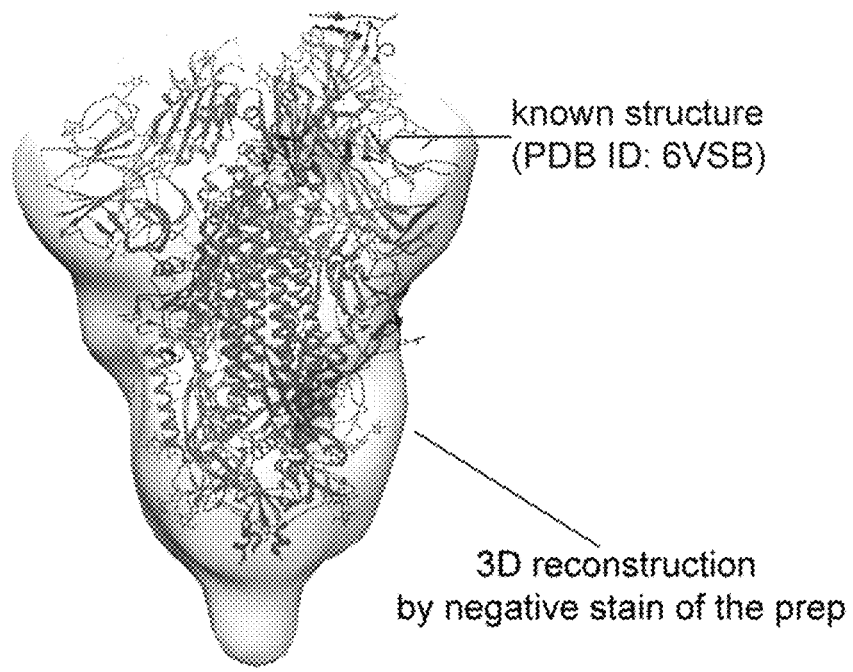

A stabilized S ectodomain trimer in the pre-fusion conformation was produced as described below. The construct was designed as shown in FIG. 1A. The purified S ectodomain trimer was resolved by gel-filtration chromatography (FIG. 1B) and the peak fractions were analyzed by Coomassie stained SDS-PAGE (FIG. 1B, inset). These results indicated that the preparation was stable and homogeneous. Negative stain EM of the S protein trimer was also performed. Representative 2D class averages are shown in FIG. 1C. A 3D reconstruction showing the defined shape of S trimer was prepared and superimposed with the atomic model of S trimer (PDB: 6VSB) (FIG. 1D).

Production of Soluble Human ACE2

Figure 2A:
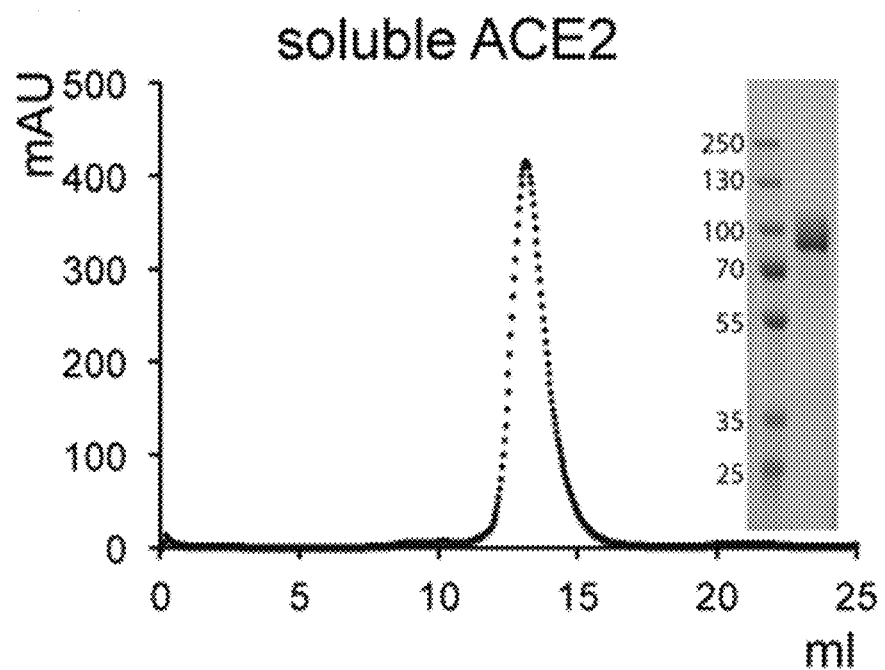
FIGS. 2A-2C show production of soluble human ACE2.
Figure 2B:
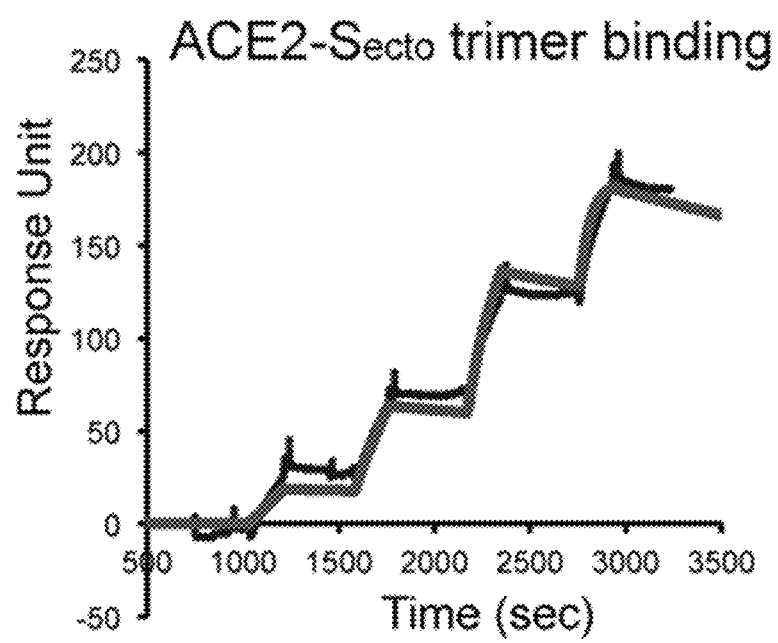
Figure 2C:
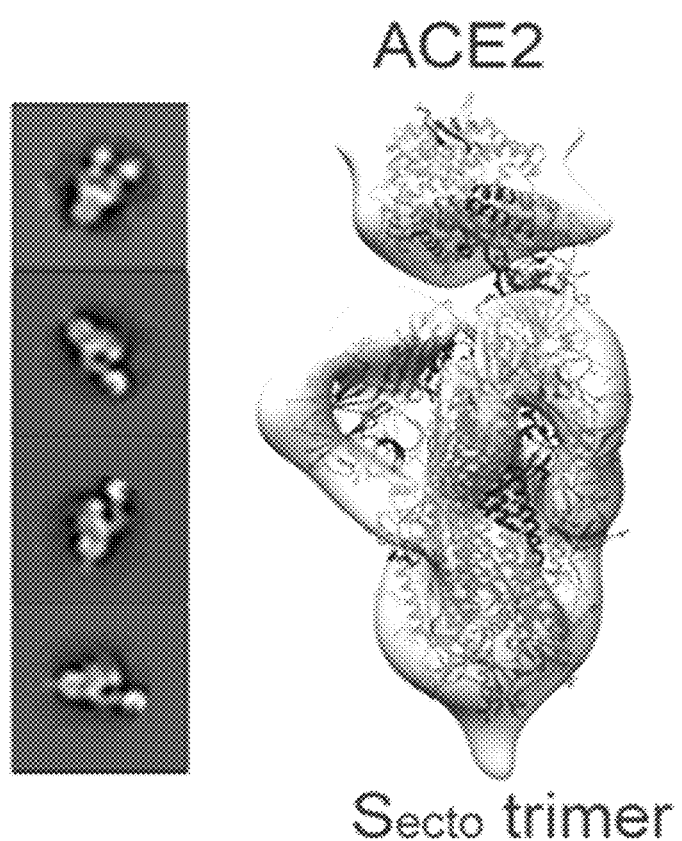

Production of soluble human ACE2 was performed as described below. His-tagged ACE2 was resolved by gel-filtration chromatography (FIG. 2A) and the peak fractions were analyzed by Coomassie stained SDS-PAGE (FIG. 2A, inset). These results indicated that the preparation was stable and homogeneous. Binding of ACE2 to the soluble S protein trimer (FIGS. 1A-1D) was analyzed by SPR single-cycle kinetic analysis (FIG. 2B). Negative stain EM of the ACE2-S complex was also performed. Representative 2D class averages, and the resulting 3D reconstruction superimposed with the atomic models of S trimer and ACE2 are shown in FIG. 2C.

Binding of ACE2 to S Trimer with/without Avidity

Figure 3A:
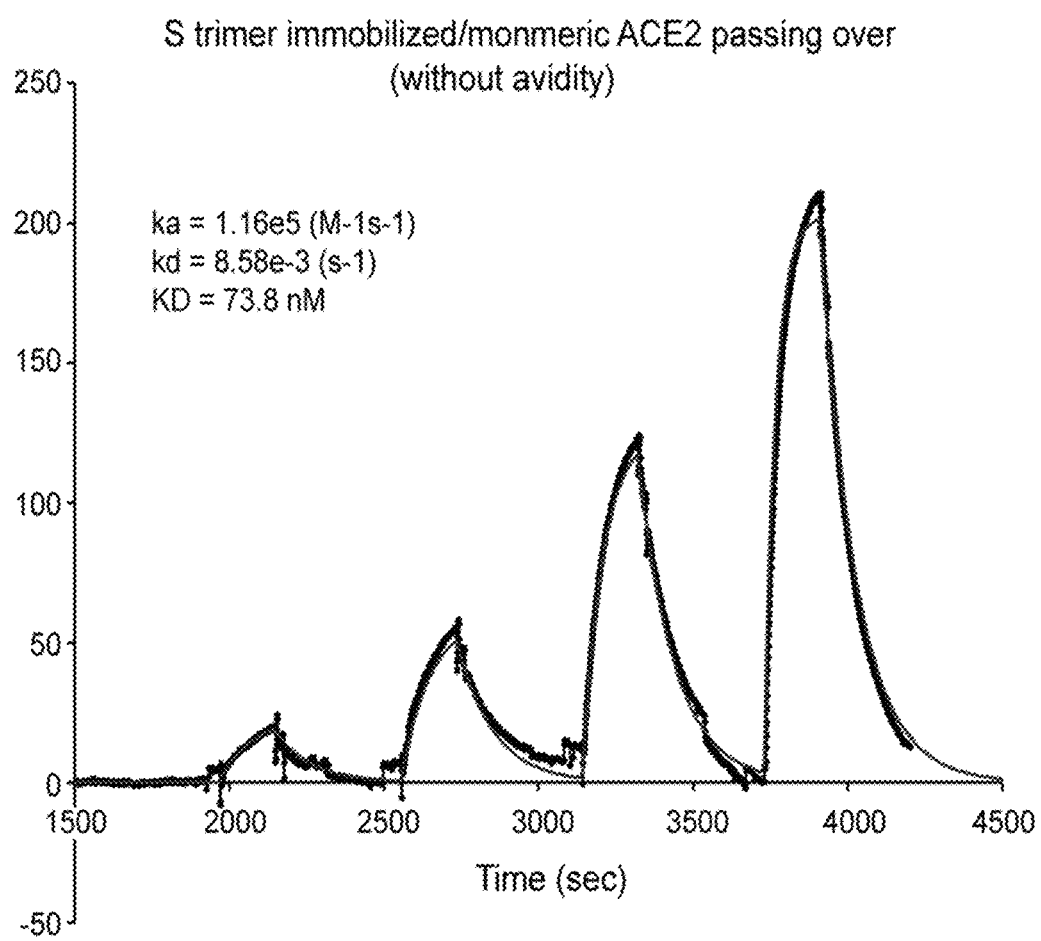
FIGS. 3A-3C show binding of ACE2 to S trimer analyzed by a surface plasmon resonance (SPR) assay.
Figure 3B:
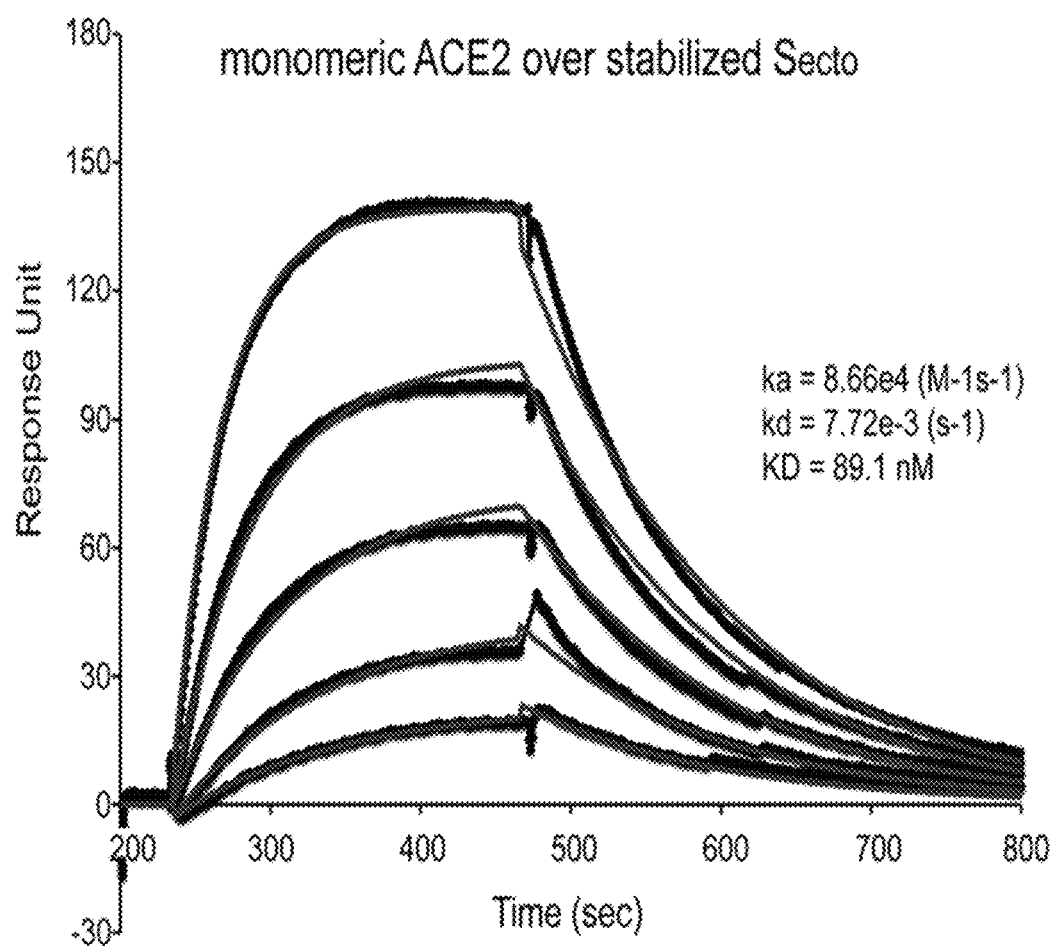

Binding of ACE2 to S protein trimer was analyzed by a surface plasmon resonance (SPR) assay. The SARS-CoV-2 S protein trimer was captured to the surface of a CM5 sensor chip and monomeric ACE2 at various concentrations was passed over the S protein surface individually without regeneration for single cycle kinetic analysis. The recorded sensorgram, fit, and binding constants are shown in FIG. 3A. Multi cycle kinetic analysis was also performed and is shown in FIG. 3B. Under these conditions, there was a minimal level of avidity if any at all.

Figure 3C:
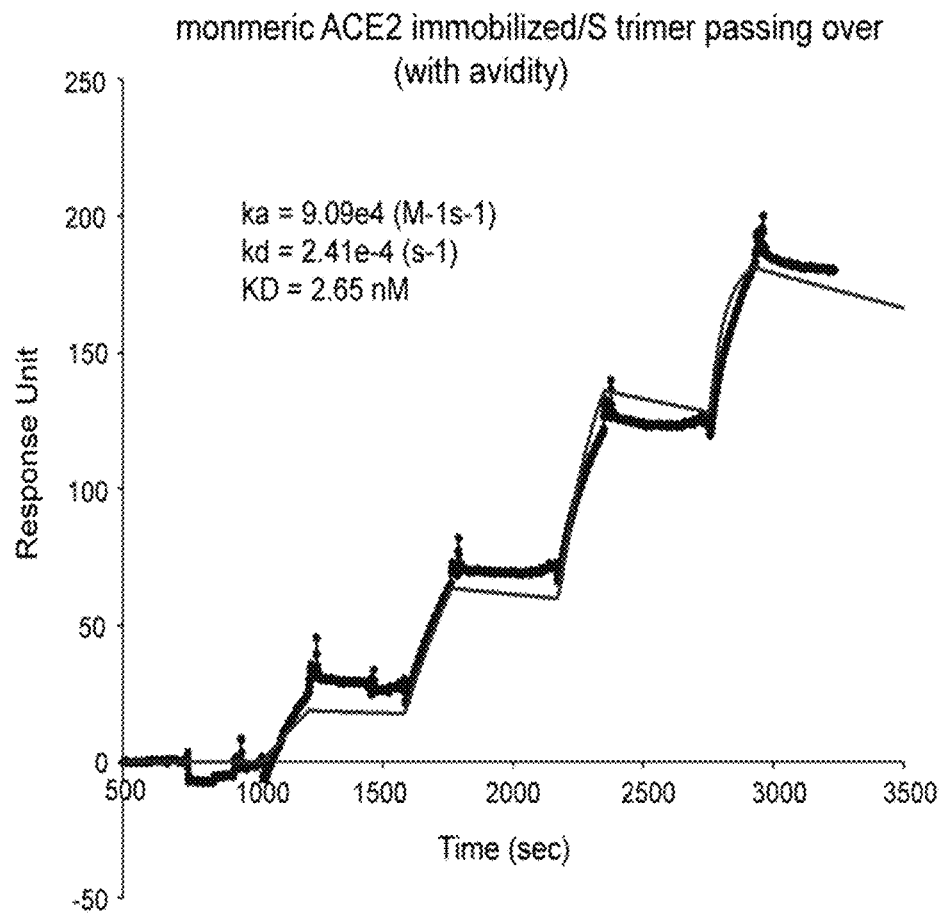

The ACE2 monomer was captured to the surface of a CM5 sensor chip and trimeric S protein at various concentrations was passed over the ACE2 surface individually without regeneration for single cycle kinetic analysis. The recorded sensorgram, fit, and binding constants are shown in FIG. 3C. Under these conditions, there was avidity due to immobilization of the monomeric component.

Design and Production of Modified Oligomeric ACE2 Protein.

Binding of the wildtype ACE2 to the S protein trimer showed a fast off-rate (FIG. 3A), which is disadvantageous for a diagnostic test. Immobilizing monomeric ACE2 on the sensor chip surface led to a reduction in off-rate by >30 fold, supporting the proposition that oligomeric ACE2 proteins will show substantially higher affinity to the S protein trimer, including but not limited to the spikes on the surface of live virus. As a result, oligomeric ACE2 (specifically in this case trimeric and tetrameric) was produced to slow the dissociation by avidity (Table 1).

Figure 4:
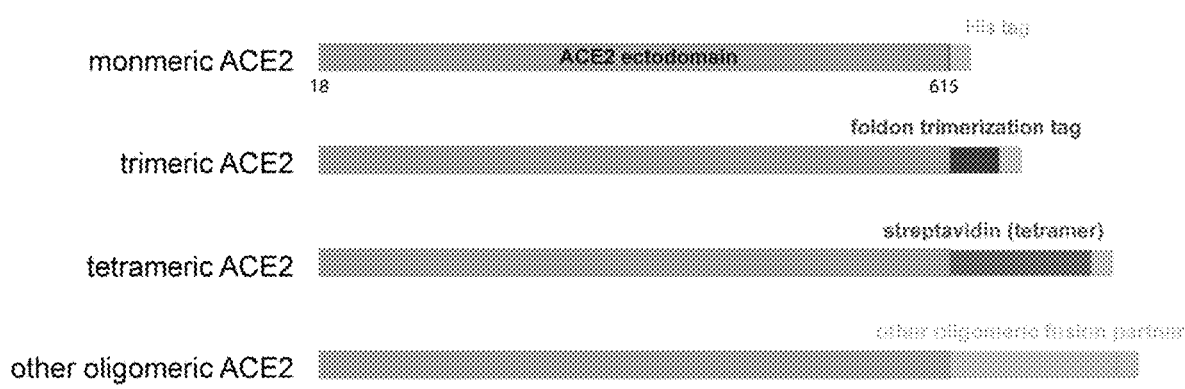
FIG. 4 depicts the design of modified oligomeric ACE2 protein. A schematic representation of the construct design is shown with the ectodomain of ACE2 fused with various partners that form different oligomeric states, such as foldon for a trimer; streptavidin for a tetramer. Additional structure-guided mutations were introduced in the ACE2 ectodomain to increase its stability without affecting the binding to SARS-CoV-2 S protein.

Modified oligomeric ACE2 proteins were designed to further increase avidity. A schematic representation of the construct design with the ectodomain of ACE2 fused with various partners that form different oligomeric state, such as foldon for a trimer and streptavidin for a tetramer, is shown in FIG. 4.

Figure 5A:
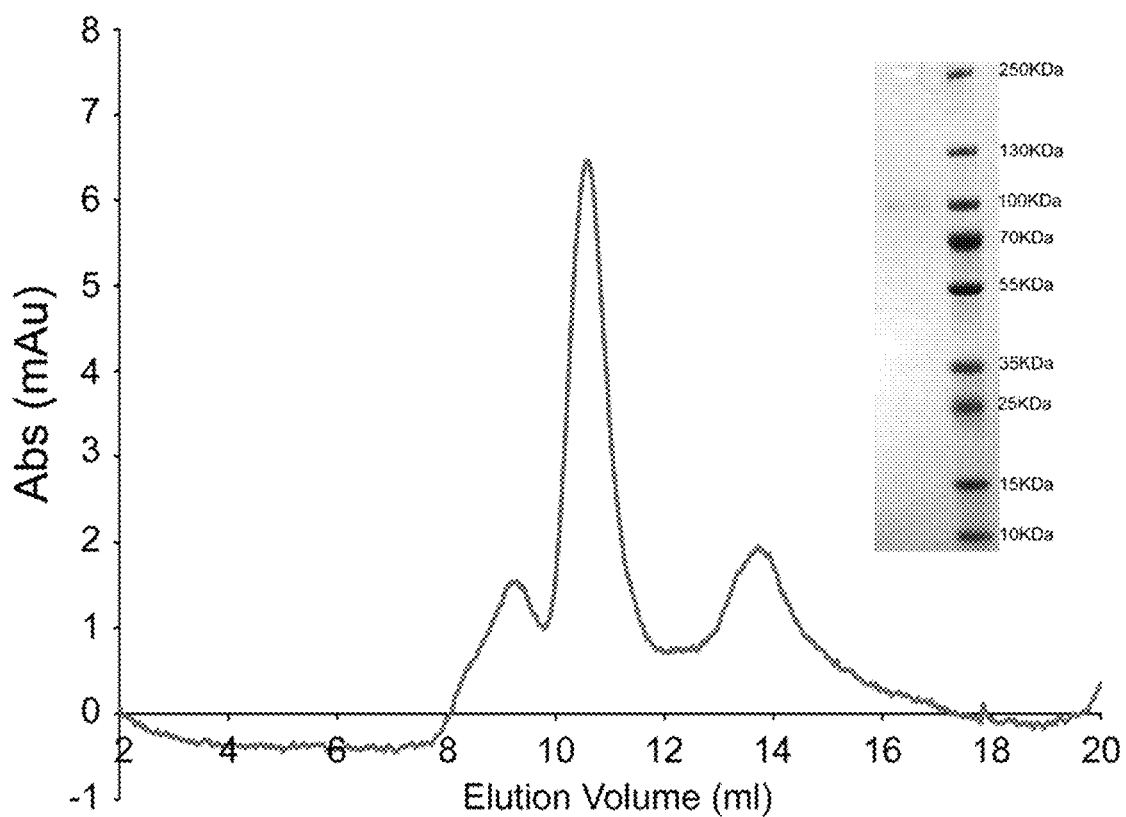
Figure 7A:
FIGS. 7A-7D show Cryo-EM structures of the ACE2-soluble S trimer complexes. Four distinct classes were identified and refined from a sample prepared by mixing a monomeric ACE2 and the stabilized soluble SARS-CoV-2 trimer.
Figure 7B:
Figure 7C:
Figure 7D:
Figure 8A:
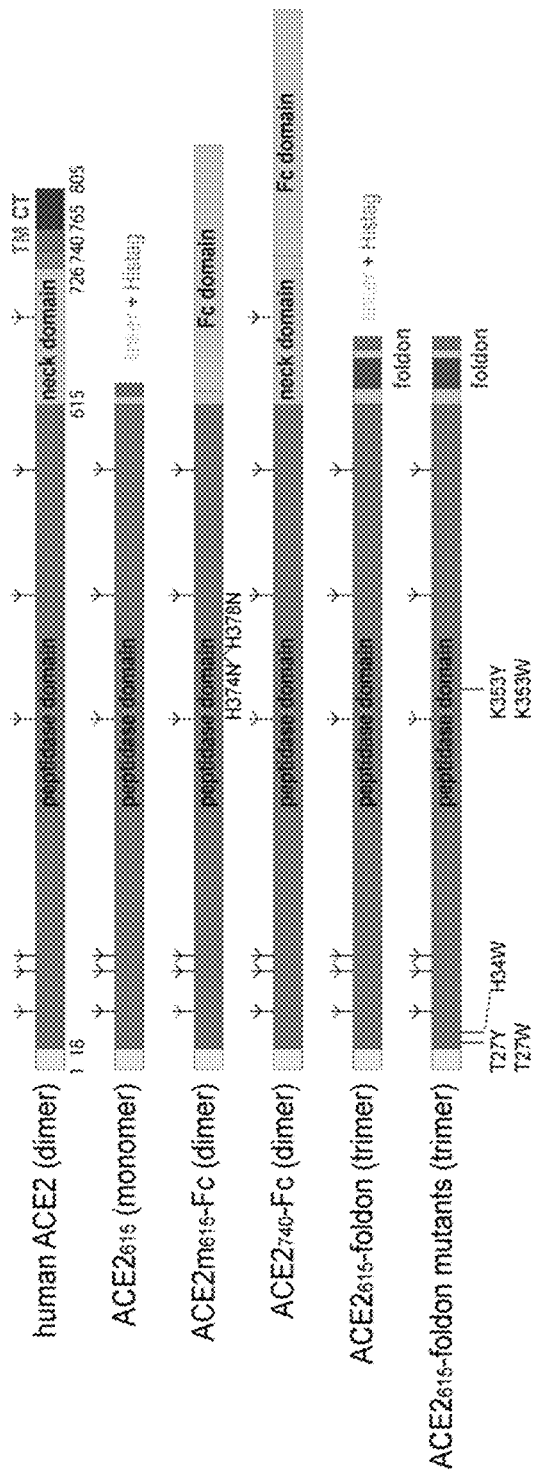
Figure 8B:
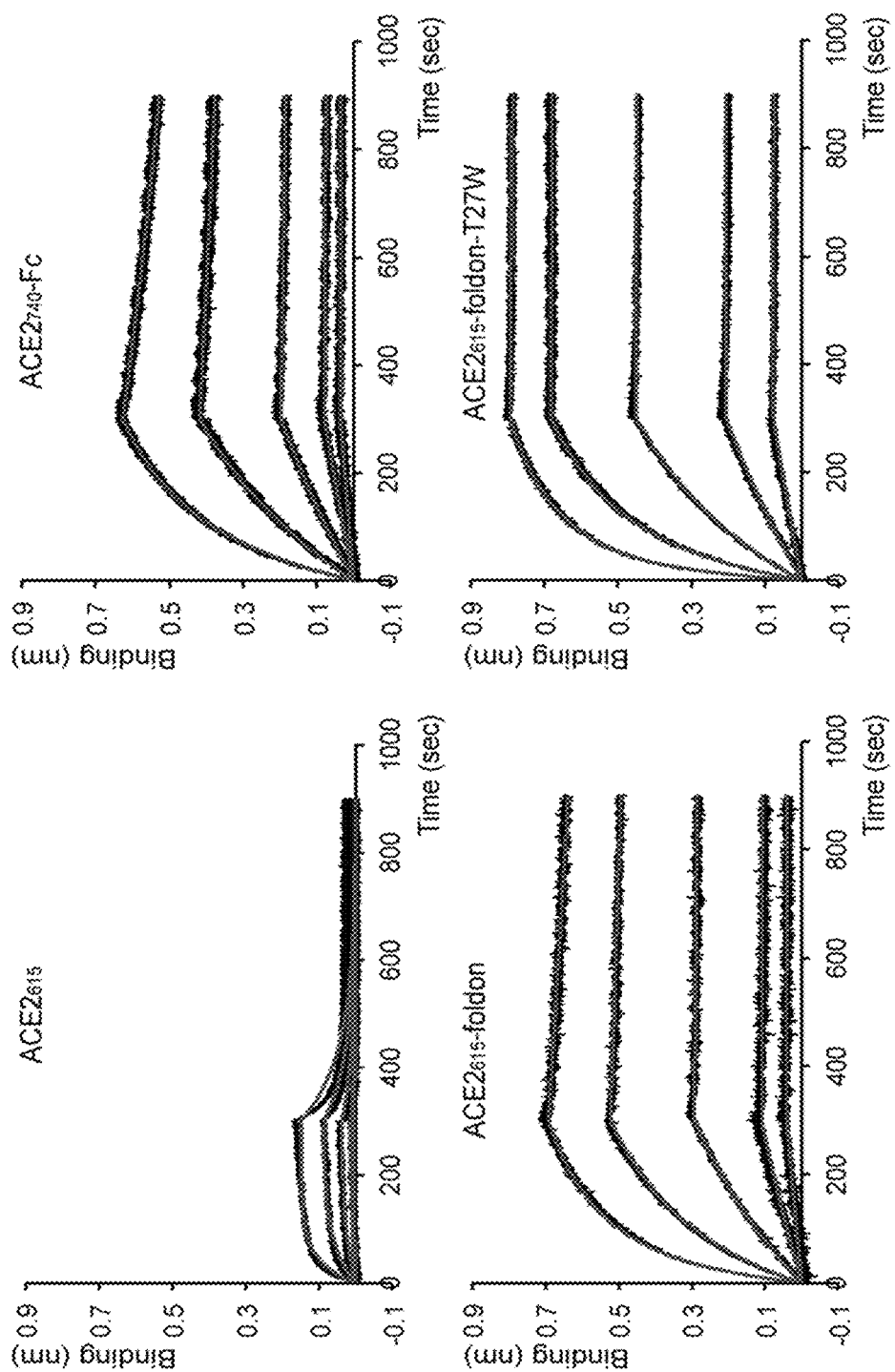
Figure 9A:
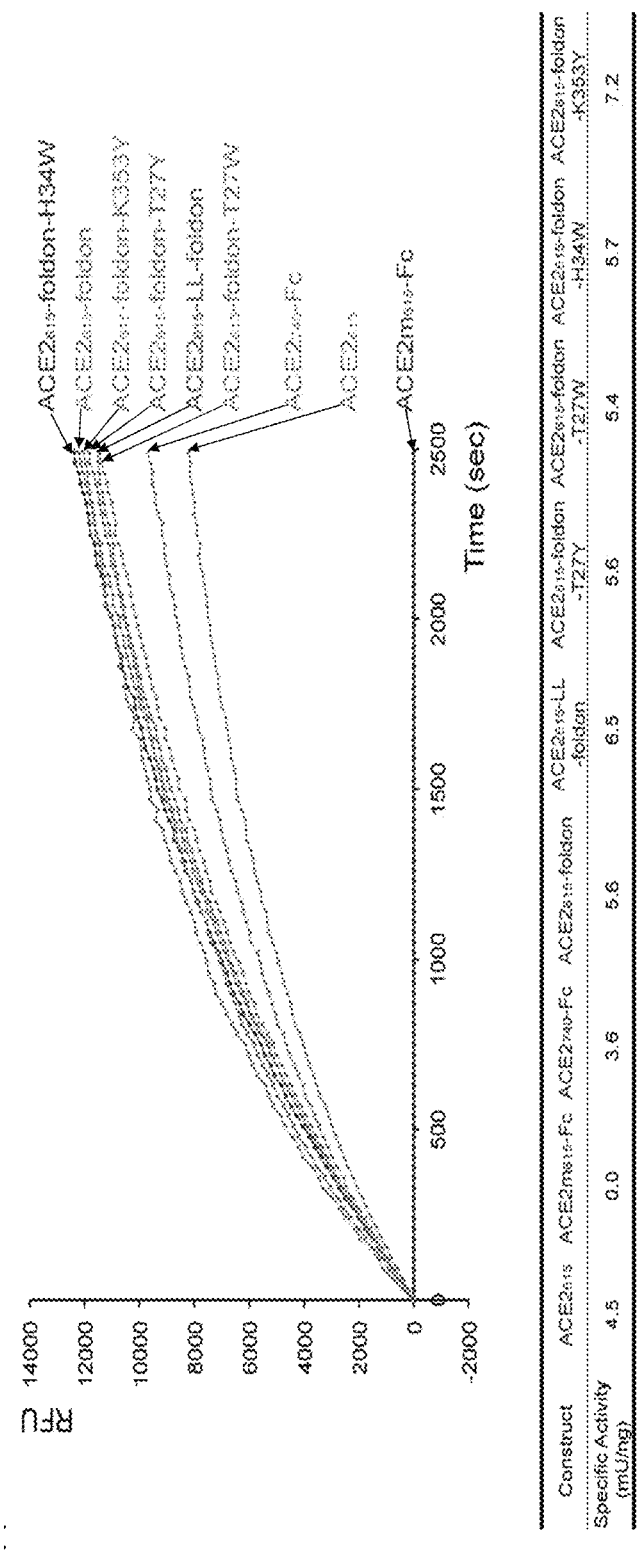
FIGS. 9A-9B show ACE2 peptidase activity and negative regulation of Ang II receptor type 1 activation.
Figure 9B:
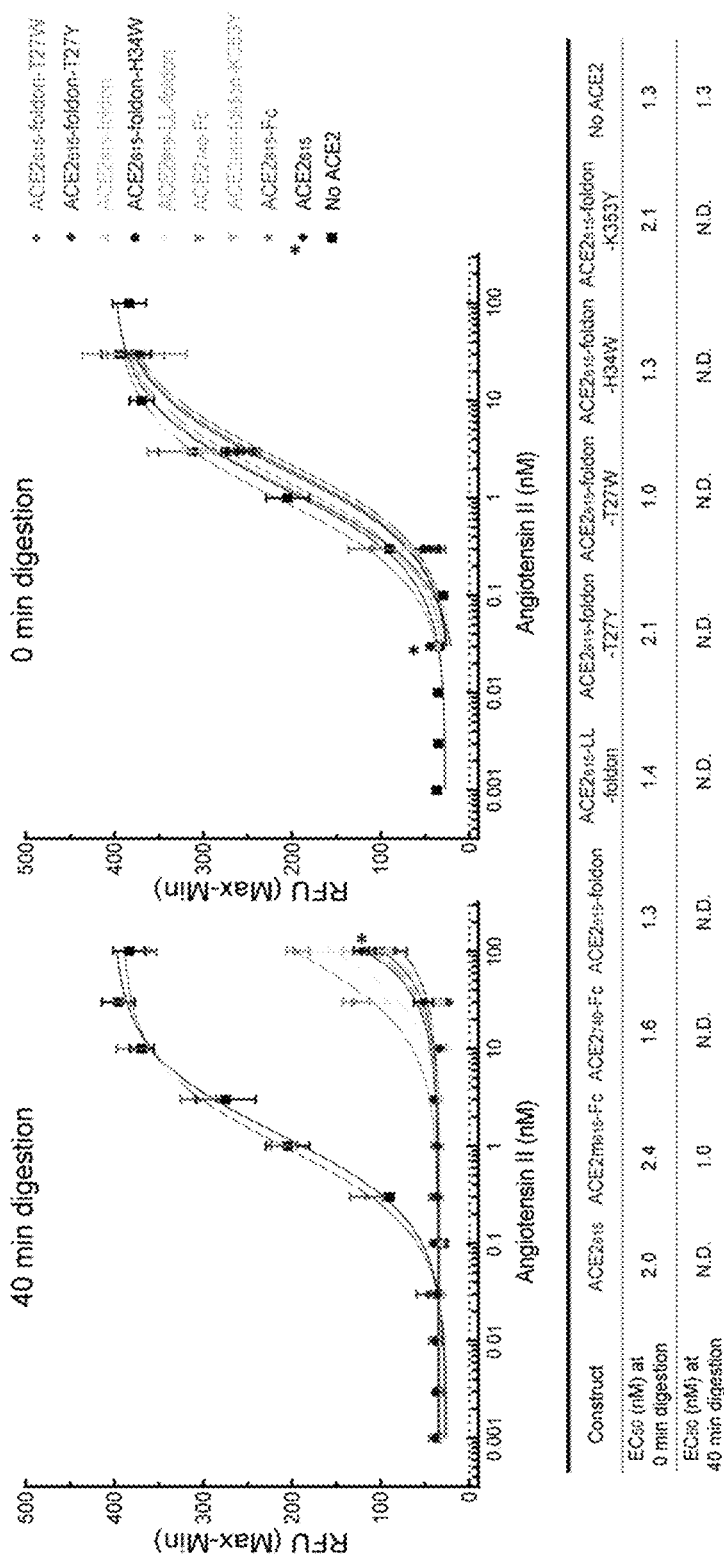

Soluble trimeric ACE2 was produced using a soluble ACE2-Foldon protein. His-tagged ACE2-foldon protein was resolved by gel-filtration chromatography (FIG. 5A). The peak fractions were analyzed by Coomassie-stained SDS-PAGE (FIG. 5A, inset).

To show binding of the S protein trimer from SARS-CoV-2 to ACE2 proteins, the S protein trimer was captured on the surface of a CM5 sensor chip. Monomeric ACE2 at various concentrations was passed over the S protein surface individually, and the recorded sensorgram was shown, as well as the fit of the data (FIG. 5B). Similarly, trimeric ACE2 protein at various concentrations was passed over the S protein surface individually. The recorded sensorgram and fit of the date, as well as the binding constants were shown (FIG. 5B). These results showed that the binding affinity of the trimeric ACE2 increased by >30 fold as compared to monomeric ACE2.

As shown in Table 2, additional structure-guided mutations can be introduced into the ACE2 ectodomain to increase its stability without affecting the binding to SARS-CoV-2 S protein. The interface between ACE2 and the S receptor binding domain was also redesigned to increase the contacting surface, guided by the high-resolution structures. The new ACE2 constructs had an off-rate slower by 1-2 order of magnitude than the wildtype protein.

Methods

Production of Soluble Human ACE2 and its Variants

The expression constructs of soluble human ACE2 and its variants were created using codon-optimized synthetic genes, produced by Genscript (Piscataway, N.J.) or standard PCR techniques. HEK 293T cells were transiently transfected with the ACE2 expression constructs, and grown in DMEM with 10% FBS to confluence and then changed to Freestyle 293 expression medium (Invitrogen). The cell supernatants were harvested at 96-108 hrs. after medium change. The histagged ACE proteins were purified by Ni-NTA (Qiagen), followed by gel filtration chromatography, following well-established protocols. The purified proteins were concentrated, frozen in liquid nitrogen and stored at −80° C. before use. SARS-CoV-2 S proteins were produced in a similar manner.

SPR Binding Assays

All experiments were performed in duplicate with a Biacore 3000 instrument (Biacore, Inc.) at 20° C. in HBS-EP running buffer (10 mM HEPES pH 7.4, 150 mM NaCl, 3 mM EDTA, 0.005% P20), with immobilization levels of 250-600 RU to avoid rebinding events. Immobilization to CM5 chips was performed following the standard amine coupling procedure as recommended by the manufacturer. For kinetic measurements, sensorgrams were recorded by passing various concentrations of an analyte over the immobilized ligand surface at a flow rate of 50 μmin with a 2-min association phase followed by a 10-minute dissociation phase. The surface was regenerated between each experiment with two consecutive injections (1 min) of 10 mM glycine-HCl pH 2.1 at 50 μl/min followed by a 5-min equilibration phase in the HBS-EP buffer before the subsequent experiment. Identical injections over blank surfaces are subtracted from the data for kinetic analysis. Binding kinetics are analyzed by BiaEvaluation software (Biacore, Inc.) using a 1:1 Langmuir binding model.

SEQUENCES

Soluble ACE2:
(SEQ ID NO: 1)
MSSSSWLLLSLVAVTAAQSTIEEQAKTFLDKFNHEAEDLFYQSSLASWN
YNTNITEENVQNMNNAGDKWSAFLKEQSTLAQMYPLQEIQNLTVKLQLQ
ALQQNGSSVLSEDKSKRLNTILNTMSTIYSTGKVCNPDNPQECLLLEPG -continued LNEIMANSLDYNERLWAWESWRSEVGKQLRPLYEEYVVLKNEMARANHY
EDYGDYWRGDYEVNGVDGYDYSRGQLIEDVEHTFEEIKPLYEHLHAYVR
AKLMNAYPSYISPIGCLPAHLLGDMWGRFWTNLYSLTVPFGQKPNIDVT
DAMVDQAWDAQRIFKEAEKFFVSVGLPNMTQGFWENSMLTDPGNVQKAV
CHPTAWDLGKGDFRILMCTKVTMDDFLTAHHEMGHIQYDMAYAAQPFLL
RNGANEGFHEAVGEIMSLSAATPKHLKSIGLLSPDFQEDNETEINFLLK
QALTIVGTLPFTYMLEKWRWMVFKGEIPKDQWMKKWWEMKREIVGVVEP
VPHDETYCDPASLFHVSNDYSFIRYYTRTLYQFQFQEALCQAAKHEGPL
HKCDISNSTEAGQKLFNMLRLGKSEPWTLALENVVGAKNMNVRPLLNYF
EPLFTWLKDQNKNSFVGWSTDWSPYADSGGSHHHHHH

TABLE 1

Oligomeric ACE2 (trimeric and tetrameric) Sequences
Bold: His tag; Italics: Foldon trimerization/Streptavidin tetramerization tag

| SEQ ID NO: | Oligomerized ACE2 | Sequence |
|---|---|---|
| 2 | Sol-ACE2-Foldon | MSSSSWLLLSLVAVTAAQSTIEEQAKTFLDKFNHEAEDLFYQSSLASWNYNTN ITEENVQNMNNAGDKWSAFLKEQSTLAQMYPLQEIQNLTVKLQLQALQQNG SSVLSEDKSKRLNTILNTMSTIYSTGKVCNPDNPQECLLLEPGLNEIMANSLDY NERLWAWESWRSEVGKQLRPLYEEYVVLKNEMARANHYEDYGDYWRGDY EVNGVDGYDYSRGQLIEDVEHTFEEIKPLYEHLHAYVRAKLMNAYPSYISPIG CLPAHLLGDMWGRFWTNLYSLTVPFGQKPNIDVTDAMVDQAWDAQRIFKEA EKFFVSVGLPNMTQGFWENSMLTDPGNVQKAVCHPTAWDLGKGDFRILMCT KVTMDDFLTAHHEMGHIQYDMAYAAQPFLLRNGANEGFHEAVGEIMSLSAA TPKHLKSIGLLSPDFQEDNETEINFLLKQALTIVGTLPFTYMLEKWRWMVFKG EIPKDQWMKKWWEMKREIVGVVEPVPHDETYCDPASLFHVSNDYSFIRYYTR TLYQFQFQEALCQAAKHEGPLHKCDISNSTEAGQKLFNMLRLGKSEPWTLAL ENVVGAKNMNVRPLLNYFEPLFTWLKDQNKNSFVGWSTDWSPYADSGGSLE GGSG *GYIPEAPRDGQAYVRKDGEWVLLSTFL*GGSHHHHHH |
| 3 | Sol-ACE2-Strepavidin | MSSSSWLLLSLVAVTAAQSTIEEQAKTFLDKFNHEAEDLFYQSSLASWNYNT NITEENVQNMNNAGDKWSAFLKEQSTLAQMYPLQEIQNLTVKLQLQALQQN GSSVLSEDKSKRLNTILNTMSTIYSTGKVCNPDNPQECLLLEPGLNEIMANSLD YNERLWAWESWRSEVGKQLRPLYEEYVVLKNEMARANHYEDYGDYWRGD YEVNGVDGYDYSRGQLIEDVEHTFEEIKPLYEHLHAYVRAKLMNAYPSYISPI GCLPAHLLGDMWGRFCTNLYSLTVPFGQKPNIDVTDAMVDQAWDAQRIFKE AEKFFVSVGLPNMTQGFWENSMLTDPGNVQKAVCHPTAWDLGKGDFRILM CTKVTMDDFLTAHHEMGHIQYDMAYAAQPFLLRNGANEGFHEAVGEIMSLS AATPKHLKSIGLLSPDFQEDNETEINFLLKQALTIVCTLPFTYMLEKWRWMVF KGEIPKDQWMKKWWEMKREIVGVVEPVPHDETYCDPASLFHVSNDYSFIRY YTRTLYQFQFQEALCQAAKHEGPLHKCDISNSTEAGQKLFNMLRLGKSEPWT LALENVVGAKNMNVRPLLNYFEPLFTWLKDQNKNSFVGWSTDWSPYADSG GGGSG *GYIPEAPRDGQAYVRKDGEWVLLSTFL*GGSHHHHHH |

TABLE 2

Modified Oligomeric ACE2 Sequences
Underline: Cys involved in disulfide bond; Bold: His tag; Italics: Foldon trimerization tag

| SEQ ID NO: | Construct | Sequence |
|---|---|---|
| 4 | Sol-ACE2-Foldon-C275-C448 | MSSSSWLLLSLVAVTAAQSTIEEQAKTFLDKFNHEAEDLFYQSSLASWNYNTN ITEENVQNMNNAGDKWSAFLKEQSTLAQMYPLQEIQNLTVKLQLQALQQNGS SVLSEDKSKRLNTILNTMSTIYSTGKVCNPDNPQECLLLEPGLNEIMANSLDYN ERLWAWESWRSEVGKQLRPLYEEYVVLKNEMARANHYEDYGDYWRGDYE VNGVDGYDYSRGQLIEDVEHTFEEIKPLYEHLHAYVRAKLMNAYPSYISPIGC LPAHLLGDMWGRF<u>C</u>TNLYSLTVPFGQKPNIDVTDAMVDQAWDAQRIFKEAE KFFVSVGLPNMTQGFWENSMLTDPGNVQKAVCHPTAWDLGKGDFRILMCTK VTMDDFLTAHHEMGHIQYDMAYAAQPFLLRNGANEGFHEAVGEIMSLSAATP KHLKSIGLLSPDFQEDNETEINFLLKQALTIV<u>C</u>TLPFTYMLEKWRWMVFKGEIP KDQWMKKWWEMKREIVGVVEPVPHDETYCDPASLFHVSNDYSFIRYYTRTL |

TABLE 2-continued

Modified Oligomeric ACE2 Sequences
Underline: Cys involved in disulfide bond; Bold: His tag; Italics: Foldon trimerization tag

| SEQ ID NO: | Construct | Sequence |
|---|---|---|
|  |  | YQFQFQEALCQAAKHEGPLHKCDISNSTEAGQKLFNMLRLGKSEPWTLALEN VVGAKNMNVRPLLNYFEPLFTWLKDQNKNSFVGWSTDWSPYADSGGGSG *GYIPEAPRDGQAYVRKDGEWVLLSTFL*GGSHHHHHH |
| 5 | Sol-ACE2-Foldon-C377-C408 | MSSSSWLLLSLVAVTAAQSTIEEQAKTFLDKFNHEAEDLFYQSSLASWNYNTNI TEENVQNMNNAGDKWSAFLKEQSTLAQMYPLQEIQNLTVKLQLQALQQNGSS VLSEDKSKRLNTILNTMSTIYSTGKVCNPDNPQECLLLEPGLNEIMANSLDYNE RLWAWESWRSEVGKQLRPLYEEYVVLKNEMARANHYEDYGDYWRGDYEVN GVDGYDYSRGQLIEDVEHTFEEIKPLYEHLHAYVRAKLMNAYPSYISPIGCLPA HLLGDMWGRFWTNLYSLTVPFGQKPNIDVTDAMVDQAWDAQRIFKEAEKFFV SVGLPNMTQGFWENSMLTDPGNVQKAVCHPTAWDLGKGDFRILMCTKVTMD DFLTAHHEMCHIQYDMAYAAQPFLLRNGANEGFHEAVGEICSLSAATPKHLKS IGLLSPDFQEDNETEINFLLKQALTIVGTLPFTYMLEKWRWMVFKGEIPKDQW MKKWWEMKREIVGVVEPVPHDETYCDPASLFHVSNDYSFIRYYTRTLYQFQF QEALCQAAKHEGPLHKCDISNSTEAGQKLFNMLRLGKSEPWTLALENVVGAK NMNVRPLLNYFEPLFTWLKDQNKNSFVGWSTDWSPYADSGGGSG *GYIPEAPRDGQAYVRKDGEWVLLSTFL*GGSHHHHHH |
| 6 | Sol-ACE2-Foldon-C523-C583 | MSSSSWLLLSLVAVTAAQSTIEEQAKTFLDKFNHEAEDLFYQSSLASWNYNTNI TEENVQNMNNAGDKWSAFLKEQSTLAQMYPLQEIQNLTVKLQLQALQQNGSS VLSEDKSKRLNTILNTMSTIYSTGKVCNPDNPQECLLLEPGLNEIMANSLDYNE RLWAWESWRSEVGKQLRPLYEEYVVLKNEMARANHYEDYGDYWRGDYEVN GVDGYDYSRGQLIEDVEHTFEEIKPLYEHLHAYVRAKLMNAYPSYISPIGCLPA HLLGDMWGRFWTNLYSLTVPFGQKPNIDVTDAMVDQAWDAQRIFKEAEKFFV SVGLPNMTQGFWENSMLTDPGNVQKAVCHPTAWDLGKGDFRILMCTKVTMD DFLTAHHEMGHIQYDMAYAAQPFLLRNGANEGFHEAVGEIMSLSAATPKHLK SIGLLSPDFQEDNETEINFLLKQALTIVGTLPFTYMLEKWRWMVFKGEIPKDQW MKKWWEMKREIVGVVEPVPHDETYCDPASLFHVSNDYSFIRYYTRTLYQCQF QEALCQAAKHEGPLHKCDISNSTEAGQKLFNMLRLGKSEPWTLALENVVGAK NMNVRCLLNYFEPLFTWLKDQNKNSFVGWSTDWSPYADSGGGSG *GYIPEAPRDGQAYVRKDGEWVLLSTFL*GGSHHHHHH |
| 7 | SoL-ACE2-Foldon-C523-C584 | MSSSSWLLLSLVAVTAAQSTIEEQAKTFLDKFNHEAEDLFYQSSLASWNYNTNI TEENVQNMNNAGDKWSAFLKEQSTLAQMYPLQEIQNLTVKLQLQALQQNGSS VLSEDKSKRLNTILNTMSTIYSTGKVCNPDNPQECLLLEPGLNEIMANSLDYNE RLWAWESWRSEVGKQLRPLYEEYVVLKNEMARANHYEDYGDYWRGDYEVN GVDGYDYSRGQLIEDVEHTFEEIKPLYEHLHAYVRAKLMNAYPSYISPIGCLPA HLLGDMWGRFWTNLYSLTVPFGQKPNIDVTDAMVDQAWDAQRIFKEAEKFFV SVGLPNMTQGFWENSMLTDPGNVQKAVCHPTAWDLGKGDFRILMCTKVTMD DFLTAHHEMGHIQYDMAYAAQPFLLRNGANEGFHEAVGEIMSLSAATPKHLK SIGLLSPDFQEDNETEINFLLKQALTIVGTLPFTYMLEKWRWMVFKGEIPKDQW MKKWWEMKREIVGVVEPVPHDETYCDPASLFHVSNDYSFIRYYTRTLYQCQF QEALCQAAKHEGPLHKCDISNSTEAGQKLFNMLRLGKSEPWTLALENVVGAK NMNVRPCLNYFEPLFTWLKDQNKNSFVGWSTDWSPYADSGGGSG *GYIPEAPRDGQAYVRKDGEWVLLSTFL*GGSHHHHHH |
| 8 | Sol-ACE2-Foldon-C275-C448-C377-C408 | MSSSSWLLLSLVAVTAAQSTIEEQAKTFLDKFNHEAEDLFYQSSLASWNYNTN IEENVQNMNNAGDKWSAFLKEQSTLAQMYPLQEIQNLTVKLQLQALQQNGS SVLSEDKSKRLNTILNTMSTIYSTGKVCNPDNPQECLLLEPGLNEIMANSLDYN ERLWAWESWRSEVGKQLRPLYEEYVVLKNEMARANHYEDYGDYWRGDYE VNGVDGYDYSRGQLIEDVEHTFEEIKPLYEHLHAYVRAKLMNAYPSYISPIGC LPAHLLGDMWGRFCTNLYSLTVPFGQKPNIDVTDAMVDQAWDAQRIFKEAE KFFVSVGLPNMTQGFWENSMLTDPGNVQKAVCHPTAWDLGKGDFRILMCTK VTMDDFLTAHHEMCHIQYDMAYAAQPFLLRNGANEGFHEAVGEICSLSAATP KHLKSIGLLSPDFQEDNETEINFLLKQALTIVCTLPFTYMLEKWRWMVFKGEIP KDQWMKKWWEMKREIVGVVEPVPHDETYCDPASLFHVSNDYSFIRYYTRTL YQFQFQEALCQAAKHEGPLHKCDISNSTEAGQKLFNMLRLGKSEPWTLALEN VVGAKNMNVRPLLNYFEPLFTWLKDQNKNSFVGWSTDWSPYADSGGGSG *GYIPEAPRDGQAYVRKDGEWVLLSTFL*GGSHHHHHH |
| 9 | Sol-ACE2-Foldon-C275-C448-C523-C583 | MSSSSWLLLSLVAVTAAQSTIEEQAKTFLDKFNHEAEDLFYQSSLASWNYNTNI TEENVQNMNNAGDKWSAFLKEQSTLAQMYPLQEIQNLTVKLQLQALQQNGSS VLSEDKSKRLNTILNTMSTIYSTGKVCNPDNPQECLLLEPGLNEIMANSLDYNE RLWAWESWRSEVGKQLRPLYEEYVVLKNEMARANHYEDYGDYWRGDYEVN GVDGYDYSRGQLIEDVEHTFEEIKPLYEHLHAYVRAKLMNAYPSYISPIGCLPA HLLGDMWGRFCTNLYSLTVPFGQKPNIDVTDAMVDQAWDAQRIFKEAEKFFV SVGLPNMTQGFWENSMLTDPGNVQKAVCHPTAWDLGKGDFRILMCTKVTMD DFLTAHHEMGHIQYDMAYAAQPFLLRNGANEGFHEAVGEIMSLSAATPKHLK |

TABLE 2-continued

Modified Oligomeric ACE2 Sequences
Underline: Cys involved in disulfide bond; Bold: His tag; Italics: Foldon trimerization tag

| SEQ ID NO: | Construct | Sequence |
|---|---|---|
|  |  | SIGLLSPDFQEDNETEINFLL TABLE 2-continued Modified Oligomeric ACE2 Sequences
Underline: Cys involved in disulfide bond; Bold: His tag; Italics: Foldon tr TABLE 3-continued Additional engineered ACE2 constructs
Underline: modification; Bold: His tag; Italics: Foldon trimerization tag

| SEQ ID NO: | Construct | Sequence |
|---|---|---|
| 20 | Sol-ACE2-Foldon-K353W | MSSSSWLLLSLVAVTAAQSTIEEQAKTFLDKFNHEAEDLFYQSSLASWNYNTNI TEENVQNMNNAGDKWSAFLKEQSTLAQMYPLQEIQNLTVKLQLQALQQNGSS VLSEDKSKRLNTILNTMSTIYSTGKVCNPDNPQECLLLEPGLNEIMANSLDYNE RLWAWESWRSEVGKQLRPLYEEYVVLKNEMARANHYEDYGDYWRGDYEVN GVDGYDYSRGQLIEDVEHTFEEIKPLYEHLHAYVRAKLMNAYPSYISPIGCLPA HLLGDMWGRFWTNLYSLTVPFGQKPNIDVTDAMVDQAWDAQRIFKEAEKFFV SVGLPNMTQGFWENSMLTDPGNVQKAVCHPTAWDLGWGDFRILMCTKVTMD DFLTAHHEMGHIQYDMAYAAQPFLLRNGANEGFHEAVGEIMSLSAATPKHLK SIGLLSPDFQEDNETEINFLLKQALTIVGTLPFTYMLEKWRWMVFKGEIPKDQW MKKWWEMKREIVGVVEPVPHDETYCDPASLFHVSNDYSFIRYYTRTLYQFQF QEALCQAAKHEGPLHKCDISNSTEAGQKLFNMLRLGKSEPWTLALENVVGAK NMNVRPLLNYFEPLFTWLKDQNKNSFVGWSTDWSPYADSGGGGSGGYIPEAPR DGQAYVRKDGEWVLLSTFLGGSHHHHHH |
| 21 | Sol-ACE2-Foldon-K353Y | MSSSSWLLLSLVAVTAAQSTIEEQAKTFLDKFNHEAEDLFYQSSLASWNYNTNI TEENVQNMNNAGDKWSAFLKEQSTLAQMYPLQEIQNLTVKLQLQALQQNGSS VLSEDKSKRLNTILNTMSTIYSTGKVCNPDNPQECLLLEPGLNEIMANSLDYNE RLWAWESWRSEVGKQLRPLYEEYVVLKNEMARANHYEDYGDYWRGDYEVN GVDGYDYSRGQLIEDVEHTFEEIKPLYEHLHAYVRAKLMNAYPSYISPIGCLPA HLLGDMWGRFWTNLYSLTVPFGQKPNIDVTDAMVDQAWDAQRIFKEAEKFFV SVGLPNMTQGFWENSMLTDPGNVQKAVCHPTAWDLGYGDFRILMCTKVTMD DFLTAHHEMGHIQYDMAYAAQPFLLRNGANEGFHEAVGEIMSLSAATPKHLK SIGLLSPDFQEDNETEINFLLKQALTIVGTLPFTYMLEKWRWMVFKGEIPKDQW MKKWWEMKREIVGVVEPVPHDETYCDPASLFHVSNDYSFIRYYTRTLYQFQF QEALCQAAKHEGPLHKCDISNSTEAGQKLFNMLRLGKSEPWTLALENVVGAK NMNVRPLLNYFEPLFTWLKDQNKNSFVGWSTDWSPYADSGGGGSGGYIPEAPR DGQAYVRKDGEWVLLSTFLGGSHHHHHH |
| 22 | Sol-ACE2-Foldon-X27-X34-X353* *X27 is T, W, or Y; X34 is H, F, or W; X353 is or Y | MSSSSWLLLSLVAVTAAQSTIEEQAKXFLDKFNXEAEDLFYQSSLASWNYNTNI TEENVQNMNNAGDKWSAFLKEQSTLAQMYPLQEIQNLTVKLQLQALQQNGSS VLSEDKSKRLNTILNTMSTIYSTGKVCNPDNPQECLLLEPGLNEIMANSLDYNE RLWAWESWRSEVGKQLRPLYEEYVVLKNEMARANHYEDYGDYWRGDYEVN GVDGYDYSRGQLIEDVEHTFEEIKPLYEHLHAYVRAKLMNAYPSYISPIGCLPA HLLGDMWGRFWTNLYSLTVPFGQKPNIDVTDAMVDQAWDAQRIFKEAEKFFV SVGLPNMTQGFWENSMLTDPGNVQKAVCHPTAWDLGXGDFRILMCTKVTMD DFLTAHHEMGHIQYDMAYAAQPFLLRNGANEGFHEAVGEIMSLSAATPKHLK SIGLLSPDFQEDNETEINFLLKQALTIVGTLPFTYMLEKWRWMVFKGEIPKDQW MKKWWEMKREIVGVVEPVPHDETYCDPASLFHVSNDYSFIRYYTRTLYQFQF QEALCQAAKHEGPLHKCDISNSTEAGQKLFNMLRLGKSEPWTLALENVVGAK NMNVRPLLNYFEPLFTWLKDQNKNSFVGWSTDWSPYADSGGGGSGGYIPEAPR DGQAYVRKDGEWVLLSTFLGGSHHHHHH |

TABLE 4

Additional modified constructs

| SEQ ID NO: | Construct | Sequence |
|---|---|---|
| 23 | Sol-ACE2-Foldon-C275-C448-X27-X34-X353* *X27 is T, W, or Y; X34 is H, F, or W; X353 is K, W, or Y | MSSSSWLLLSLVAVTAAQSTIEEQAKXFLDKFNXEAEDLFYQSSLASWNYNTNI TEENVQNMNNAGDKWSAFLKEQSTLAQMYPLQEIQNLTVKLQLQALQQNGSS VLSEDKSKRLNTILNTMSTIYSTGKVCNPDNPQECLLLEPGLNEIMANSLDYNE RLWAWESWRSEVGKQLRPLYEEYVVLKNEMARANHYEDYGDYWRGDYEVN GVDGYDYSRGQLIEDVEHTFEEIKPLYEHLHAYVRAKLMNAYPSYISPIGCLPA HLLGDMWGRFCTNLYSLTVPFGQKPNIDVTDAMVDQAWDAQRIFKEAEKFFV SVGLPNMTQGFWENSMLTDPGNVQKAVCHPTAWDLGXGDFRILMCTKVTMD DFLTAHHEMGHIQYDMAYAAQPFLLRNGANEGFHEAVGEIMSLSAATPKHLK SIGLLSPDFQEDNETEINFLLKQALTIVCTLPFTYMLEKWRWMVFKGEIPKDQW MKKWWEMKREIVGVVEPVPHDETYCDPASLFHVSNDYSFIRYYTRTLYQFQF QEALCQAAKHEGPLHKCDISNSTEAGQKLFNMLRLGKSEPWTLALENVVGAK NMNVRPLLNYFEPLFTWLKDQNKNSFVGWSTDWSPYADSGGGGSGGYIPEAP RDGQAYVRKDGEWVLLSTFLGGSHHHHHH |
| 24 | Sol-ACE2-Foldon-C377-C408-X27-X34-X353* *X27 is T, W, or Y; X34 is H, F, or | MSSSSWLLLSLVAVTAAQSTIEEQAKXFLDKFNXEAEDLFYQSSLASWNYNTNI TEENVQNMNNAGDKWSAFLKEQSTLAQMYPLQEIQNLTVKLQLQALQQNGSS VLSEDKSKRLNTILNTMSTIYSTGKVCNPDNPQECLLLEPGLNEIMANSLDYNE RLWAWESWRSEVGKQLRPLYEEYVVLKNEMARANHYEDYGDYWRGDYEVN GVDGYDYSRGQLIEDVEHTFEEIKPLYEHLHAYVRAKLMNAYPSYISPIGCLPA HLLGDMWGRFWTNLYSLTVPFGQKPNIDVTDAMVDQAWDAQRIFKEAEKFFV |

TABLE 4-continued

Additional modified constructs

| SEQ ID NO: | Construct | Sequence |
|---|---|---|
| | W; X353 is K, W,<br>or Y | SVGLPNMTQGFWENSMLTDPGNVQKAVCHPTAWDLGXGDFRILMCTKVTMD<br>DFLTAHHEMCHIQYDMAYAAQPFLLRNGANEGFHEAVGEICSLSAATPKHLKS<br>IGLLSPDFQEDNETEINFLLKQALTIVGTLPFTYMLEKWRWMVFKGEIPKDQW<br>MKKWWEMKREIVGVVEPVPHDETYCDPASLFHVSNDYSFIRYYTRTLYQFQF<br>QEALCQAAKHEGPLHKCDISNSTEAGQKLFNMLRLGKSEPWTLALENVVGAK<br>NMNVRPLLNYFEPLFTWLKDQNKNSFVGWSTDWSPYADSGGGGSGGYIPEAP<br>RDGQAYVRKDGEWVLLSTFLGGSHHHHHH |
| 25 | Sol-ACE2-<br>Foldon-C523-<br>C583-X27-<br>X34-X353*<br>*X27 is T, W, or<br>Y; X34 is H, F, or<br>W; X353 is K, W,<br>or Y | MSSSSWLLLSLVAVTAAQSTIEEQAKXFLDKFNXEAEDLFYQSSLASWNYNTNI<br>TEENVQNMNNAGDKWSAFLKEQSTLAQMYPLQEIQNLTVKLQLQALQQNGSS<br>VLSEDKSKRLNTILNTMSTIYSTGKVCNPDNPQECLLLEPGLNEIMANSLDYNE<br>RLWAWESWRSEVGKQLRPLYEEYVVLKNEMARANHYEDYGDYWRGDYEVN<br>GVDGYDYSRGQLIEDVEHTFEEIKPLYEHLHAYVRAKLMNAYPSYISPIGCLPA<br>HLLGDMWGRFWTNLYSLTVPFGQKPNIDVTDAMVDQAWDAQRIFKEAEKFFV<br>SVGLPNMTQGFWENSMLTDPGNVQKAVCHPTAWDLGXGDFRILMCTKVTMD<br>DFLTAHHEMGHIQYDMAYAAQPFLLRNGANEGFHEAVGEIMSLSAATPKHLK<br>SIGLLSPDFQEDNETEINFLLKQALTIVGTLPFTYMLEKWRWMVFKGEIPKDQW<br>MKKWWEMKREIVGVVEPVPHDETYCDPASLFHVSNDYSFIRYYTRTLYQCQF<br>QEALCQAAKHEGPLHKCDISNSTEAGQKLFNMLRLGKSEPWTLALENVVGAK<br>NMNVRCLLNYFEPLFTWLKDQNKNSFVGWSTDWSPYADSGGGGSGGYIPEAP<br>RDGQAYVRKDGEWVLLSTFLGGSHHHHHH |
| 26 | Sol-ACE2-<br>Foldon-C523-<br>C584-X27-<br>X34-X353*<br>*X27 is T, W, or<br>Y; X34 is H, F, or<br>W; X353 is K, W,<br>or Y | MSSSSWLLLSLVAVTAAQSTIEEQAKXFLDKFNXEAEDLFYQSSLASWNYNTNI<br>TEENVQNMNNAGDKWSAFLKEQSTLAQMYPLQEIQNLTVKLQLQALQQNGSS<br>VLSEDKSKRLNTILNTMSTIYSTGKVCNPDNPQECLLLEPGLNEIMANSLDYNE<br>RLWAWESWRSEVGKQLRPLYEEYVVLKNEMARANHYEDYGDYWRGDYEVN<br>GVDGYDYSRGQLIEDVEHTFEEIKPLYEHLHAYVRAKLMNAYPSYISPIGCLPA<br>HLLGDMWGRFWTNLYSLTVPFGQKPNIDVTDAMVDQAWDAQRIFKEAEKFFV<br>SVGLPNMTQGFWENSMLTDPGNVQKAVCHPTAWDLGXGDFRILMCTKVTMD<br>DFLTAHHEMGHIQYDMAYAAQPFLLRNGANEGFHEAVGEIMSLSAATPKHLK<br>SIGLLSPDFQEDNETEINFLLKQALTIVGTLPFTYMLEKWRWMVFKGEIPKDQW<br>MKKWWEMKREIVGVVEPVPHDETYCDPASLFHVSNDYSFIRYYTRTLYQCQF<br>QEALCQAAKHEGPLHKCDISNSTEAGQKLFNMLRLGKSEPWTLALENVVGAK<br>NMNVRPCLNYFEPLFTWLKDQNKNSFVGWSTDWSPYADSGGGGSGGYIPEAP<br>RDGQAYVRKDGEWVLLSTFLGGSHHHHHH |
| 27 | Sol-ACE2-<br>Foldon-C275-<br>C448-C377-<br>C408-X27-<br>X34-X353*<br>*X27 is T, W, or<br>Y; X34 is H, F, or<br>W; X353 is K, W,<br>or Y | MSSSSWLLLSLVAVTAAQSTIEEQAKXFLDKFNXEAEDLFYQSSLASWNYNTN<br>ITEENVQNMNNAGDKWSAFLKEQSTLAQMYPLQEIQNLTVKLQLQALQQNGS<br>SVLSEDKSKRLNTILNTMSTIYSTGKVCNPDNPQECLLLEPGLNEIMANSLDYN<br>ERLWAWESWRSEVGKQLRPLYEEYVVLKNEMARANHYEDYGDYWRGDYE<br>VNGVDGYDYSRGQLIEDVEHTFEEIKPLYEHLHAYVRAKLMNAYPSYISPIGC<br>LPAHLLGDMWGRFCTNLYSLTVPFGQKPNIDVTDAMVDQAWDAQRIFKEAE<br>KFFVSVGLPNMTQGFWENSMLTDPGNVQKAVCHPTAWDLGXGDFRILMCTK<br>VTMDDFLTAHHEMCHIQYDMAYAAQPFLLRNGANEGFHEAVGEICSLSAATP<br>KHLKSIGLLSPDFQEDNETEINFLLKQALTIVCTLPFTYMLEKWRWMVFKGEIP<br>KDQWMKKWWEMKREIVGVVEPVPHDETYCDPASLFHVSNDYSFIRYYTRTL<br>YQFQFQEALCQAAKHEGPLHKCDISNSTEAGQKLFNMLRLGKSEPWTLALEN<br>VVGAKNMNVRPLLNYFEPLFTWLKDQNKNSFVGWSTDWSPYADSGGGGSGG<br>YIPEAPRDGQAYVRKDGEWVLLSTFLGGSHHHHHH |
| 28 | Sol-ACE2-<br>Foldon-C275-<br>C448-C523-<br>C583-X27-<br>X34-X353*<br>*X27 is T, W, or<br>Y; X34 is H, F, or<br>W; X353is K, W,<br>or Y | MSSSSWLLLSLVAVTAAQSTIEEQAKXFLDKFNXEAEDLFYQSSLASWNYNTNI<br>TEENVQNMNNAGDKWSAFLKEQSTLAQMYPLQEIQNLTVKLQLQALQQNGSS<br>VLSEDKSKRLNTILNTMSTIYSTGKVCNPDNPQECLLLEPGLNEIMANSLDYNE<br>RLWAWESWRSEVGKQLRPLYEEYVVLKNEMARANHYEDYGDYWRGDYEVN<br>GVDGYDYSRGQLIEDVEHTFEEIKPLYEHLHAYVRAKLMNAYPSYISPIGCLPA<br>HLLGDMWGRFCTNLYSLTVPFGQKPNIDVTDAMVDQAWDAQRIFKEAEKFFV<br>SVGLPNMTQGFWENSMLTDPGNVQKAVCHPTAWDLGXGDFRILMCTKVTMD<br>DFLTAHHEMGHIQYDMAYAAQPFLLRNGANEGFHEAVGEIMSLSAATPKHLK<br>SIGLLSPDFQEDNETEINFLLKQALTIVCTLPFTYMLEKWRWMVFKGEIPKDQW<br>MKKWWEMKREIVGVVEPVPHDETYCDPASLFHVSNDYSFIRYYTRTLYQCQF<br>QEALCQAAKHEGPLHKCDISNSTEAGQKLFNMLRLGKSEPWTLALENVVGAK<br>NMNVRCLLNYFEPLFTWLKDQNKNSFVGWSTDWSPYADSGGGGSGGYIPEAP<br>RDGQAYVRKDGEWVLLSTFLGGSHHHHHH |
| 29 | Sol-ACE2-<br>Foldon-C275-<br>C448-C523-<br>C584-X27-<br>X34-X353*<br>*X27 is T, W, or<br>Y; X34 is H, F, or<br>W; X353is K, W,<br>or Y | MSSSSWLLLSLVAVTAAQSTIEEQAKXFLDKFNXEAEDLFYQSSLASWNYNTNI<br>TEENVQNMNNAGDKWSAFLKEQSTLAQMYPLQEIQNLTVKLQLQALQQNGSS<br>VLSEDKSKRLNTILNTMSTIYSTGKVCNPDNPQECLLLEPGLNEIMANSLDYNE<br>RLWAWESWRSEVGKQLRPLYEEYVVLKNEMARANHYEDYGDYWRGDYEVN<br>GVDGYDYSRGQLIEDVEHTFEEIKPLYEHLHAYVRAKLMNAYPSYISPIGCLPA<br>HLLGDMWGRFCTNLYSLTVPFGQKPNIDVTDAMVDQAWDAQRIFKEAEKFFV<br>SVGLPNMTQGFWENSMLTDPGNVQKAVCHPTAWDLGXGDFRILMCTKVTMD<br>DFLTAHHEMGHIQYDMAYAAQPFLLRNGANEGFHEAVGEIMSLSAATPKHLK<br>SIGLLSPDFQEDNETEINFLLKQALTIVCTLPFTYMLEKWRWMVFKGEIPKDQW<br>MKKWWEMKREIVGVVEPVPHDETYCDPASLFHVSNDYSFIRYYTRTLYQCQF |

TABLE 4-continued

Additional modified constructs

| SEQ ID NO: | Construct | Sequence |
|---|---|---|
| | | QEALCQAAKHEGPLHKCDISNSTEAGQKLFNMLRLGKSEPWTLALENVVGAK NMNVRPCLNYFEPLFTWLKDQNKNSFVGWSTDWSPYADSGGGGSGGYIPEAP RDGQAYVRKDGEWVLLSTFLGGSHHHHHH |
| 30 | Sol-ACE2-Foldon-C377-C408-C523-C58 -X27 -X34-X353* *X27 is T, W, or Y; X34 is H, F, or W; X353is K, W, or Y | MSSSSWLLLS include so-called "point of care (POC) diagnostic tests," which could play a role in rapidly screening of suspected individuals in large numbers (see Kozel, T. R. & Burnham-Marusich, A. R. Point-of-Care Testing for Infectious Diseases: Past, Present, and Future. J Clin Microbiol 55, 2313-2320 (2017), and Vashist, S. K. Point-of-Care Diagnostics: Recent Advances and Trends. *Biosensors* (*Basel*) 7(2017)). Identifying the best antibodies suitable for POC assays requires trial and error, however, and it is also difficult to modulate the binding kinetics of antibody-antigen interaction once an antibody is selected.

Lateral flow immunoassays are POC diagnostic tests that rely on the unidirectional flow of a sample forming complexes with a gold nanoparticle-conjugated ligand, which then can be captured by the immobilized ligand (test line) and an immobilized reagent that can bind the same ligand (control line), respectively (FIG. 6). An optimized lateral flow assay can be simple, fast, inexpensive and user-friendly, yet with high sensitivity and specificity. A typical test strip has four key components: a sample application pad, a conjugate release pad, a nitrocellulose membrane and an absorption pad (FIG. 6). The ACE2 constructs as described herein with the improved binding properties to the spike (S) protein on the virion surface can be used in a rapid lateral flow diagnostic test. Recent studies indicate that the viral load early after symptom onset of respiratory samples (nasal and throat swabs, and sputum) from SARS-CoV-2 infected patients can be quite high ($>1 \times 10^6$ copies/ml), making desirable a test kit for the detection sensitivity required for clinical diagnosis (see Pan, Y., Zhang, D., Yang, P., Poon, L. L. M. & Wang, Q. Viral load of SARS-CoV-2 in clinical samples. *Lancet Infect Dis* (2020), and Zou, L. et al. SARS-CoV-2 Viral Load in Upper Respiratory Specimens of Infected Patients. *N Engl J Med* 382, 1177-1179 (2020)).

Example 3. Diagnostic Methods to Detect SARS-CoV-2 Infection

The ACE2 constructs as described herein can be used in other diagnostic methods. For example, the ACE2 constructs as described herein with the improved binding properties to the spike (S) protein on the virion surface can be incorporated into a facemask. The facemask can serve to detect the binding of virions. As one example, when a subject is infected with the SARS-CoV-2 virus, the ACE2 constructs incorporated into the facemask will react with the spike proteins found on the virion surface as they are expelled from the subject. The ACE2 constructs can also be used in ELISA-based assays to detect the virus or evidence of the virus in a subject.

Example 4. Therapeutic and Prophylactic Methods to Treat SARS-CoV-2 Infection

The ACE2 constructs as described herein can be used in therapeutic methods to treat or prevent a SARS-CoV2 infection, or infection with other viruses that also bind ACE2. For example, ACE2 constructs of the present invention, including those in soluble form, could be used inhibit the interaction between the SARS-CoV-2 virion and ACE2 in the lungs and other organs of a subject.

Example 5. A Trimeric Human Angiotensin-Converting Enzyme 2 as an Anti-SARS-CoV-2 Agent The COVID-19 pandemic, caused by severe acute respiratory syndrome coronavirus 2 (SARS-CoV-2), has infected more than 29 million people worldwide, leading to over 900 thousand deaths, with devastating socio-economic impacts. Effective intervention strategies are urgently needed to control the pandemic.

Several therapeutic approaches have been evaluated in the hope of providing a viable treatment for COVID-19. While the infection resolves on its own in most asymptomatic and mild cases over time, COVID-19 in severe cases appears to progress in two phases—initial active viral replication in the respiratory system and subsequent excessive immune responses leading to multiple organ failure and possible death(15). Thus, antivirals alone may be insufficient to change the course of disease progression for the population that needs intervention the most if administrated too late.

Human angiotensin-converting enzyme 2 (ACE2) is the cellular receptor for SARS-CoV-2 and binds the receptor binding domain (RBD) of the spike (S) protein of the virus to promote viral entry into the host cells and initiate infection(16-17). It is a type I membrane glycoprotein containing an extracellular ectodomain that has metallopeptidase activity. Its neck domain near the transmembrane anchor mediates dimerization(18). ACE2 is also a key negative regulator of the renin-angiotensin system (RAS)—a major hormone system, conserved in mammals and some other vertebrate animals, for modulating vascular function (19-20). The RAS controls extracellular fluid volume and blood pressure homeostasis by regulating the levels of renin and angiotensins in the circulation. Renin cleaves angiotensinogen to release angiotensin I (Ang I), which can be further processed by angiotensin-converting enzyme (ACE) into angiotensin II (Ang II)—a vasoconstrictive peptide that raises blood pressure and increases the extracellular fluid volume in the body by activating the angiotensin II receptors, including angiotensin II receptor type I (AT1R)(21). ACE2 primarily converts Ang II to angiotensin-(1-7) (Ang 1-7), which is a vasodilator, thereby counter-balancing the effect of ACE/Ang II and playing critical roles in preventing hypertension and tissue damages (22).

The protective roles of ACE2 in acute respiratory distress syndrome (ARDS) and acute lung injury (ALI) have been demonstrated in animal models (23-25). A recombinant soluble human ACE2 (rhACE2) has been reported to block SARS-CoV-2 infection in cell culture and human organoids (26), prompting a phase 2 clinical trial for use of rhACE2 as a treatment for COVID-19 patients (NCT04335136). Thus, administration of exogenous ACE2 may be a promising therapeutic strategy for treating COVID-19, because it could not only block viral spread but also modulate the RAS to prevent organ injury. Therefore, a series of ACE2 variants were designed to enhance their binding affinity for SARS-CoV-2 S protein and their potency in blocking SARS-CoV-2 infection.

Results

Structures of Soluble ACE2 in Complex with SARS-CoV-2 S Protein Trimer

Figure 13A:
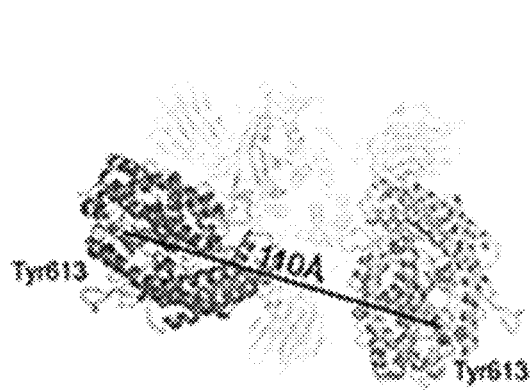
FIGS. 13A-13C show ACE2-S interactions.
Figure 13B:
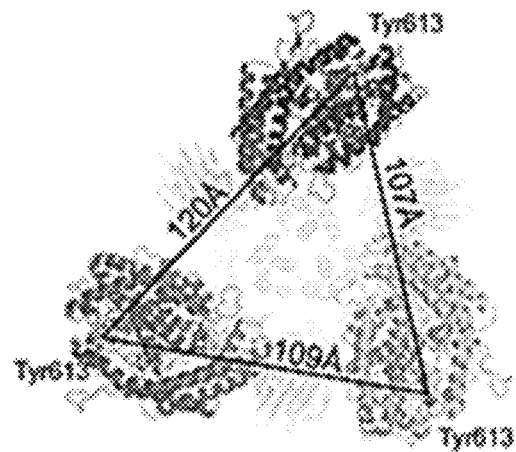
Figure 13C:
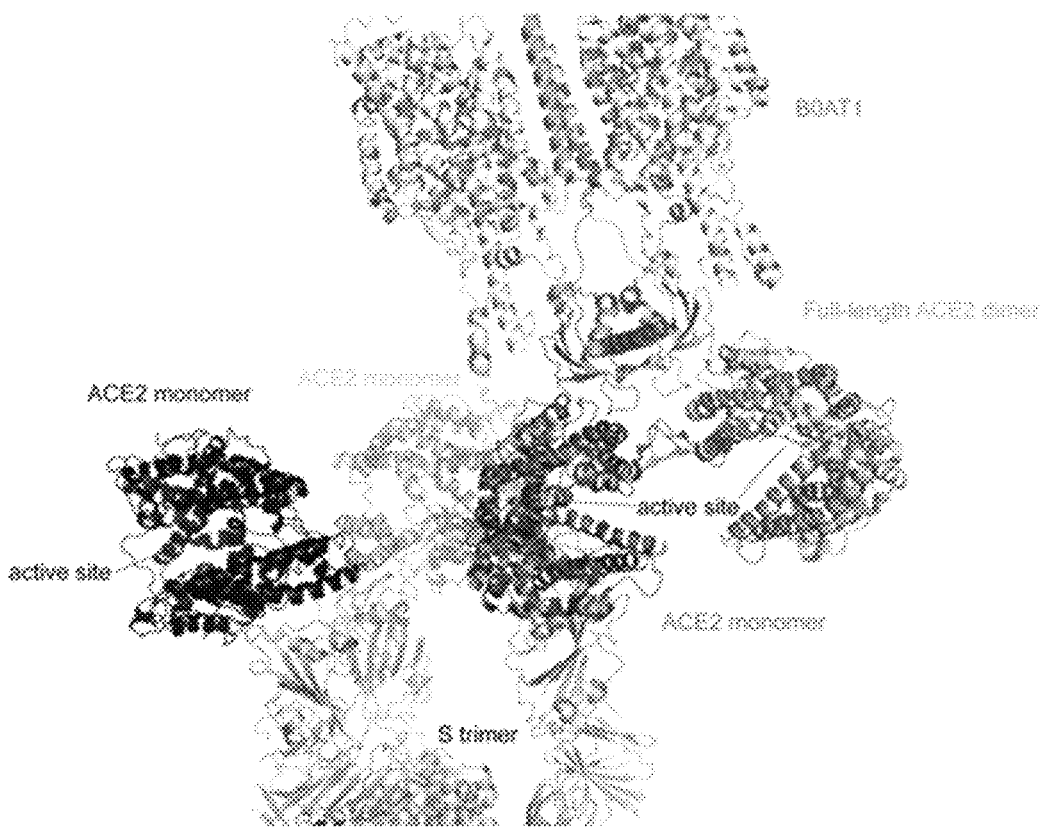
Figure 14:
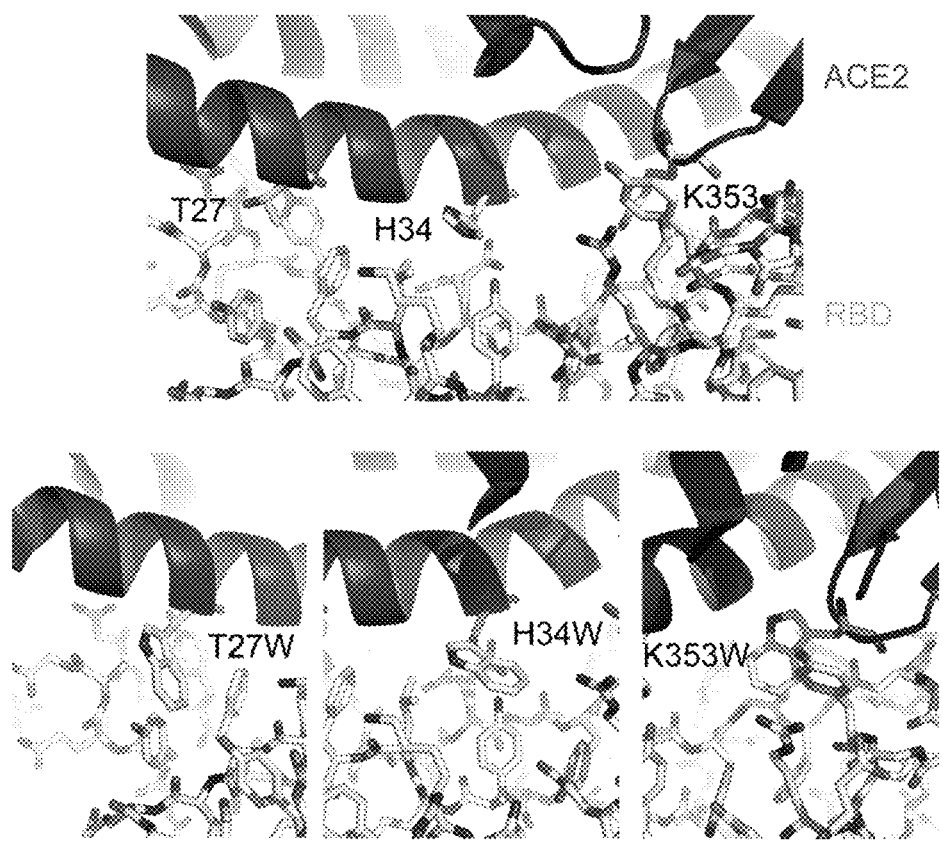
FIG. 14 shows design of mutations at the ACE2-RBD interface. Top, the interface between ACE2 in ribbon diagram in magenta and RBD in stick model from the complex structure (PDB ID: 6M0J) with T27, H34 and K353 from ACE2 indicated. Bottom, modeled T27W, H34W and K353W mutations that may enhance the hydrophobic interactions between ACE2 and RBD.
Figure 15A:
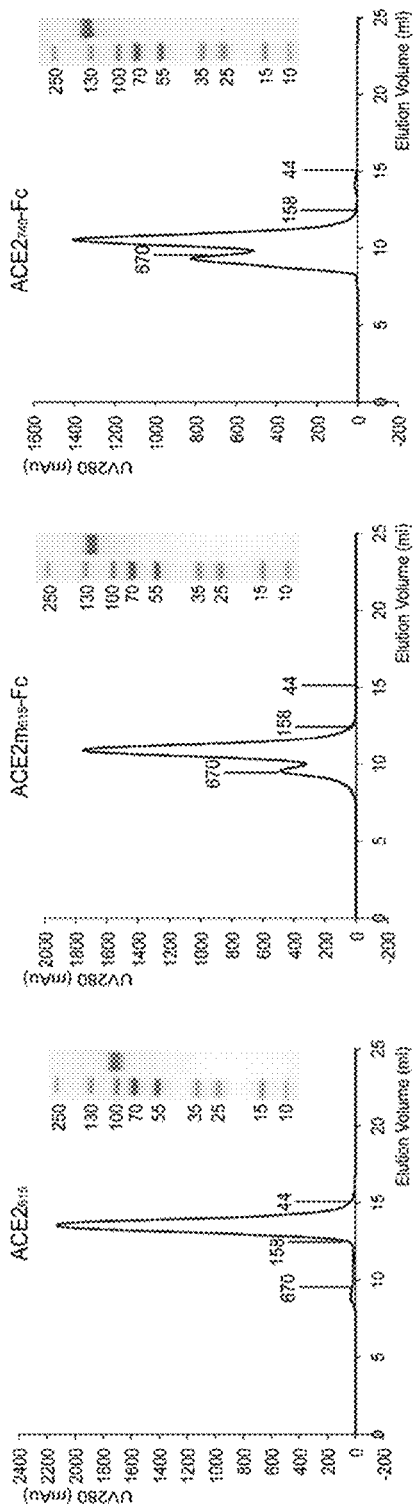
FIGS. 15A-15C show purification of ACE2 variants. The purified ACE2 proteins were resolved by gel-filtration chromatography on a Superdex 200 column. The molecular weight standards include thyoglobulin (670 kDa), γ-globulin (158 kDa) and ovalbumin (44 kDa). Inset, peak fractions were analyzed by Coomassie stained SDS-PAGE.
Figure 15B:
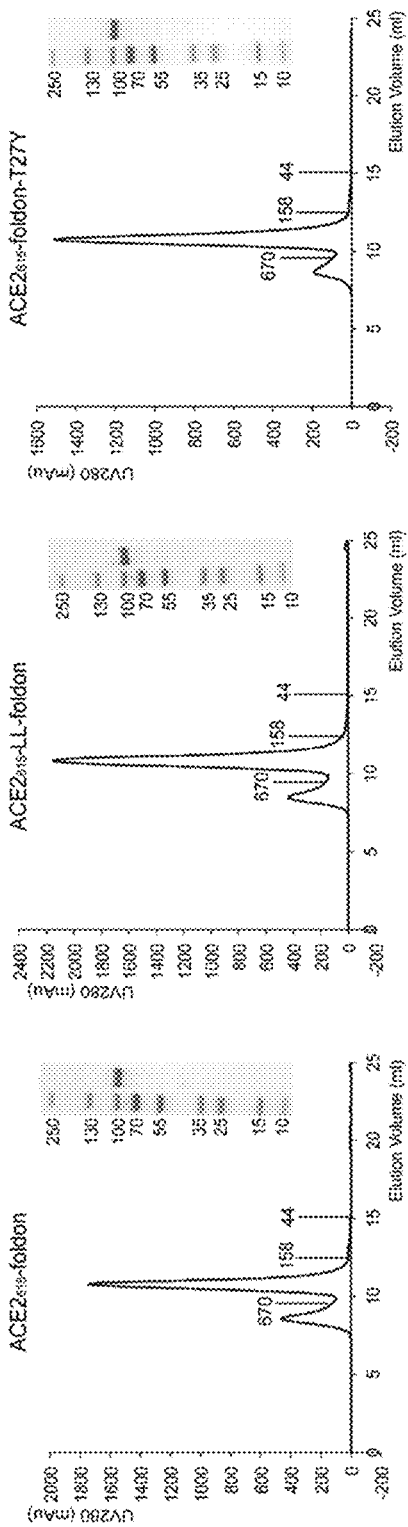
Figure 15C:
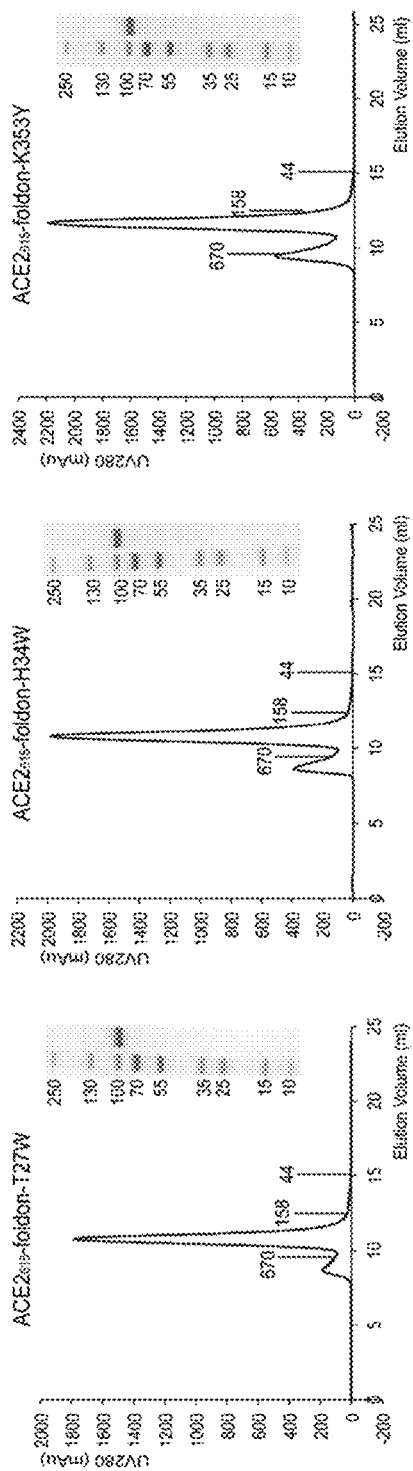
Figure 16:
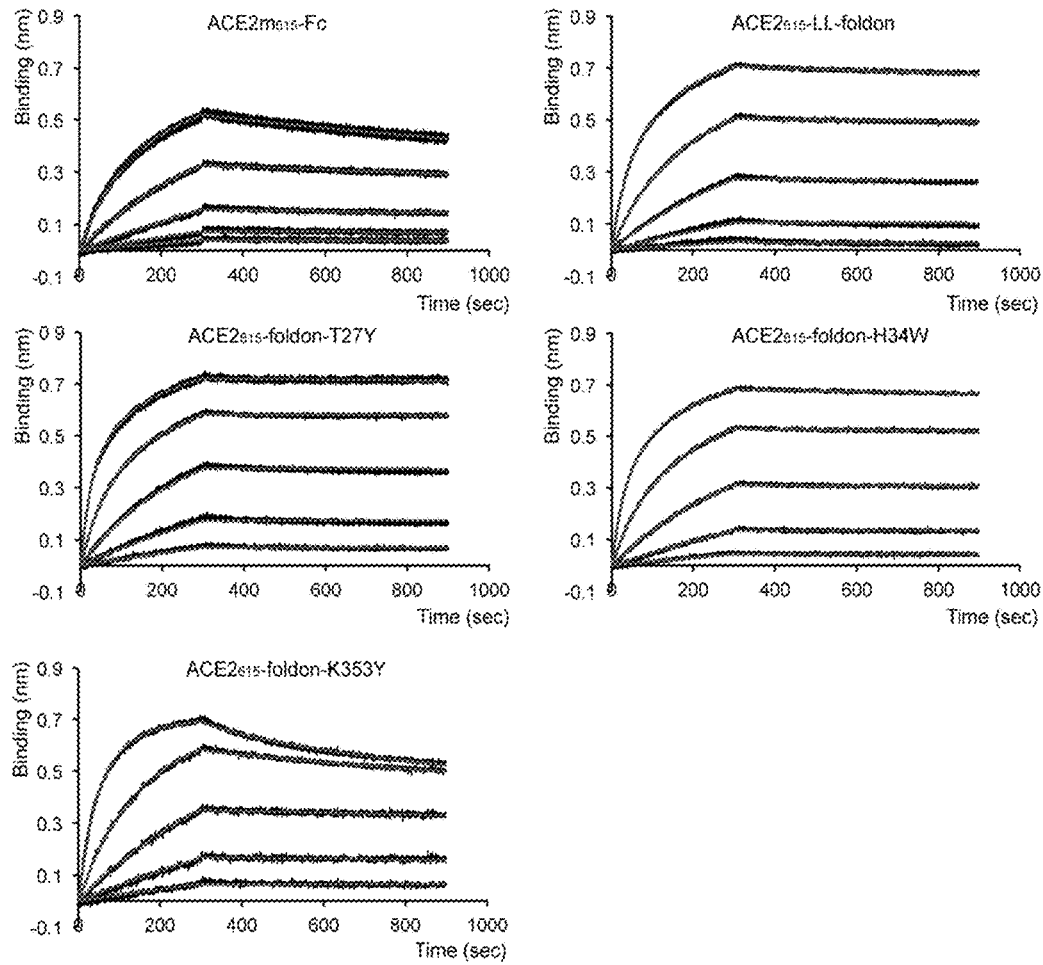
FIG. 16 shows binding of ACE2 variants to the stabilized soluble S trimer by bio-layer interferometry (BLI). The S protein was immobilized and subsequently dipped into the wells containing ACE2 proteins at various concentrations (0.926-75 nM for ACE2615-Fc, 0.617-50 nM for the ACE2615-foldon variants). Binding kinetics was evaluated using a bivalent model for all oligomeric ACE2s. The sensorgrams are in black and the fits in grey. All the experiments were repeated at least twice with essentially identical results. Binding constants derived from the BLI experiments were also summarized.
Figure 17A:
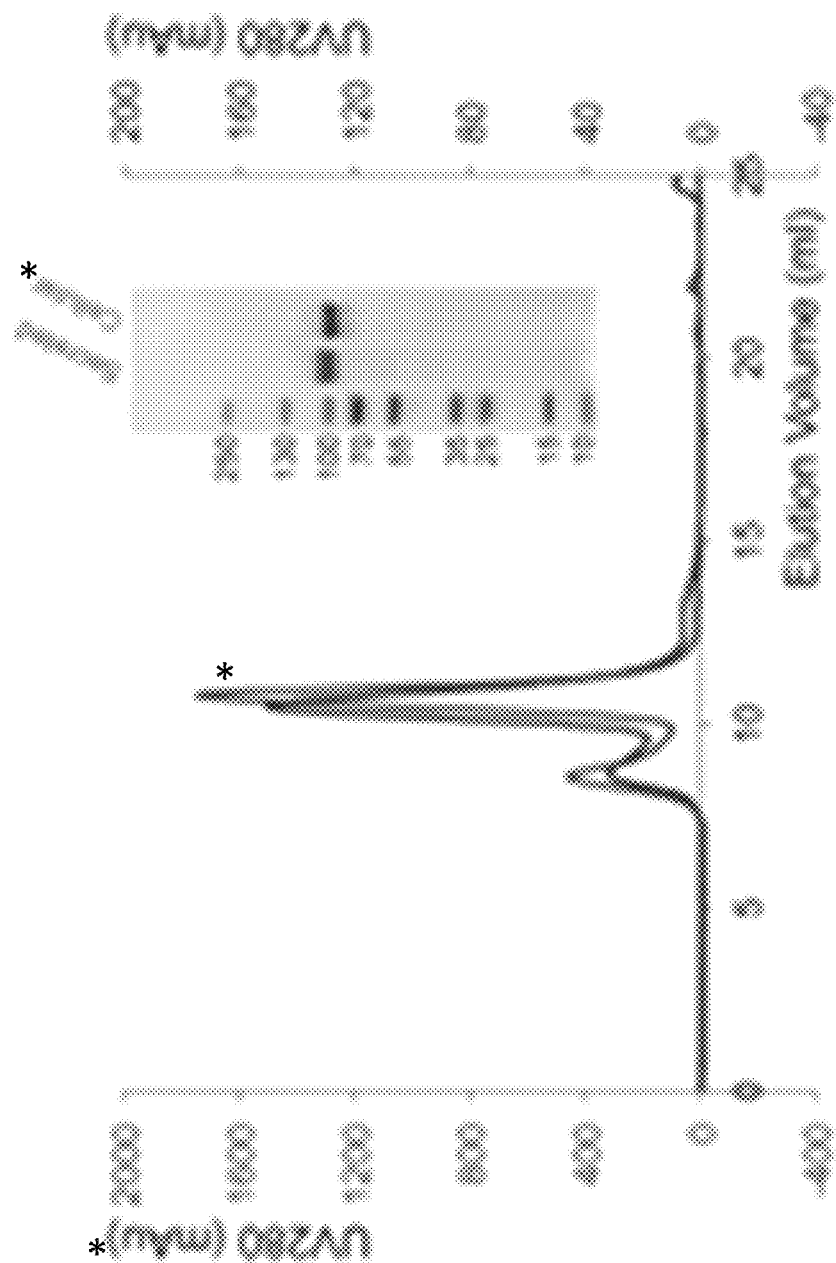
FIGS. 17A-17B show comparison of secreted and cellular ACE2615-foldon protein.
Figure 17B:
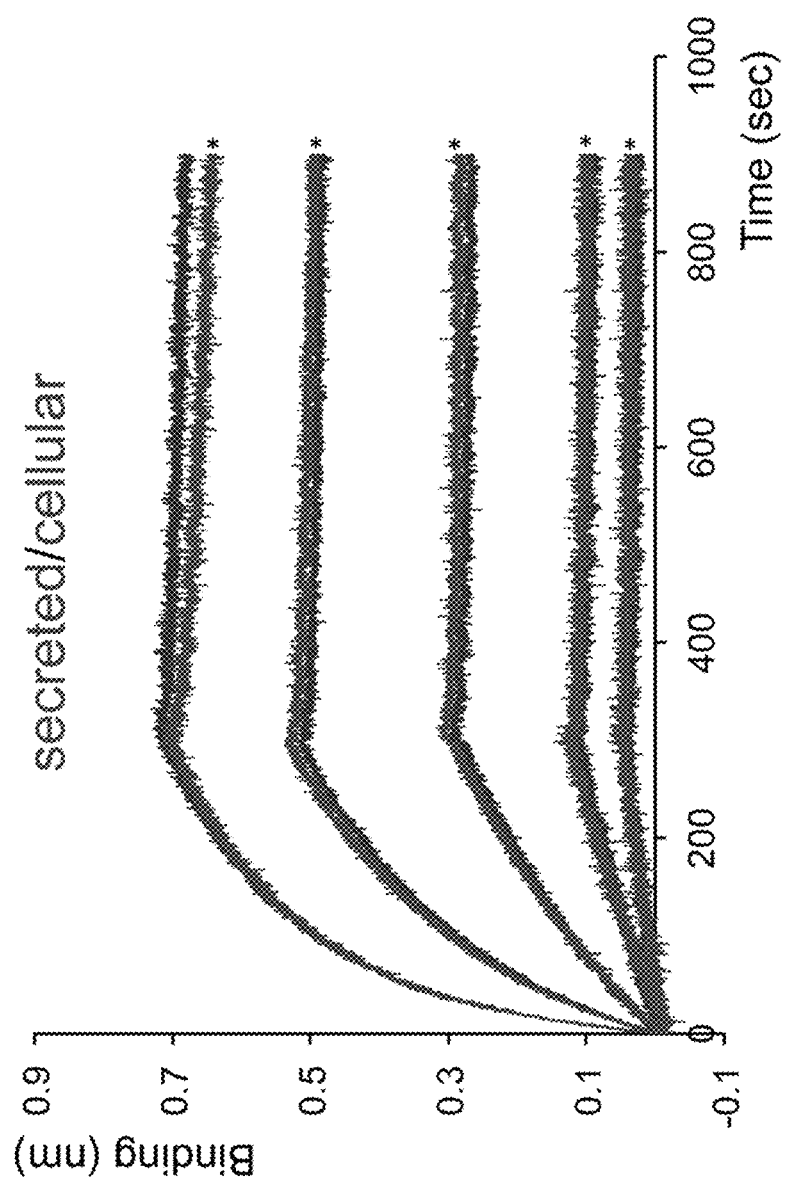

To facilitate design of ACE2-based viral fusion inhibitors, it was first determined, by cryo-EM, the structures of a monomeric soluble ACE2 (residue 18-615) in complex with a stabilized soluble SARS-CoV-2 S protein trimer (FIGS. 1A-1B; ref 27). The complex was prepared by mixing the two proteins because the monomeric ACE2 dissociates from S trimer very rapidly (28). After 3D classification (FIG. 11, FIGS. 12A-12C), four distinct classes were found that represent ACE2-free S trimer in the one-RBD-up conformation, one ACE2 bound S trimer, two ACE2 bound S trimer, and three ACE2 bound S trimer, respectively (FIGS. 7A-7D). Consistent with previous findings with ACE2 binding to SARS-CoV S protein as well as a recent SARS-CoV-2 study (29), ACE2 interacts with the RBD in its up conformation. While the NTD (N-terminal domain) of 51 shifts outwards slightly, the S2 portion remains largely unchanged upon ACE2 binding, even when compared to the recently published structure of the full-length S protein in the closed prefusion conformation (28). The structure of the complex with three ACE2 bound is not symmetrical, as the distances between the C-termini of the three ACE2s (residue Tyr613) are 107 Å, 109 Å and 120 Å, respectively (FIGS. 13A-13C). This distance in the complex with two ACE2s bound is 110 Å. These observations suggest that there is a modest degree of freedom for the up conformation of RBD when ACE2 is bound. All the substrate binding sites of the bound ACE2s face away from the threefold axis of the S trimer (FIGS. 13A-13C), incompatible with the structure of the full length ACE2 dimer in complex with the amino acid transporter B$^0$AT1, in which the two active sites of the two protomers are facing each other (18). If the B$^0$AT1-bound ACE2 dimer is indeed the form recognized by SARS-CoV-2, it appears that only one ACE2 protomer in the dimer can bind one RBD in an S trimer unless there are unexpectedly large structural rearrangements in either ACE2 or S.

Design of ACE2 Variants to Enhance its Binding Affinity to SARS-CoV-2 S Trimer

Measurements of the binding kinetics of soluble monomeric ACE2 ($ACE2_{615}$; FIGS. 8A-8C) to the SARS-CoV-2 S trimer shows a relatively fast dissociation rate (28), limiting its ability to compete with the membrane bound ACE2 on the surface of a target cell. Therefore, the effective affinity was enhanced by creating a trimeric form of soluble ACE2. A trimerization foldon tag was fused, derived from bacteriophage T4 fibritin (30), to the C-terminal end of the ACE2 peptidase domain (residue 615) through a 11-residue flexible linker, a construct referred to as $ACE2_{615}$-foldon (FIGS. 8A-8C). Another version ($ACE2_{615}$-LL-foldon) was also created with a slightly longer linker (LL) with 13 residues between ACE2 and the foldon tag to assess its impact on binding. To further strengthen the interaction between ACE2 and the RBD, mutations were introduced guided by high-resolution structures (FIG. 14; ref (31)), at three different positions in the ACE2-RBD interface—T27, H34 and K353, respectively. Substitution with a bulky hydrophobic residue at each of these sites may enhance hydrophobic interactions between the two proteins and slow the dissociation (FIG. 14). Five mutants were designed, T27Y, T27W, H34W, K353Y and K353W, in the $ACE2_{615}$-foldon background. Finally, for comparison, two versions of dimeric forms were also included, $ACE2m_{615}$-Fc and $ACE2_{740}$-Fc, both fused to an Fc domain of an immunoglobulin G (FIG. 8A). $ACE2m_{615}$-Fc contains H374N and H378N mutations at its peptidase active site and ACE2740-Fc includes the neck domain that mediates dimerization in the full length ACE2 (18).

To produce the soluble recombinant ACE2 and its variants, HEK293 cells were transfected with the expression constructs of the monomeric and trimeric forms containing a C-terminal his tag and purified the proteins by Ni-NTA and gel filtration chromatography. The two dimeric forms were purified by protein G resin followed by gel filtration chromatography. While the monomeric and dimeric forms of soluble ACE2 were mostly secreted into cell medium, as judged by western blot, the trimeric $ACE2_{615}$-foldon and its mutants were largely retained inside the cells. The secreted monomer and dimers were purified from the cell supernatants and all the trimers from the cell lysates. Most proteins eluted from a size-exclusion column as a major symmetrical peak, regardless their secretion status (FIGS. 15A-15C). The $ACE2_{740}$-Fc protein containing the dimerizing neck domain appeared to aggregate substantially more than other constructs. The $ACE2_{615}$-foldon K353W mutant aggregated completely, and was not pursued any further. Only the fractions from the major peak for each construct were pooled and used for subsequent analyses. The secreted $ACE2_{615}$-foldon was also compared with the form purified from the cells and their biochemical properties were almost identical (FIGS. 17A-17B).

Binding to SARS-CoV-2 Soluble S Trimer

Next, the binding of these recombinant ACE2 constructs to the stabilized soluble S trimer was measured by bio-layer interferometry (BLI). As shown in FIG. 8A and FIG. 16, the monomeric $ACE2_{615}$ had a fast dissociation rate and a $K_D$ of 77 nM, consistent with the measurement that was reported recently using surface plasmon resonance (SPR; ref (28)). The dimeric $ACE2m_{615}$-FC bound slightly more tightly ($K_D$~22 nM). The dimeric $ACE2_{740}$-Fc also bound more strongly than did the monomer ($K_D$~12 nM), although the dimer formed by the neck domain is not compatible with two ACE2 peptidase domains interacting with two distinct RBDs in a single S trimer (FIGS. 13A-13C). A possible explanation is that the neck domain mediated dimerization is not very strong and that the ACE2 peptidase domains are much more flexible than what the full-length ACE2 structure has indicated (18), particularly in the absence of $B^0AT1$. The trimeric $ACE2_{615}$-foldon interacted with the S trimer much more strongly than any of the monomeric or dimeric forms, with a $K_D$ of 1.2 nM. $ACE2_{615}$-LL-foldon with a longer linker between ACE2 and foldon showed an additional modest affinity enhancement ($K_D$~0.62 nM). The two interface mutants, $ACE2_{615}$-foldon-T27W and $ACE2_{615}$-foldon-T27Y, bound substantially more tightly than did the trimeric wild-type ACE2, with $K_D$s of ~60 and ~90 pM, respectively. While the H34W afforded a slight affinity increase, the K353Y mutation decreased affinity by more than 25-fold. Overall, these data show that the structure-guided design to increase the affinity of ACE2 to the S trimer, by trimerizing the receptor and by modifying the interface, was effective.

ACE2 Peptidase Activity and AT1R Activation

Two independent assays were performed to determine the enzymatic activity of these ACE2 constructs. First, the peptidase activity was measured using a synthetic peptide substrate that releases a free fluorophore upon ACE2 cleavage. In FIG. 9A, concentrations of all the proteins were normalized based on the number of active sites, and the fluorophore release was monitored continuously up to ~40 min. While all the trimeric forms showed essentially the same specific activity, the monomeric $ACE2_{615}$ and the dimeric $ACE2_{740}$-Fc had lower specific activities. The $ACE2m_{615}$-Fc was inactive due to the mutations at the active site. Thus, all these ACE2 constructs with the wild-type sequence at the active site retained their wildtype peptidase activity.

To further support this conclusion, the ability of the ACE2 constructs to block Ang II-induced activation of AT1R was tested. In FIG. 9B, an Ang II peptide was first directly incubated with various ACE2 proteins and then added to HEK293 cells transfected with an AT1R expression construct. Activation of AT1R was monitored by changes in the intracellular calcium concentration. When the digestion reaction was quenched by EDTA at time 0 as a control, all the mixtures with different ACE2 proteins could efficiently activate AT1R, suggesting that nothing in the protein preparations inhibited Ang II-mediated AT1R activation. In contrast, when the digestion was allowed to proceed for 40 min, all ACE2 constructs except for the inactive ACE2m$_{615}$-Fc effectively blocked AT1R activation, presumably by converting Ang II to Ang 1-7, in agreement with the peptidase activity results.

Inhibition of SARS-CoV-2 Infectivity in Cell Culture

Figure 10A:
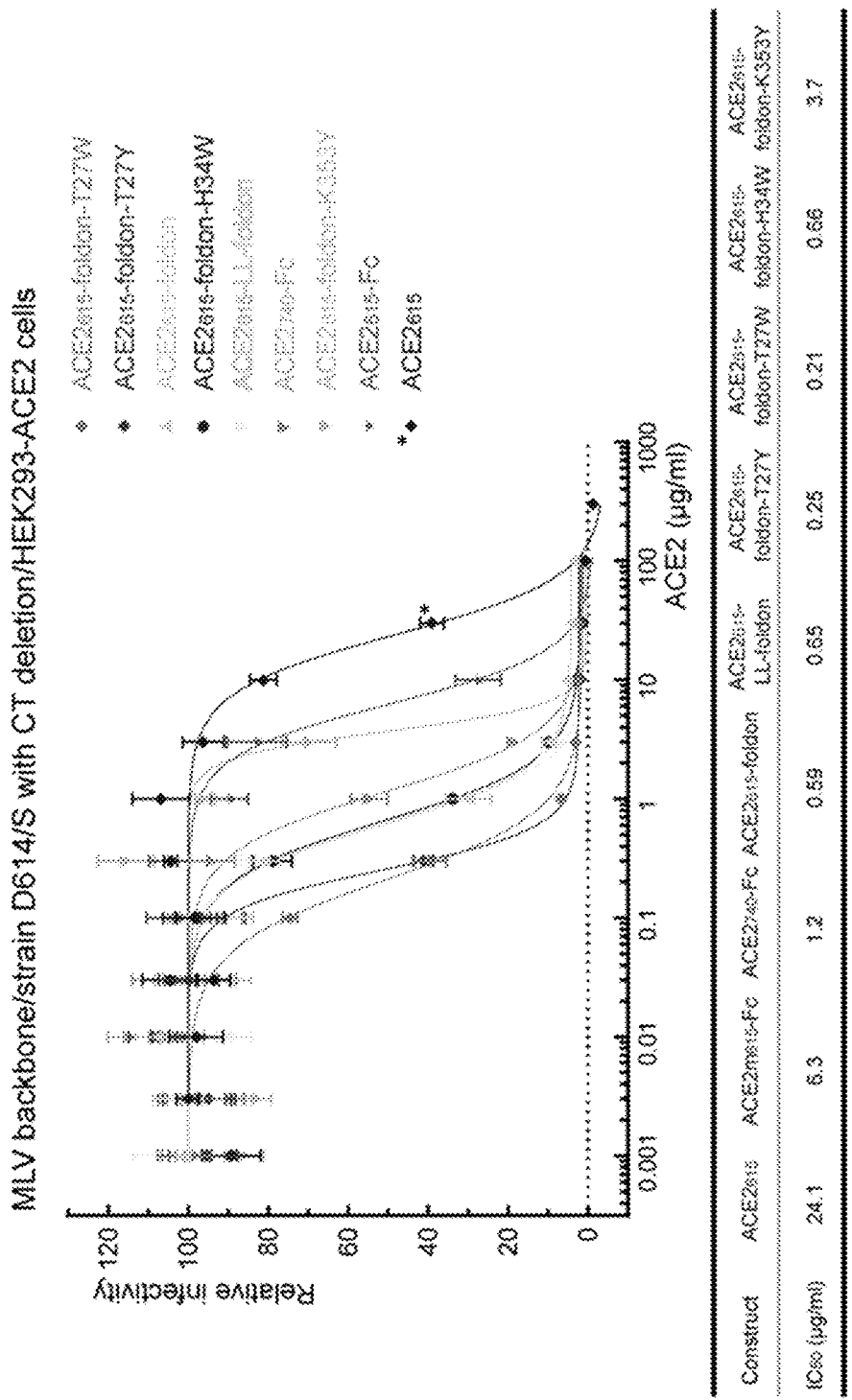
FIGS. 10A-10C show inhibition of SARS-CoV-2 pseudoviruses and authentic viruses by ACE2 variants.
Figure 10B:
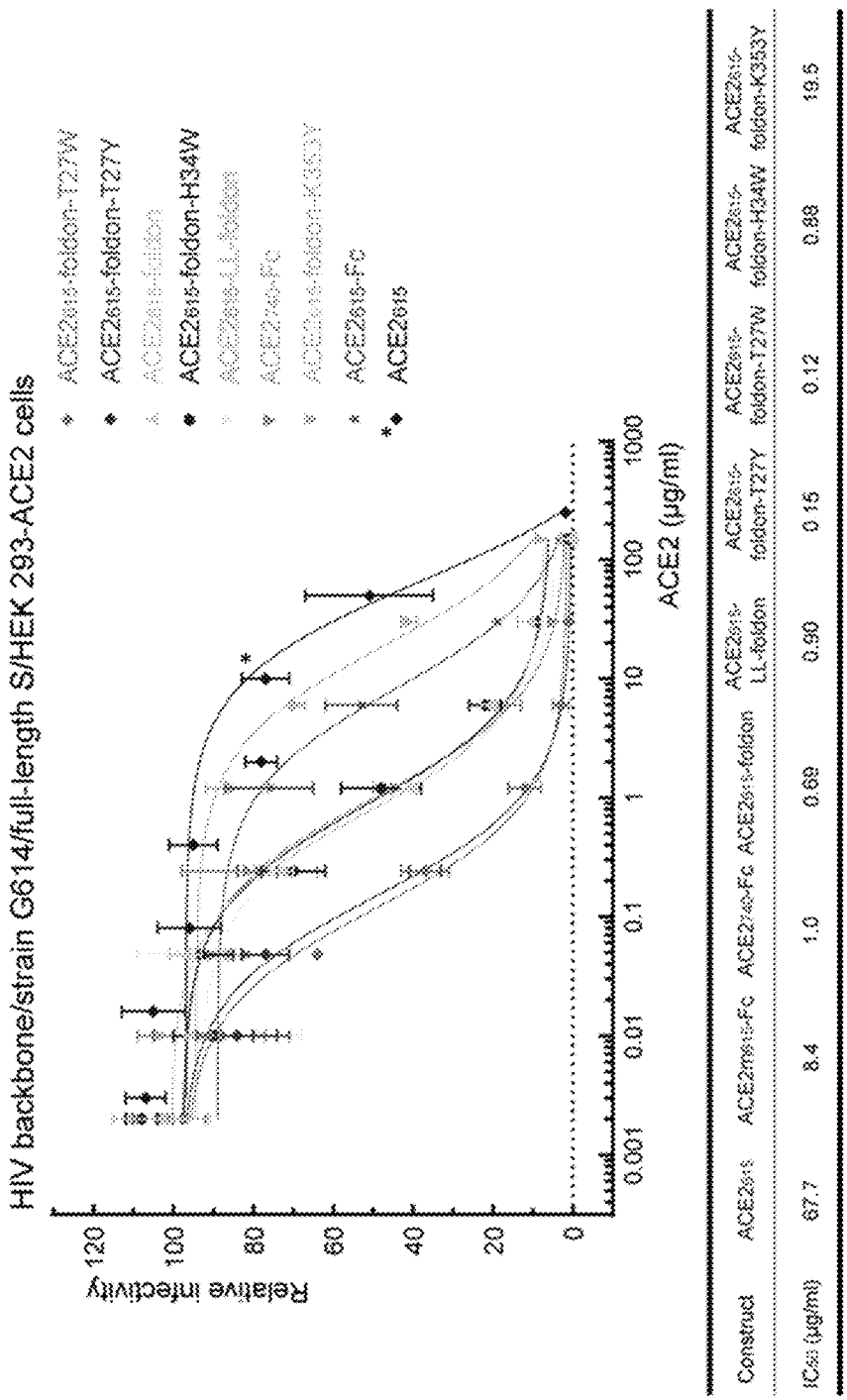
Figure 10C:
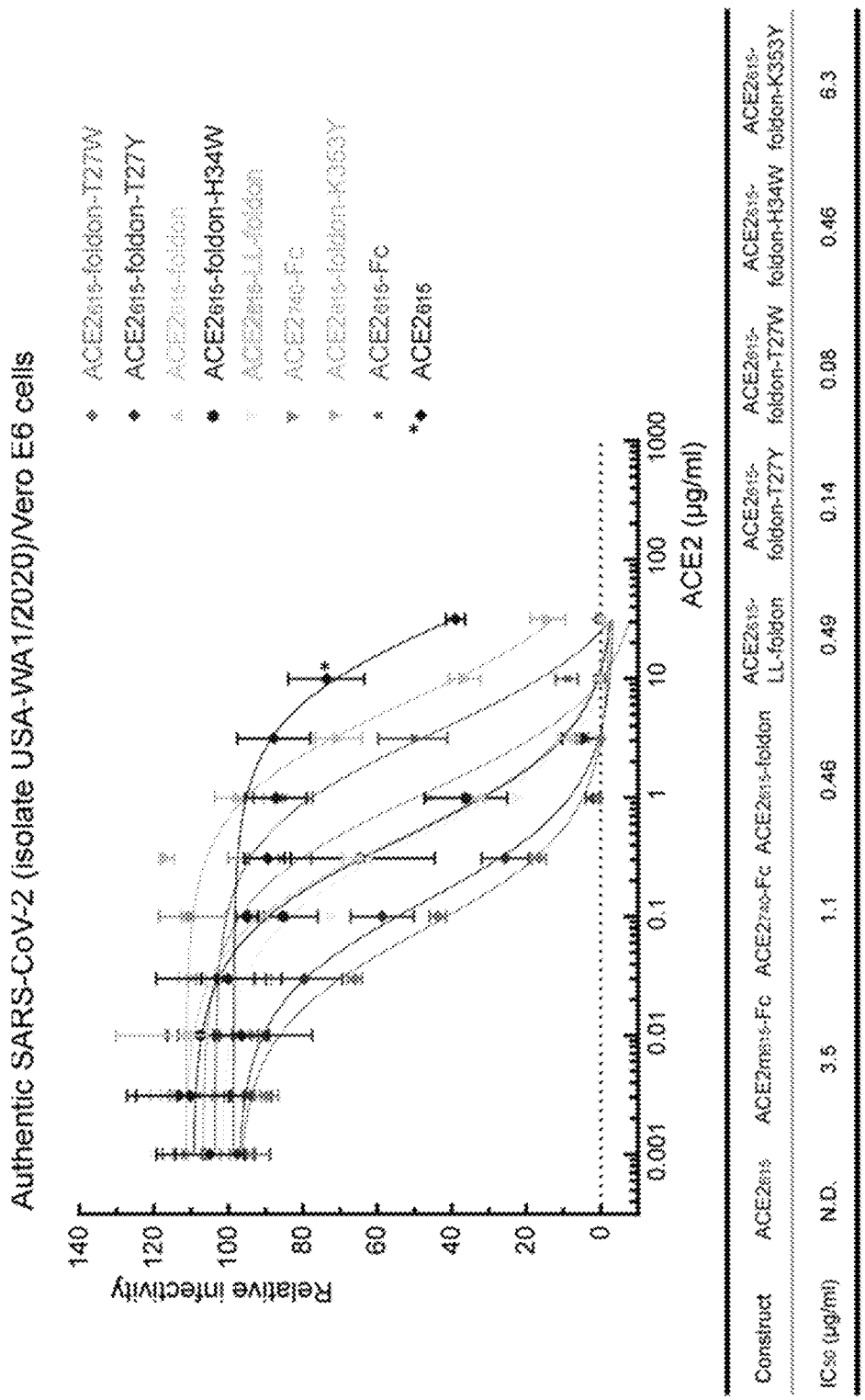
Figure 11:
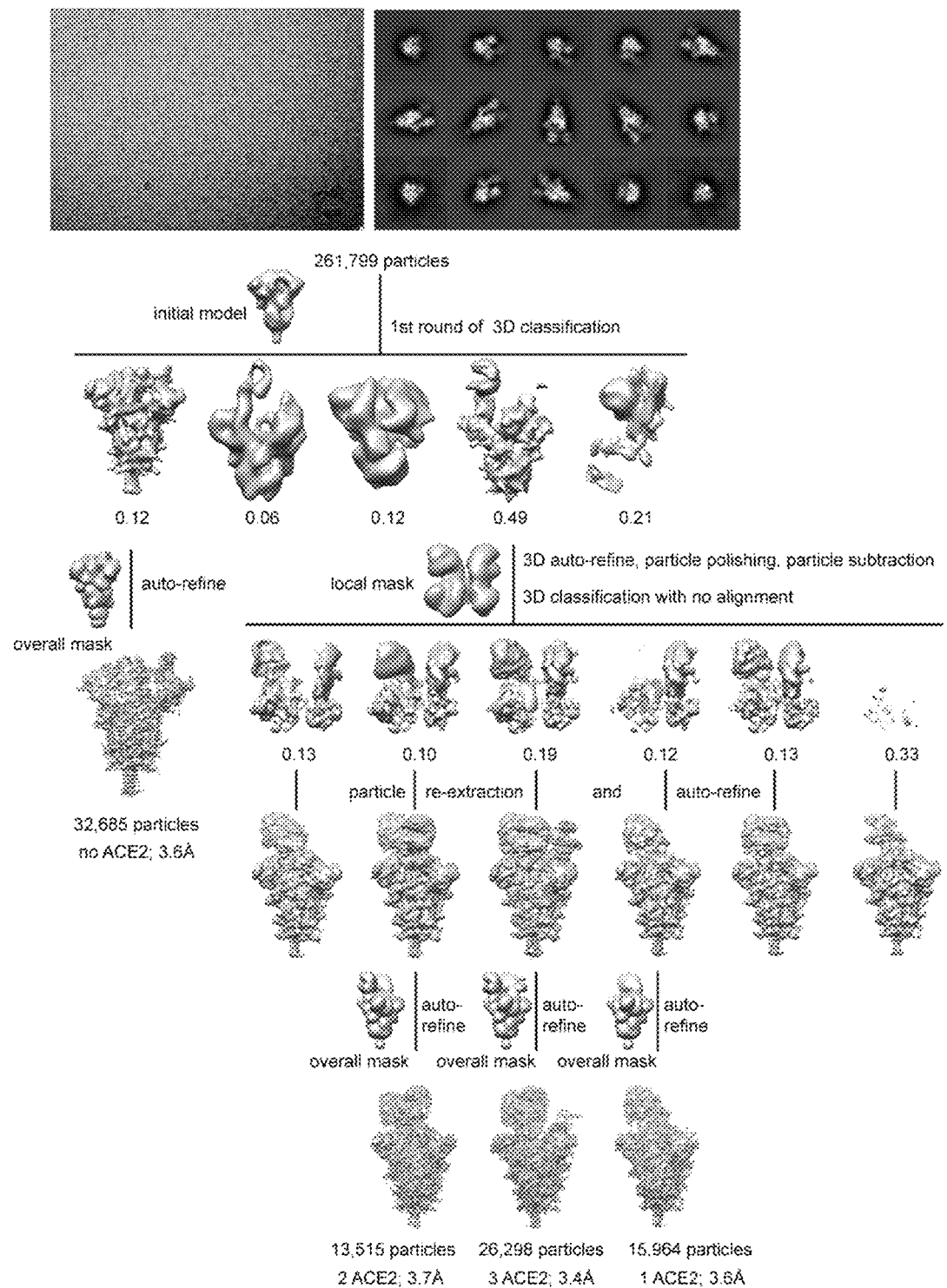
FIG. 11 shows Cryo-EM analysis of the ACE2-S complexes. Top, representative micrograph, and 2D averages of the cryo-EM particle images showing secondary structural features. Bottom, data processing workflow for structures of the free S trimer (no ACE2), S trimer with one ACE2 bound (1 ACE2), S trimer with two ACE2 bound (2 ACE2), S trimer with three ACE2 bound (3 ACE2), as indicated.
Figure 12A:
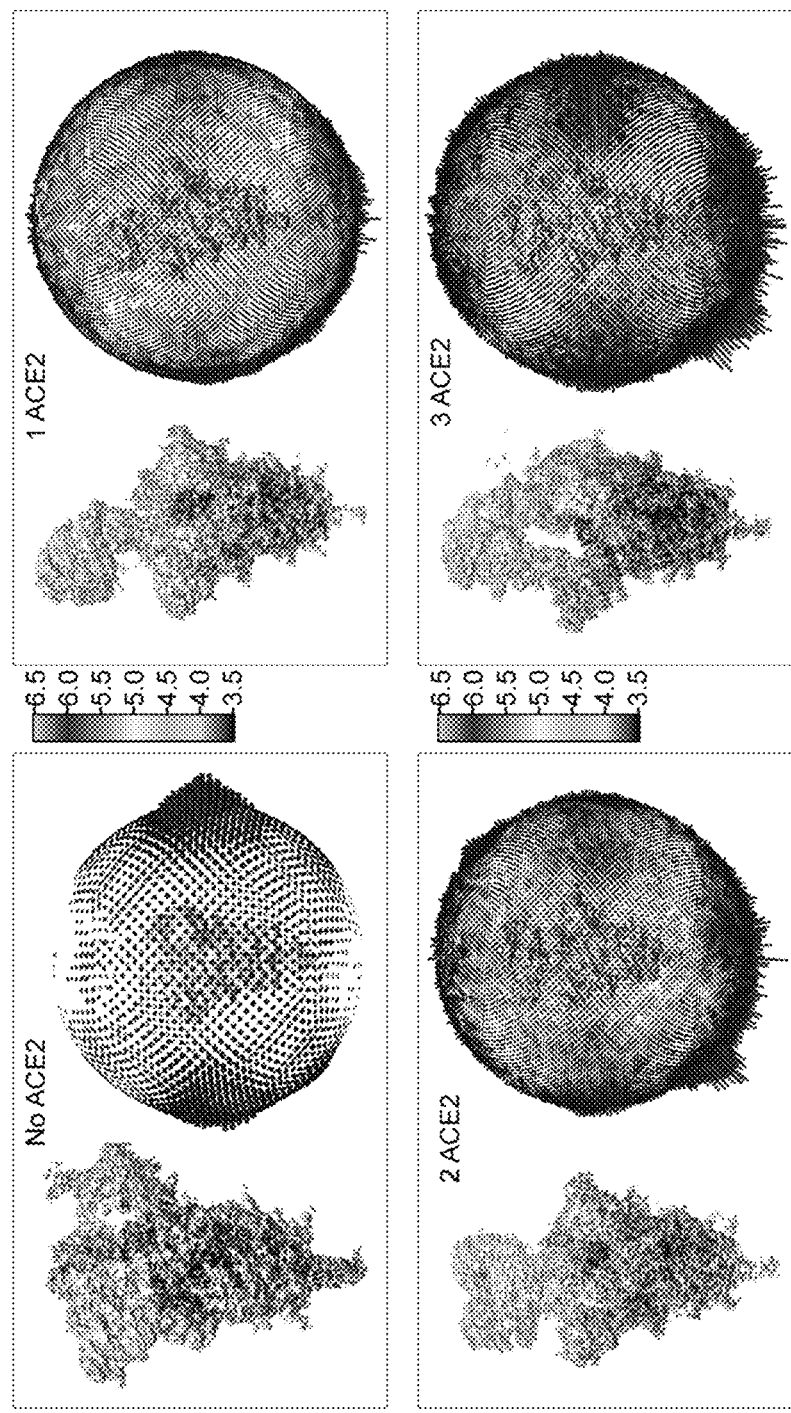
FIGS. 12A-12C show analysis of the 3D reconstructions of the S-ACE2 complexes.
Figure 12B:
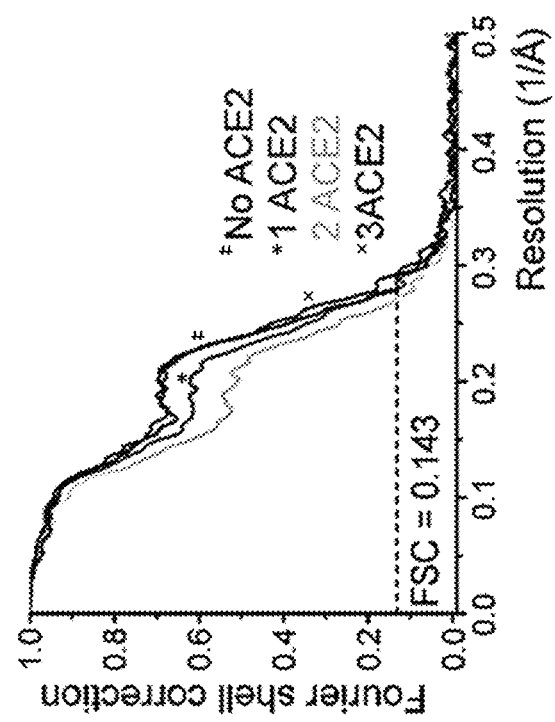
Figure 12C:
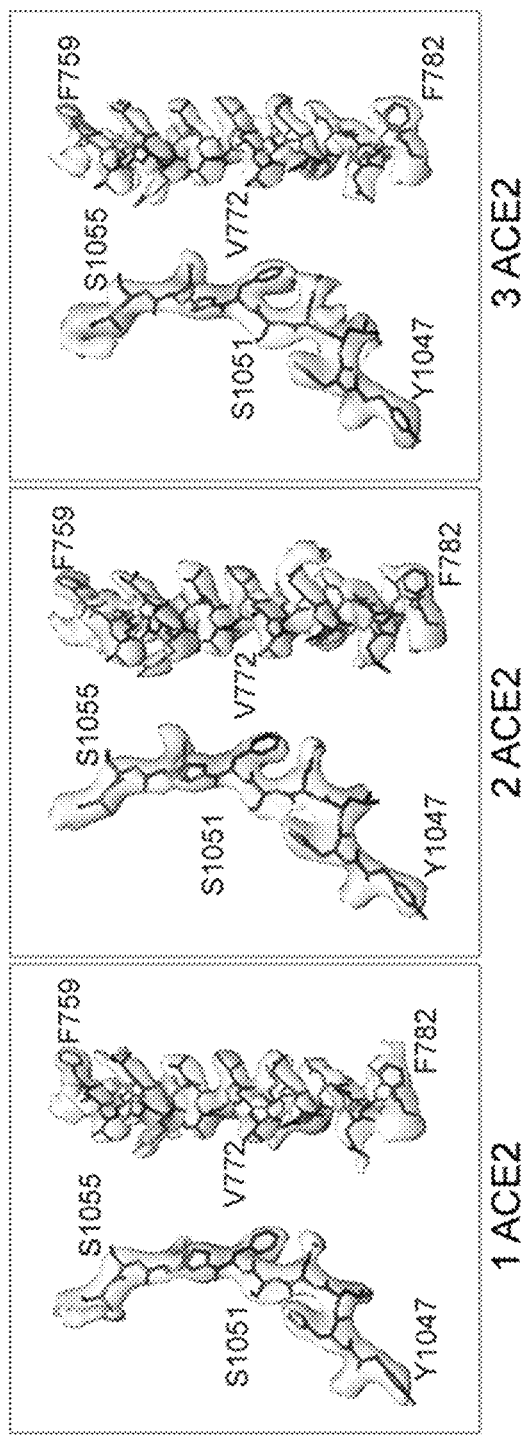

Three different assays were used to assess the neutralization potency of the ACE2 constructs in blocking SARS-CoV-2 infection. The circulating strain during the early days of the pandemic contained a D614 residue in its S protein, but it has subsequently been replaced by an emerging strain harboring a G614 substitution (32). It has been difficult to generate pseudotyped viruses with the full-length S from the D614 strain. A MLV-based pseudovirus assay was first used with a D614 S construct lacking 19 residues of the cytoplasmic tail, which incorporates efficiently into pseudoviruses. In FIG. 10A, the monomeric ACE2$_{615}$ showed the lowest potency with an IC50 value of 24.1 μg/ml. The two dimeric forms, ACE2m$_{615}$-Fc and ACE2$_{740}$-Fc, and the trimeric mutant ACE2$_{615}$-foldon-K353Y had greater potency, with IC50 values ranging from 1.2 to 6.3 μg/ml. The two trimeric forms, ACE2$_{615}$-foldon and ACE2$_{615}$-LL-foldon, and the trimeric mutant ACE2$_{615}$-foldon-H34W neutralized with even greater potency and an IC50 value around 0.6 μg/ml. The most potent inhibitors were ACE2$_{615}$-foldon-T27W and ACE2$_{615}$-foldon-T27Y, which had IC50 values of 0.21 and 0.25 μg/ml, respectively. Thus, the neutralization potency of these ACE2 constructs correlates strictly with their binding affinity, suggesting that the interaction between ACE2 and S is the principal determinant of neutralization of the virus pseudotyped with the CT-truncated S (D614). Neutralization by these ACE2 proteins in the HIV-based pseudovirus assay using a full-length S derived from the G614 circulating strain showed a very similar pattern with ACE2$_{615}$ the weakest and ACE2$_{615}$-foldon-T27W and ACE2$_{615}$-foldon-T27Y the most potent (FIG. 10B). Furthermore, when they were analyzed by a plaque assay with an authentic SARS-CoV-2, the neutralization pattern was almost identical to that from the MLV-based assay (FIG. 10C). The IC50 values for ACE2$_{615}$-foldon-T27W and ACE2$_{615}$-foldon-T27Y were 0.08 and 0.14 μg/ml, respectively. These results indicate that the engineered ACE2 constructs are very potent agents for blocking SARS-CoV-2 infection in cell culture.

Discussion

A recombinant human ACE2, named APN01, is currently under evaluation as a treatment for COVID-19 in a phase 2 clinical trial (NCT04335136), primarily based on the favorable results from a previous phase 1 safety and tolerability trial (NCT00886353) in a small number of healthy individuals (33), as well as on the recent evidence that the protein blocks SARS-CoV-2 infection effectively in vitro (26). APN01 is a soluble ACE2 construct expressing residues 1-740 and probably dimerizes by the neck domain (34), like ACE2$_{740}$-Fc used in the present disclosure. It is demonstrated herein that the best trimeric ACE2 variant, ACE2$_{615}$-foldon-T27W, has >200-fold higher binding affinity for the soluble SARS-CoV-2 S trimer, and ~5-fold and ~13-fold higher neutralization potency against pseudoviruses and authentic viruses, respectively, than does ACE2$_{740}$-Fc, while its peptidase activity and ability to block AT1R activation remain essentially unchanged. Using a deep mutagenesis screening approach, a recent study has identified a dimeric ACE2 variant containing multiple mutations, which led to higher affinity binding to the RBD, but also a substantial loss in the catalytic activity (4-8 fold decrease) than the parental construct with the wildtype sequence (35). One of the mutations from the mutagenesis screening is T27Y, coinciding with the structure-based design. The presently disclosed approach also distinguishes the S protein binding and the peptidase activity, which can be manipulated separately to maximize the therapeutic benefits of an ACE2 construct.

Although the molecular mechanism by which a soluble ACE2 blocks SARS-CoV-2 infection as a decoy receptor is obvious, its protective role against lung injury—a hallmark of severe COVID-19 cases—appears to be more complicated in humans than in animal models. ACE2 knockout mice have more severe ARDS symptoms than do wildtype mice, while ACE2 overexpression appears to be protective (23). Moreover, administration of recombinant ACE2 reduces severity of lung injury in mice caused by respiratory syncytial virus or influenza virus (24-25). In humans, rhACE2 was well tolerated with a short half-life (33), but its infusion did not appear to ameliorate ARDS at least in a small number of patients (36).

The safety in humans of the foldon trimerization tag, derived from the bacteriophage T4 fibritin (30), has been demonstrated by vaccine trials against HIV-1 and SARS-CoV-2 in clinical settings (37, 38). However, a dose in mg/kg body weight of the trimeric ACE2 proteins as a therapeutics is likely much greater than that used as a vaccine (for example, 50-250 μg of foldon stabilized HIV-1 gp140 protein/injection; ref (37)). If the foldon tag induces unacceptable levels of side effects at a high dose in animals or humans, other trimerization domains, such as those in abundant human collagens (39), can be considered. Further improvements of these ACE2-based therapeutic candidates include modifications to enhance protein stability by introducing additional disulfide bonds (which may reduce the catalytic activity), to modulate peptidase activity by mutating residues in or near the active site, and to increase its in vivo residence time in circulation, by strategies such as PEGylation (40).

The structure of the membrane-bound ACE2 dimer formed by the neck domain is not compatible with a binding mode of two protomers interacting with two RBDs from a single S trimer, as depicted in FIGS. 13A-13C. Much stronger binding of ACE2$_{740}$-Fc to the S trimer, as well as greater neutralization potency than those of monomeric ACE2$_{615}$ and even dimeric ACE2m$_{615}$-Fc clearly indicate avidity, suggesting that the ectodomain of either ACE2 or SARS-CoV-2 S protein has much greater avidity-allowing flexibility than the cryo-EM structures imply (18, 28, 41, 42). If the multivalency of the trimeric S protein on the surface of virion and the dimeric ACE2 on the host cells indeed plays an important role during viral attachment, the binding affinity for the virus to latch on the target cells would be much stronger than the values measured using monomeric ACE2 (41). It may help explain the unexpected transmission efficiency of SARS-CoV-2 leading to a pandemic on a surprising scale and raise the hurdle for antivirals to effectively compete with ACE2 for S binding. Trimeric ACE2 variants exerting even greater avidity than the dimeric form on the host cells may have a competitive edge over other RBD-targeting inhibitors, such as monoclonal antibodies, with similar binding affinity.

Methods

Protein Expression and Purification

A synthetic gene encoding an human ACE2 fragment (residues 1-615) fused with a C-terminal 6×His tag was generated by GenScript (Piscataway, N.J.) and cloned into pCMV-IRES-puro expression vector (Codex BioSolutions, Inc, Gaithersburg, Md.) to create the construct pACE2$_{615}$. To construct a trimeric ACE2 variant, a DNA fragment encoding a foldon trimerization tag was inserted between the ACE2 fragment and the His tag by restriction digestion and DNA ligation to give the plasmid pACE2$_{615}$-foldon. Site-specific mutations were introduced to the ACE2$_{615}$-foldon construct by PCR following standard protocols of site-directed mutagenesis. All the ACE2 variants were expressed in HEK 293F cells by transient transfection using Opti-MEM (Gibco-Thermo Fisher Scientific, Waltham, Mass.). After incubation for 4 days at 37° C. with 5.5% $CO_2$, the transfected cells were harvested by centrifugation at 2,524×g for 30 minutes.

For the monomeric ACE2$_{615}$ protein, the cell supernatant was collected by centrifugation and loaded onto a column packed with Ni-NTA agarose beads (Qiagen, Hilden, Germany). The column was washed with a buffer containing 20 mM Tris-HCl, pH 7.5, and 300 mM NaCl. The protein was eluted using a buffer containing 100 mM imidazole, and further purified by gel filtration chromatography on a Superdex 200 Increase 10/300 GL column (GE Healthcare, Chicago, Ill.)

To purify the dimeric ACE2$_{615}$-Fc and ACE2$_{740}$-Fc proteins, the cell supernatant was collected and loaded to a column packed with GammaBind Plus Sepharose beads (GE Healthcare). The column was washed with PBS. The protein was eluted using 100 mM glycine (pH 2.5) and neutralized immediately with 2 M Tris-HCl (pH 8.0). The eluted protein was further purified by gel filtration chromatography on a Superdex 200 Increase 10/300 GL column.

For all the ACE2$_{615}$-foldon variants, which were not secreted efficiently, the cell pellet was resuspended in the lysis buffer (20 mM Tris-HCl, pH 7.5, 300 mM NaCl, 1% NP40, 20 mM imidazole) and rocked gently for 1 hour at 4° C., followed by spinning at 17,554×g for 30 minutes to remove cell debris. The supernatant was loaded to a column packed with Ni-NTA agarose beads (Qiagen). The column was washed with a buffer containing 20 mM Tris-HCl, pH 7.5, 300 mM NaCl and 50 mM imidazole and the protein was eluted using a buffer containing 20 mM Tris-HCl, pH 7.5, 300 mM NaCl and 300 mM imidazole. The eluted protein was further purified by gel filtration chromatography on a Superdex 200 Increase 10/300 GL column.

To produce a stabilized ectodomain of SARS-CoV-2 S trimer protein, a synthetic gene (kindly provided by Dr. Dan Barouch), encoding residues 1-1208 with the furin cleavage site (residues 682-685) replaced by a "GGSG" sequence, residues K986 and V987 substituted by prolines, and addition of a foldon trimerization tag followed by a C-terminal 6×HisTag, was cloned into the vector pCMV-IRES-puro. The expression construct was transiently transfected in HEK 293T cells using polyethylenimine (Polysciences, Inc, Warrington, Pa.). Protein was purified from cell supernatants using Ni-NTA resin (Qiagen), the eluted fractions containing S protein were pooled, concentrated, and further purified by gel filtration chromatography on a Superose 6 column (GE Healthcare).

Cryo-EM Sample Preparation and Data Collection

To prepare cryo grids, 3.5 µl of the freshly prepared mixture of the soluble S trimer and monomeric ACE2 (1:3 molar ratio) at ~1 mg/ml was applied to a 1.2/1.3 Quantifoil grid (Quantifoil Micro Tools GmbH, Germany), which had been glow discharged with a PELCO easiGlow™ Glow Discharge Cleaning system (Ted Pella, Inc., Redding, Calif.) for 60 s at 15 mA. Grids were immediately plunge-frozen in liquid ethane using a Vitrobot Mark IV (Thermo Fisher Scientific), and excess protein was blotted away using grade 595 filter paper (Ted Pella, Inc.) with a blotting time of 4 s, a blotting force of −12 at 4° C. in 100% humidity. The grids were first screened for ice thickness and particle distribution using a Talos Arctica transmission electron microscope (Thermo Fisher Scientific), operated at 200 keV and equipped with a K3 direct electron detector (Gatan), at the Harvard Cryo-EM Center for Structural Biology. For data collection, images were acquired with selected grids using a Titan Krios transmission electron microscope (Thermo Fisher Scientific) operated at 300 keV with a BioQuantum GIF/K3 direct electron detector. Automated data collection was carried out using SerialEM version65 at a nominal magnification of 105,000× and the K3 detector in counting mode (calibrated pixel size, 0.825 Å) at a exposure rate of ~14.8 electrons per physical pixel per second. Each movie had a total accumulated electron exposure of 50 e/Å2 fractionated in 50 frames of 50 ms. Datasets were acquired using a defocus range of 1.5-2.6 µm.

Image Processing, 3D Reconstructions and Model Building

Drift correction for cryo-EM images was performed using MotionCor2 (43), and contrast transfer function (CTF) was estimated by CTFFIND4 (44) using motion-corrected sums without dose-weighting. Motion corrected sums with dose-weighting were used for all image processing. CrYOLO (45) was used for particle picking, and RELION3.0.8 (46) was used for 2D classification, 3D classification and refinement. A total of 407,761 particles were extracted from 4,292 images. The selected particles were subjected to 2D classification, giving a total of 261,799 good particles. A low-resolution negative-stain reconstruction of the sample was low-pass-filtered to 40 Å and used as an initial model for 3D classification in C1 symmetry. One class containing 32,685 particles appeared to represent the free S trimer with no ACE bound was further refined in C1 symmetry, giving a reconstruction at 3.6 Å resolution. Another major class with ~49% of the selected particles showing density for ACE2 was refined in C1 symmetry and subsequently subjected to CTF refinement, Bayesian polishing and particle subtraction by masking out the ACE2-RBD density, followed by 3D classification without alignment in six classes. Whole particles were re-extracted based on the six classes from the masked local classification and refined further, revealing different stoichiometry for ACE2 binding (one ACE2 per S trimer, two ACE2 per S trimer, and three ACE2 per S trimer). Three best maps representing each type of complexes were chosen and further refined in C1 symmetry after CTF refinement and Bayesian polishing, leading to one reconstruction of the complex with one ACE2 bound at 3.6 Å resolution from 15,964 particles; another reconstruction of the complex with two ACE2 bound at 3.7 Å resolution from 13,515 particles and a third reconstruction of the complex with three ACE2 bound at 3.4 Å resolution from 26,298 particles. Reported resolutions are based on the gold-standard Fourier shell correlation (FSC) using the 0.143 criterion. All density maps were corrected from the modulation transfer function of the K3 detector and then sharpened by applying a temperature factor that was estimated using post-processing in RELION. Local resolution was determined using RELION with half-reconstructions as input maps.

The initial templates for model building used the stabilized SARS-CoV-2 S ectodomain trimer structure (PDB ID: 6vyb) and ACE2 from the ACE2-B0AT1 complex structure (PDB ID: 6M17). Several rounds of manual building were performed in Coot. Iteratively, refinement was performed in both Phenix (47) (real space refinement) and ISOLDE (48), and the Phenix refinement strategy included rigid body fit, minimization_global, local_grid_search, and adp, with rotamer, Ramachandran, and reference-model restraints, using 6vyb and 6M17 as the reference model. The refinement statistics are summarized in Table 5.

TABLE 5

| EM data collection and reconstruction statistics | |
|---|---|
| Protein | 2019-nCoV S perfusion |
| EMDB | |
| Microscope | FEI Titan Krios |
| Voltage(kV) | 300 |
| Detector | Gatan K3 |
| Magnification(nominal) | 105,000 |
| Pixel size (Å/pix) | 0.825 |
| Flux ($e^-$/pix/sec) | 14.83 |
| Frames per exposure | 50 |
| Exposure ($e^-/Å^2$) | 50.05 |
| Dose per frame($e/Å^2$) | 1.001 |
| Defocus range (μm) | 1.6-2.7 |
| Micrographs collected | 4,292 |
| Particles extracted/final | 407,761/88,462 |
| Symmetry imposed | C1 |

| Class | 0ace | 1ace | 2ace | 3ace |
|---|---|---|---|---|
| Map sharpening B-factor | −78.95 | −83.01 | −86.05 | — |
| Resolution at 0.143 FSC (Å) | 3.60 | 3.60 | 3.73 | 3.44 |
| Model refinement and validation statistics | | | | |
| PDB | | | | |
| Composition | | | | |
| Amino acids | 2906 | 3499 | 4106 | 4719 |
| Glycans | 59 | 72 | 84 | 96 |
| RMSD bonds (Å) | 0.010 | 0.006 | 0.013 | 0.010 |
| RMSD angles (°) | 1.033 | 0.935 | 1.581 | 1.252 |
| Mean B-factors | | | | |
| Amino acids | 75.61 | 32.03 | 33.50 | 30.58 |
| Glycans | 131.7 | 51.75 | 55.17 | 47.49 |
| Ramachandran | | | | |
| Favored (%) | 90.76 | 93.76 | 90.60 | 91.80 |
| Allowed(%) | 9.20 | 6.22 | 9.18 | 8.18 |
| Outliers(%) | 0.04 | 0.03 | 0.22 | 0.02 |
| Rotamer outliers (%) | 0.31 | 0.07 | 10.39 | 12.10 |
| Clash score | 26.97 | 21.42 | 32.91 | 33.88 |
| C-beta outliers (%) | 0.00 | 0.03 | 0.65 | 0.07 |
| CC (mask) | 0.79 | 0.73 | 0.68 | 0.69 |
| MolProbity score | 2.45 | 2.24 | 3.31 | 3.33 |
| EMRinger score | 1.26 | 2.22 | 1.85 | 1.38 |

Binding Assay by Bio-Layer Interferometry (BLI)

Binding of ACE2 variants to the soluble S trimer was measured using an Octet RED384 system (ForteBio, Fremont, Calif.). Each ACE2 protein was diluted using the running buffer (PBS, 0.005% Tween 20, 0.25 mg/ml BSA) and transferred to a 96-well plate. The soluble S protein was immobilized to Amine Reactive $2^{nd}$ Generation (AR2G) biosensors (Fortebio), following a protocol recommended by the manufacturer. After equilibrating in the running buffer for 5 minutes, the sensors with immobilized S protein were dipped in the wells containing the ACE2 protein at various concentrations (1.852-150 nM for $ACE2_{615}$; 0.926-75 nM for $ACE2_{615}$-Fc and $ACE2_{7}40$-Fc; 0.617-50 nM for all the $ACE2_{615}$-foldon variants) for 5 minutes to measure the association rate. The sensors were then dipped in the running buffer for 10 minutes to determine the dissociation rate. Control sensors with no S protein were also dipped in the ACE2 solutions and the running buffer as references. Recorded sensorgrams with background subtracted from the references were analyzed using the software Octet Data Analysis HT Version 11.1 (Fortebio). The curves for monomeric ACE2 were fit to a 1:1 binding model, while those for the oligomeric ACE2 variants were fit to a bivalent binding model.

ACE2 Peptidase Activity Assay

The catalytic activity of the ACE2 variants was measured by detecting a free fluorophore 7-methoxycoumarin-4-acetic acid (MCA) released from a synthetic peptide substrate, using an ACE2 activity kit (BioVision, Milpitas, Calif.). The $ACE2_{615}$ and $ACE2_{615}$-foldon variants were diluted to 0.25 μg/ml using the assay buffer from the kit. The $ACE2_{615}$-Fc and $ACE2_{740}$-Fc proteins were diluted to 0.38 and 0.30 μg/ml, respectively, to keep the same number of the active sites as other ACE2 variants. 50 μl of diluted protein was set in the 96-well plate. Immediately before recording fluorescence signals, 50 μl substrate diluted in the assay buffer, following a protocol recommended by the manufacturer, was added to each well. Fluorescence signals were recorded in a kinetic mode by a Flexstation 3 Multi Mode Microplate Reader (Molecular Devices, San Jose, Calif.). The specific activity was calculated as the amount of the released fluorophore divided by the reaction time and the amount of the ACE2 protein using the data within the initial linear phase, as described in the protocol provided by the manufacturer. To determine the initial linear phase, fluorescence signals were recorded with 1.25, 0.25 and 0.125 μg of $ACE2_{615}$ protein, respectively, reaching maximum after the substrates were completely cleaved. Data from the first 2 minutes within the linear phase with signals less than 10% of the maximum were used for the calculation. The amount of released MCA was derived from the increase of the fluorescence signal divided by the slope of the MCA standard curve.

Inhibition of Ang II-Induced AT1R Activation

To treat the Ang II peptide with each ACE2 variant, 2 µl of ACE2 protein at 0.5 mg/ml were added to 198 µl of an assay buffer (1×PBS, 40 mM Tris-HCl, pH6.8, 20 µM $ZnCl_2$) containing 65 µM Ang II peptide. The reactions were incubated at 37° C. for 40 min, and then quenched by addition of 50 µl of 0.5 M EDTA. The final concentration of Ang II peptide was 52 µM. As a time 0 control, 198 µl of the assay buffer containing 65 µM Ang II was incubated with EDTA at 37° C. first, followed by addition of 2 µl of each ACE2 protein (0.5 mg/ml).

Changes in the intracellular calcium concentration in AT1R-expressing cells when induced by Ang II peptide were measured to monitor the activation of the receptor. Briefly, HEK293 cells were transfected with pCMV-AT1R-IRES-Puro gene using Lipofectamine 3000 reagent (Thermo Fisher Scientifics). Approximately 24 hours post-transfection, the cells were transferred into a 384-well black clear plate at a density of $1.2 \times 10^4$ cells/well in 20 µl culture medium. On day 4, 20 µl of 1× Non-Wash Calcium Dye solution (CB-80500-301, Codex BioSolutions Inc) was added into each well. The cell plate was incubated at 37° C. in a $CO_2$ incubator for 1 hour. The pretreated ligands (Ang II peptide) at various concentrations (0.005-500 nM) were prepared in 1×HBSS with 20 mM HEPES (pH7.46). Fluorescent intensity in each well was recorded on an FDSS 7000 (Hamamatsu Corporation, Bridgewater, N.J.) at the rate of 1 image/sec (Ex 480 nM and Em 540 nM) and the base line of each well was also recorded for 10 seconds. After the online addition of 10 µl of the prepared ligands (the final concentration of 0.001-100 nM), the fluorescent intensity of each well was recorded at the rate of 1 image/sec for additional 170 seconds.

MLV-Based Pseudovirus Assay

Murine Leukemia Virus (MLV) particles (all plasmids of the MLV components were kindly provided by Dr. Gary Whittaker at Cornell University and Drs. Catherine Chen and Wei Zheng at National Center for Advancing Translational Sciences, National Institutes of Health), pseudotyped with a SARS-CoV-2 S protein construct were generated in HEK 293T cells, following a protocol described previously for SARS-CoV (49, 50). To enhance incorporation, C-terminal 19 residues in the cytoplasmic tail of the SARS-CoV-2 S protein containing D614 were deleted. To prepare for infection, $7.5 \times 10^3$ of Expi-293F cells, stably transfected with a full-length human ACE2 expression construct, in 15 µl culture medium were plated into a 384-well white-clear plate coated with poly-D-Lysine to enhance cell attachment. On day 2, 12.5 µl of SARS-CoV-2 MLV pseudoviruses were mixed with 5 µl of each ACE2 variant at different concentrations (0.001-300 µg/ml) and incubated at 37° C. for 1 hr. After the medium in each well containing the cells was removed, 17.5 µl of each ACE2-virus mixture were added. The plate was centrifuged at 54×g for 15 min at 4° C. and additional 7.5 µl of culture medium were then added. The total final volume in each well was 25 µl. The cells were then incubated at 37° C. for 42 hr. Luciferase activities were measured with Firefly Luciferase Assay Kit (CB-80552-010, Codex BioSolutions Inc). IC50 values were calculated based on curve fitting in GraphPad Prism.

HIV-Based Pseudovirus Assay

Neutralization of HIV-based pseudovirus containing a full-length SARS-CoV-2 S protein was measured using a single-round infection assay in HEK 293T/ACE2 target cells. Pseudotyped virus particles were produced in 293T/17 cells (ATCC) by co-transfection of a plasmid encoding codon-optimized SARS-CoV-2 full-length S containing G614, a packaging plasmid pCMV ΔR8.2 expressing HIV gag and pol, and a luciferase reporter plasmid pHR' CMV-Luc. All plasmids were kindly provided by Dr. Barney Graham (NIH, Vaccine Research Center). The 293T cell line stably overexpressing the human ACE2 protein was created by the Farzan group at Scripps Research Institute. For neutralization assays, serial dilutions of the ACE2 constructs were performed in duplicate followed by addition of pseudoviruses. Plates were incubated for 1 hour at 37° C. followed by addition of 293T/ACE2 target cells ($1 \times 10^4$/ well). Wells containing cells and pseudoviruses without ACE2 proteins or cells alone were positive and negative infection controls, respectively. Assays were harvested on day 3 using BrightGlo luciferase reagent (Promega, Madison, Wis.) and luminescence detected with a Victor luminometer (PerkinElmer, Waltham, Mass.). IC50 values are reported as the ACE2 protein concentration that inhibited 50% virus infection. All neutralization experiments were repeated twice with similar results.

Neutralization of Authentic SARS-CoV-2

ACE2 variants were serially diluted in Dulbecco's Phosphate Buffered Saline (DPBS) (Gibco™) using half-log dilutions starting at 31,579 ng/ml. Dilutions were prepared in triplicate for each protein. Each dilution was incubated at 37° C. in 5% $CO_2$ for 1 hour with 1,000 plaque forming units/ml (PFU/ml) of SARS-CoV-2 (isolate USA-WA1/2020). Controls included Dulbecco's Modified Eagle Medium (DMEM) (Gibco-Thermo Fisher Scientific) containing 2% fetal bovine serum (Gibco-Thermo Fisher Scientific) and antibiotic-antimycotic (Gibco-Thermo Fisher Scientific) only as a negative control, 1000 PFU/ml SARS-CoV-2 (USA-WA1/2020) incubated with DPBS, and 1000 PFU/ml SARS-CoV-2 incubated with DMEM. 200 µl of each dilution or control were added to confluent monolayers of NR-596 Vero E6 cells in triplicate and incubated for 1 hour at 37° C. and 5% $CO_2$. The plates were gently rocked every 5-10 minutes to prevent monolayer drying. The monolayers were then overlaid with a 1:1 mixture of 2.5% Avicel® RC-591 microcrystalline cellulose and carboxymethylcellulose sodium (DuPont Nutrition & Biosciences, Wilmington, Del.) and 2× Modified Eagle Medium (Temin's modification, Gibco-Thermo Fisher Scientific) supplemented with 2× antibiotic-antimycotic, 2× GlutaMAX (Gibco-Thermo Fisher Scientific) and 10% fetal bovine serum. Plates were incubated at 37° C. and 5% $CO_2$ for 2 days. The monolayers were fixed with 10% neutral buffered formalin and stained with 0.2% aqueous Gentian Violet (RICCA Chemicals, Arlington, Tex.) in 10% neutral buffered formalin for 30 min, followed by rinsing and plaque counting. The half maximal inhibitory concentrations (IC50) were calculated using GraphPad Prism 8.

REFERENCES

1. Duan, K. et al. Effectiveness of convalescent plasma therapy in severe COVID-19 patients. *Proc Natl Acad Sci USA* 117, 9490-9496 (2020).
2. Bloch, E. M. et al. Deployment of convalescent plasma for the prevention and treatment of COVID-19. *J Clin Invest* 130, 2757-2765 (2020).
3. Shen, C. et al. Treatment of 5 Critically Ill Patients With COVID-19 With Convalescent Plasma. *JAMA* (2020).
4. Wec, A. Z. et al. Broad neutralization of SARS-related viruses by human monoclonal antibodies. *Science* (2020).

5. Shi, R. et al. A human neutralizing antibody targets the receptor binding site of SARS-CoV-2. *Nature* (2020).
6. Chi, X. et al. A neutralizing human antibody binds to the N-terminal domain of the Spike protein of SARS-CoV-2. *Science* (2020).
7. Wu, Y. et al. A noncompeting pair of human neutralizing antibodies block COVID-19 virus binding to its receptor ACE2. *Science* 368, 1274-1278 (2020).
8. Xia, S. et al. Inhibition of SARS-CoV-2 (previously 2019-nCoV) infection by a highly potent pan-coronavirus fusion inhibitor targeting its spike protein that harbors a high capacity to mediate membrane fusion. *Cell Res* 30, 343-355 (2020).
9. Xia, S. et al. Fusion mechanism of 2019-nCoV and fusion inhibitors targeting HR1 domain in spike protein. *Cell Mol Immunol* 17, 765-767 (2020).
10. Sanders, J. M., Monogue, M. L., Jodlowski, T. Z. & Cutrell, J. B. Pharmacologic Treatments for Coronavirus Disease 2019 (COVID-19): A Review. *JAMA* (2020).
11. Wu, R. et al. An Update on Current Therapeutic Drugs Treating COVID-19. *Curr Pharmacol Rep*, 1-15 (2020).
12. Boulware, D. R. et al. A Randomized Trial of Hydroxychloroquine as Postexposure Prophylaxis for Covid-19. *N Engl J Med* 383, 517-525 (2020).
13. Jin, Z. et al. Structure of M(pro) from SARS-CoV-2 and discovery of its inhibitors. *Nature* 582, 289-293 (2020).
14. Gao, Y. et al. Structure of the RNA-dependent RNA polymerase from COVID-19 virus. *Science* 368, 779-782 (2020).
15. Polak, S. B., Van Gool, I. C., Cohen, D., von der Thusen, J. H. & van Paassen, J. A systematic review of pathological findings in COVID-19: a pathophysiological timeline and possible mechanisms of disease progression. *Mod Pathol* (2020).
16. Zhou, P. et al. A pneumonia outbreak associated with a new coronavirus of probable bat origin. *Nature* (2020).
17. Hoffmann, M. et al. SARS-CoV-2 Cell Entry Depends on ACE2 and TMPRSS2 and Is Blocked by a Clinically Proven Protease Inhibitor. *Cell* (2020).
18. Yan, R. et al. Structural basis for the recognition of SARS-CoV-2 by full-length human ACE2. *Science* 367, 1444-1448 (2020).
19. Tikellis, C., Bernardi, S. & Burns, W. C. Angiotensin-converting enzyme 2 is a key modulator of the renin-angiotensin system in cardiovascular and renal disease. *Curr Opin Nephrol Hypertens* 20, 62-8 (2011).
20. Clarke, N. E. & Turner, A. J. Angiotensin-converting enzyme 2: the first decade. *Int J Hypertens* 2012, 307315 (2012).
21. Dasgupta, C. & Zhang, L. Angiotensin II receptors and drug discovery in cardiovascular disease. *Drug Discov Today* 16, 22-34 (2011).
22. Hemnes, A. R. et al. A potential therapeutic role for angiotensin-convertingenzyme 2 in human pulmonary arterial hypertension. *Eur Respir J* 51(2018).
23. Imai, Y. et al. Angiotensin-converting enzyme 2 protects from severe acute lung failure. *Nature* 436, 112-6 (2005).
24. Gu, H. et al. Angiotensin-converting enzyme 2 inhibits lung injury induced by respiratory syncytial virus. *Sci Rep* 6, 19840 (2016).
25. Zou, Z. et al. Angiotensin-converting enzyme 2 protects from lethal avian influenza A H5N1 infections. *Nat Commun* 5, 3594 (2014).
26. Monteil, V. et al. Inhibition of SARS-CoV-2 Infections in Engineered Human Tissues Using Clinical-Grade Soluble Human ACE2. *Cell* 181, 905-913 e7 (2020).
27. Kirchdoerfer, R. N. et al. Stabilized coronavirus spikes are resistant to conformational changes induced by receptor recognition or proteolysis. *Sci Rep* 8, 15701 (2018).
28. Cal, Y. et al. Distinct conformational states of SARS-CoV-2 spike protein. *Science* (2020).
29. Zhou, T. et al. A pH-dependent switch mediates conformational masking of SARS-CoV-2 spike. *bioRxiv* (2020).
30. Meier, S., Guthe, S., Kiefhaber, T. & Grzesiek, S. Foldon, the natural trimerization domain of T4 fibritin, dissociates into a monomeric A-state form containing a stable beta-hairpin: atomic details of trimer dissociation and local beta-hairpin stability from residual dipolar couplings. *J Mol Biol* 344, 1051-69 (2004).
31. Lan, J. et al. Structure of the SARS-CoV-2 spike receptor-binding domain bound to the ACE2 receptor. *Nature* (2020).
32. Korber, B. et al. Tracking Changes in SARS-CoV-2 Spike: Evidence that D614G Increases Infectivity of the COVID-19 Virus. *Cell* 182, 812-827 e19 (2020).
33. Haschke, M. et al. Pharmacokinetics and pharmacodynamics of recombinant human angiotensin-converting enzyme 2 in healthy human subjects. *Clin Pharmacokinet* 52, 783-92 (2013).
34. Poglitsch, M. et al. Recombinant Expression and Characterization of Human and Murine ACE2: Species-Specific Activation of the Alternative Renin-Angiotensin-System. *Int J Hypertens* 2012, 428950 (2012).
35. Chan, K. K. et al. Engineering human ACE2 to optimize binding to the spike protein of SARS coronavirus 2. *Science* 369, 1261-1265 (2020).
36. Khan, A. et al. A pilot clinical trial of recombinant human angiotensin-converting enzyme 2 in acute respiratory distress syndrome. *Crit Care* 21, 234 (2017).
37. Barouch, D. H. et al. Evaluation of a mosaic HIV-1 vaccine in a multicentre, randomised, double-blind, placebo-controlled, phase 1/2a clinical trial (APPROACH) and in rhesus monkeys (NHP 13-19). *Lancet* 392, 232-243 (2018).
38. Mulligan, M. J. et al. Phase 1/2 study of COVID-19 RNA vaccine BNT162b1 in adults. *Nature* (2020).
39. Sharma, U. et al. Structural basis of homo- and heterotrimerization of collagen I. *Nat Commun* 8, 14671 (2017).
40. Jevsevar, S., Kunstelj, M. & Porekar, V. G. PEGylation of therapeutic proteins. *Biotechnol J* 5, 113-28 (2010).
41. Wrapp, D. et al. Cryo-EM structure of the 2019-nCoV spike in the prefusion conformation. *Science* (2020).
42. Walls, A. C. et al. Structure, function and antigenicity of the SARS-CoV-2 spike glycoprotein. *Cell*, DOI: 10.1016/j.cell.2020.02.058 (2020).
43. Zheng, S. Q. et al. MotionCor2: anisotropic correction of beam-induced motion for improved cryo-electron microscopy. *Nat Methods* 14, 331-332 (2017).
44. Rohou, A. & Grigorieff, N. CTFFIND4: Fast and accurate defocus estimation from electron micrographs. *J Struct Biol* 192, 216-21 (2015).
45. Wagner, T. et al. SPHIRE-crYOLO is a fast and accurate fully automated particle picker for cryo-EM. *Commun Biol* 2, 218 (2019).
46. Scheres, S. H. RELION: implementation of a Bayesian approach to cryo-EM structure determination. *J Struct Biol* 180, 519-30 (2012).
47. Adams, P. D. et al. PHENIX: a comprehensive Python-based system for macromolecular structure solution. *Acta crystallographica. Section D, Biological crystallography* 66, 213-21 (2010).

48. Croll, T. I. ISOLDE: a physically realistic environment for model building into low-resolution electron-density maps. *Acta Crystallogr D Struct Biol* 74, 519-530 (2018).
49. Millet, J. K. & Whittaker, G. R. Murine Leukemia Virus (MLV)-based Coronavirus Spike-pseudotyped Particle Production and Infection. *Bio Protoc* 6(2016).
50. Chen, C. Z. et al. Identifying SARS-CoV-2 entry inhibitors through drug repurposing screens of SARS-S and MERS-S pseudotyped particles. *bioRxiv* (2020).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject inventions are explicitly disclosed herein, the above specification is illustrative and not restrictive. Many variations of the inventions will become apparent to those skilled in the art upon review of this specification and the claims below. The full scope of the inventions should be determined by reference to the claims, along with their full scope of equivalents, and the specification, along with such variations.

What is claimed is:

1. An isolated polypeptide monomer comprising an angiotensin-converting enzyme 2 (ACE2) ectodomain and an oligomerization domain, wherein the polypeptide monomer comprises at least 94% sequence identity to SEQ ID NO: 2 or SEQ ID NO: 3.

2. The polypeptide monomer of claim 1, wherein the oligomerization domain provides for the trimerization of the polypeptide monomers.

3. The polypeptide monomer of claim 2, wherein the oligomerization domain comprises a foldon trimerization tag.

4. The polypeptide monomer of claim 1, wherein the oligomerization domain provides for the tetramerization of the polypeptide monomers.

5. The polypeptide monomer of claim 4, wherein the oligomerization domain comprises a streptavidin domain.

6. An oligomeric complex comprising two or more polypeptide monomers, wherein at least two monomers are associated with each other, and wherein the monomers comprise any of the polypeptide monomers of claim 1.

7. An oligomeric complex comprising three polypeptide monomers, wherein at least two monomers are associated with each other, and wherein the monomers comprise the polypeptide monomers of claim 2.

8. An oligomeric complex comprising four polypeptide monomers, wherein at least two monomers are associated with each other, and wherein the monomers comprise the polypeptide monomers of claim 4.

9. The polypeptide monomer of claim 1, wherein the ACE2 ectodomain comprises a stabilizing mutation, wherein the mutation increases the stability of the polypeptide monomer when associated with at least one polypeptide monomer.

10. The polypeptide monomer of claim 1, wherein the polypeptide monomer comprises a mutation that decreases the off-rate of the interaction with a SARS-CoV-2 S protein.

11. The polypeptide monomer of claim 10, wherein the mutation that decreases the off-rate is on the interface with the SARS-CoV-2 S protein.

12. The oligomeric complex of claim 6, wherein the at least two monomers comprise ACE2 ectodomain comprising a stabilizing mutation, wherein the mutation increases the stability of the polypeptide monomer when associated with at least one polypeptide monomer.

13. The oligomeric complex of claim 6, wherein the polypeptide monomer comprises a mutation that decreases the off-rate of the interaction with a SARS-CoV-2 S protein.

14. The oligomeric complex of claim 13, wherein the mutation that decreases the off-rate is on the interface with the SARS-CoV-2 S protein.

15. A kit comprising the polypeptide monomer of claim 1.

16. A method for the determination of the presence of a SARS-CoV-2 in a sample, said method comprising the steps of: allowing the sample to contact a diagnostically effective amount of a binding molecule comprising the polypeptide monomer of claim 1 under conditions that allow the binding of the binding molecule to at least one SARS-CoV-2 S protein; and detecting whether the binding molecule specifically binds to a molecule of the sample.

17. A method for the determination of a SARS-CoV-2 virus infection in a patient, said method comprising the steps of: allowing the sample to contact a diagnostically effective amount of a binding molecule comprising the polypeptide monomer of claim 1 under conditions that allow the binding of the binding molecule to at least one SARS-CoV-2 S protein; and detecting whether the binding molecule specifically binds to a molecule of the sample.

18. A method for treating a patient in need thereof, said method comprising the step of administering a therapeutic amount of the polypeptide monomer of claim 1.

* * * * *